(12) United States Patent
Lauritzen et al.

(10) Patent No.: US 12,354,718 B2
(45) Date of Patent: Jul. 8, 2025

(54) USER INTERFACES RELATED TO CLINICAL DATA

(71) Applicant: Apple Inc., Cupertino, CA (US)

(72) Inventors: Christopher David Lauritzen, San Francisco, CA (US); Matthew W. Crowley, Sunnyvale, CA (US); Kristin M. Canavan, San Francisco, CA (US); Pablo F. Caro, San Francisco, CA (US); Dmitri Cavander, San Francisco, CA (US); Nicholas D. Felton, Sunnyvale, CA (US); Eamon F. Gilravi, San Francisco, CA (US); Charmian B. Naguit, San Rafael, CA (US)

(73) Assignee: Apple Inc., Cupertino, CA (US)

( * ) Notice: Subject to any disclaimer, the term of this patent is extended or adjusted under 35 U.S.C. 154(b) by 562 days.

(21) Appl. No.: 17/540,991

(22) Filed: Dec. 2, 2021

(65) Prior Publication Data

US 2022/0392589 A1 Dec. 8, 2022

Related U.S. Application Data

(60) Provisional application No. 63/197,422, filed on Jun. 6, 2021.

(51) Int. Cl.
*G16H 10/60* (2018.01)
*G06F 3/04817* (2022.01)
(Continued)

(52) U.S. Cl.
CPC ......... *G16H 10/60* (2018.01); *G06F 3/04817* (2013.01); *G06F 3/0482* (2013.01); *G06F 3/0488* (2013.01); *G16H 20/00* (2018.01)

(58) Field of Classification Search
CPC ........ G16H 10/60; G16H 20/00; G16H 10/40; G16H 40/40; G16H 40/60; G06F 3/04817; G06F 3/0482; G06F 3/0488
(Continued)

(56) References Cited

U.S. PATENT DOCUMENTS 4,803,625 A * 2/1989 Fu ......................... G16H 40/67
128/920
2016/0110507 A1 4/2016 Abbo
(Continued)

OTHER PUBLICATIONS

Struikman B et al. Features of a Patient Portal for Blood Test Results and Patient Health Engagement: Web-Based Pre-Post Experiment. J Med Internet Res. Jul. 20, 2020;22(7):e15798. doi: 10.2196/15798. PMID: 32706704; PMCID (Year: 2020).*
(Continued)

*Primary Examiner* — Joshua B Blanchette
(74) *Attorney, Agent, or Firm* — DLA Piper LLP (US)

(57) ABSTRACT

The present disclosure generally relates to methods and user interfaces for displaying and managing user interfaces including information related to physiological measurements. In some embodiments, methods and user interfaces for displaying lab types based on whether a lab type had been previously designated are described. In some embodiments, methods and user interfaces for displaying a user interface that includes health topics, where information included in the user interface corresponds to a selected health topic, are described.

24 Claims, 25 Drawing Sheets

(51) Int. Cl.
*G06F 3/0482* (2013.01)
*G06F 3/0488* (2022.01)
*G16H 20/00* (2018.01)

(58) Field of Classification Search
USPC .......................................................... 705/2, 3
See application file for complete search history.

(56) References Cited

U.S. PATENT DOCUMENTS

2016/0239619 A1* 8/2016 Abou-Hawili ......... G06Q 50/22
2020/0143258 A1   5/2020 Kanner et al.
2020/0381091 A1  12/2020 Granvold et al.
2020/0381099 A1  12/2020 Crowley et al.

OTHER PUBLICATIONS

International Preliminary Report on Patentability received for PCT Patent Application No. PCT/US2022/030692, mailed on Dec. 21, 2023, 13 pages.
International Search Report and Written Opinion received for PCT Patent Application No. PCT/US2022/030692, mailed on Oct. 25, 2022, 19 pages.
Invitation to Pay Additional Fees and Partial International Search Report received for PCT Patent Application No. PCT/US2022/030692, mailed on Sep. 1, 2022, 10 pages.

* cited by examiner

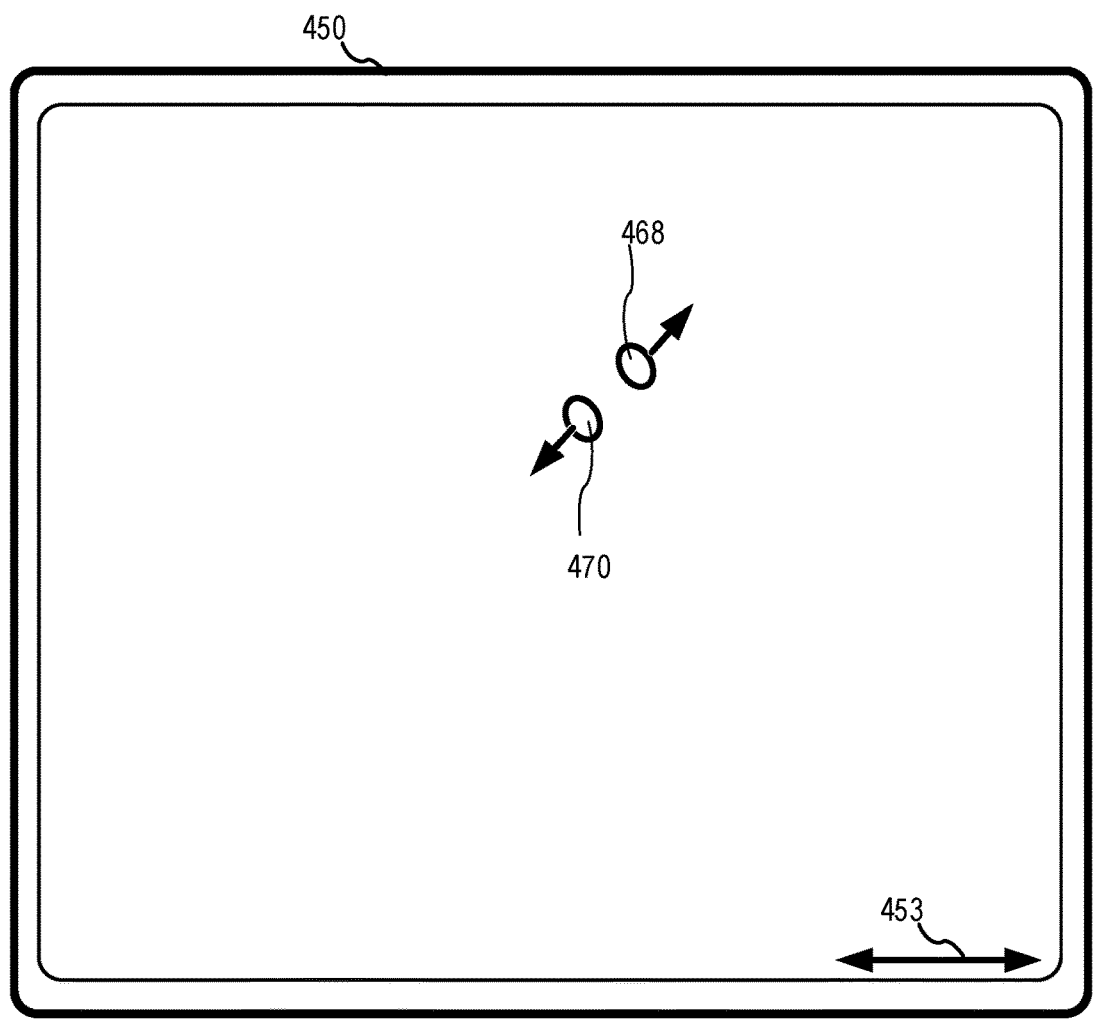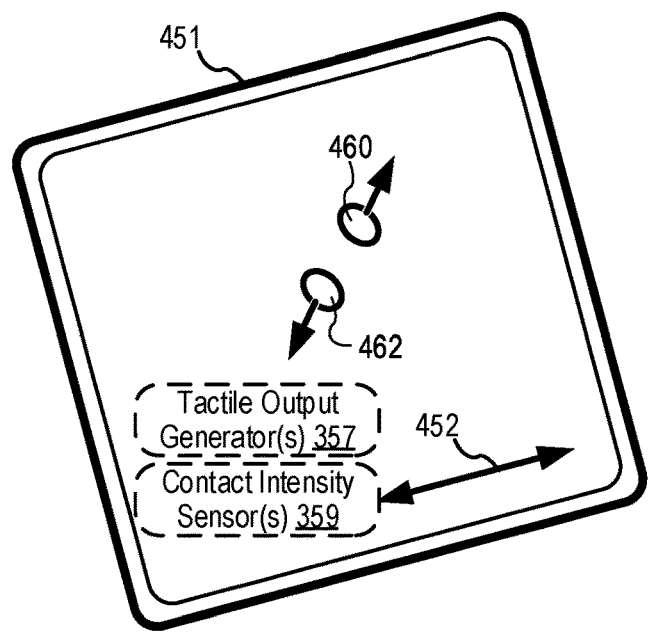
FIG. 4B

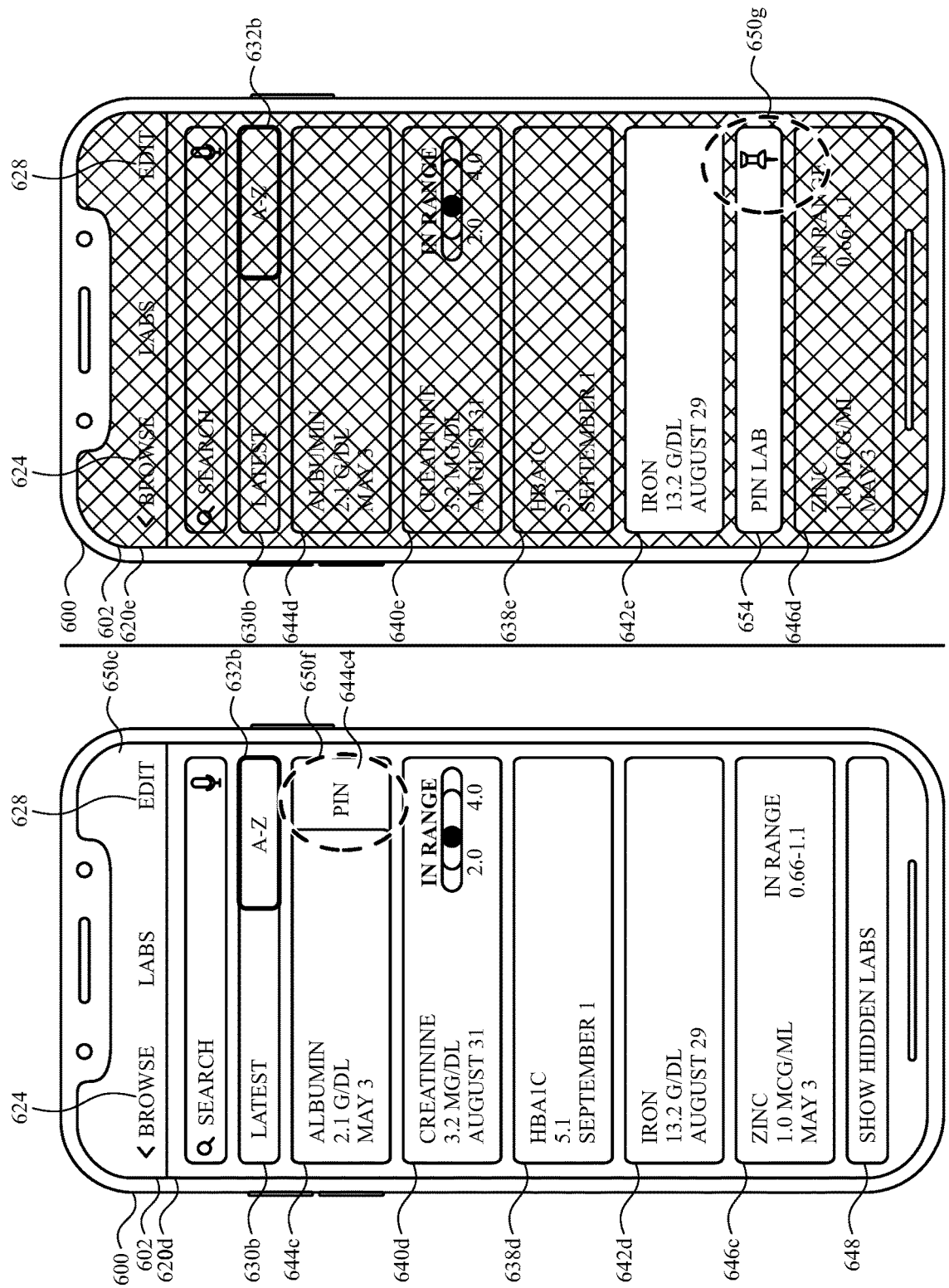

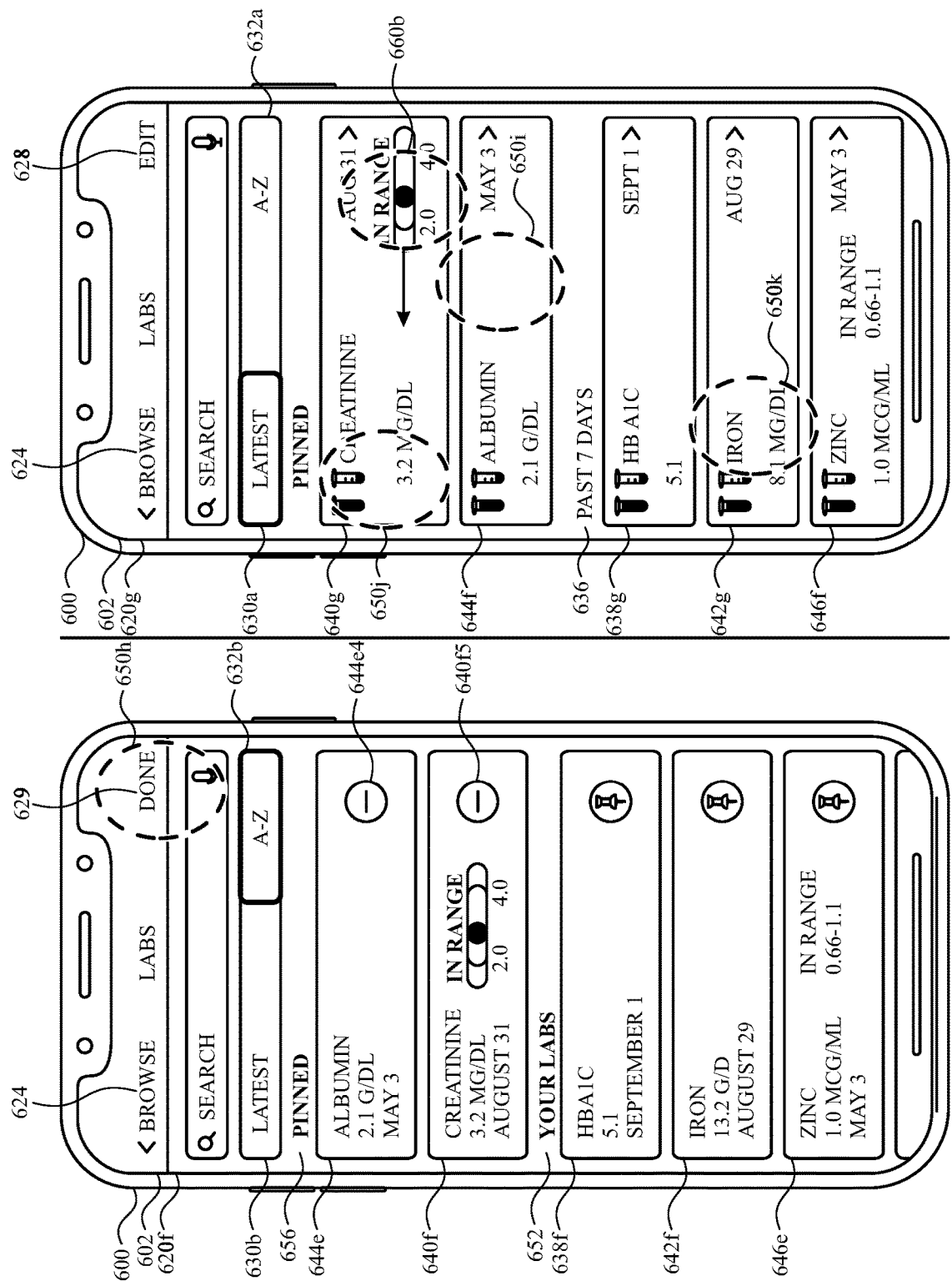

700

702
Displaying, via the display generation component, a first user interface that includes a user-interactive graphical user interface object corresponding to a first lab type, wherein:

704
In accordance with a determination that the first lab type has been designated via a user input received via the one or more input devices, the user-interactive graphical user interface object corresponding to the first lab type includes a graphical indication of a difference between a first value corresponding to the first lab type and at least a second value corresponding to the first lab type.

706
In accordance with a determination that the first lab type has not been designated via a user input, displaying, via the display generation component, the user-interactive graphical user interface object corresponding to the first lab type without a graphical indication of the difference between the first value corresponding to the first lab type and at least the second value corresponding to the first lab type.

*FIG. 7*

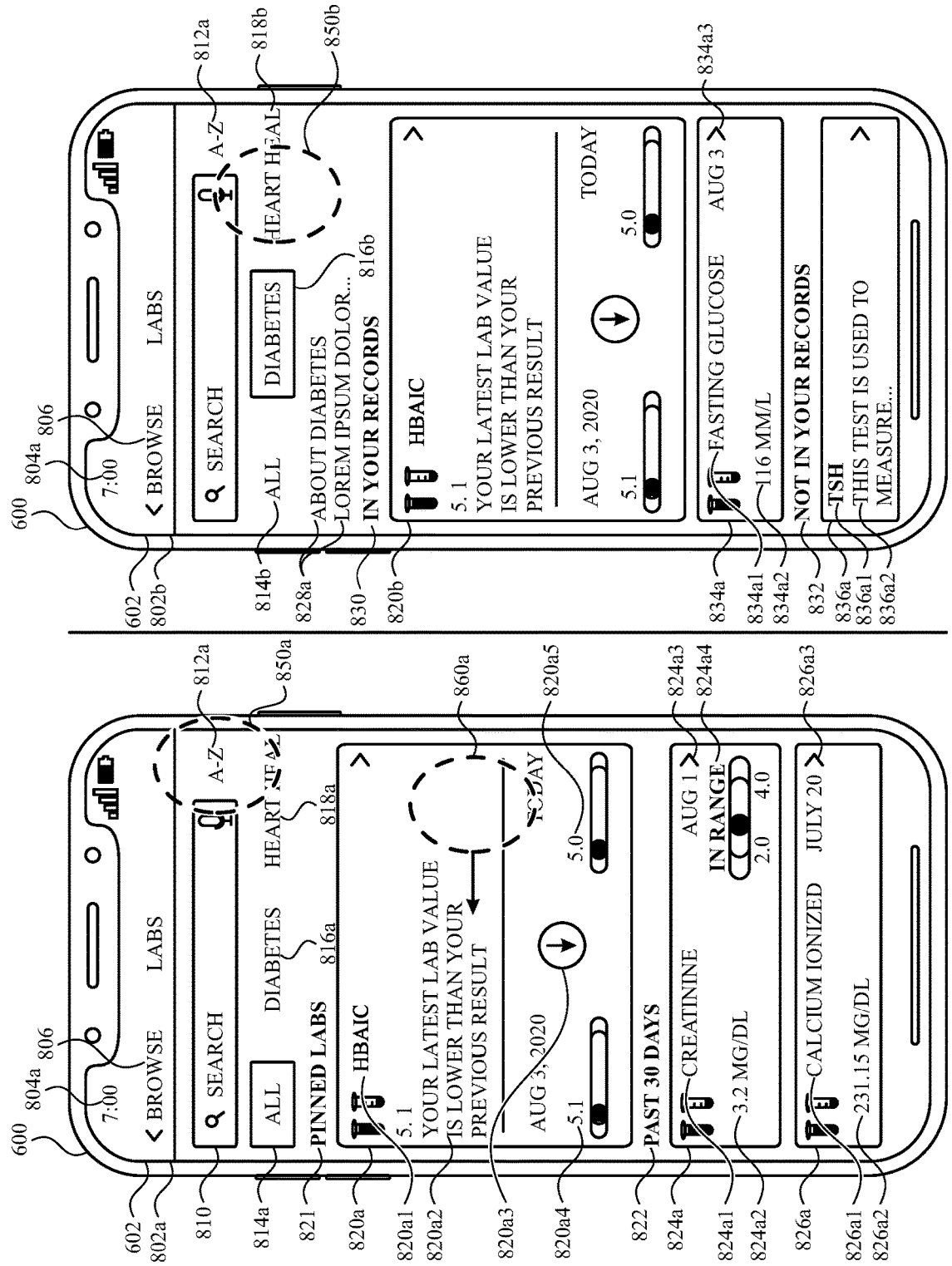

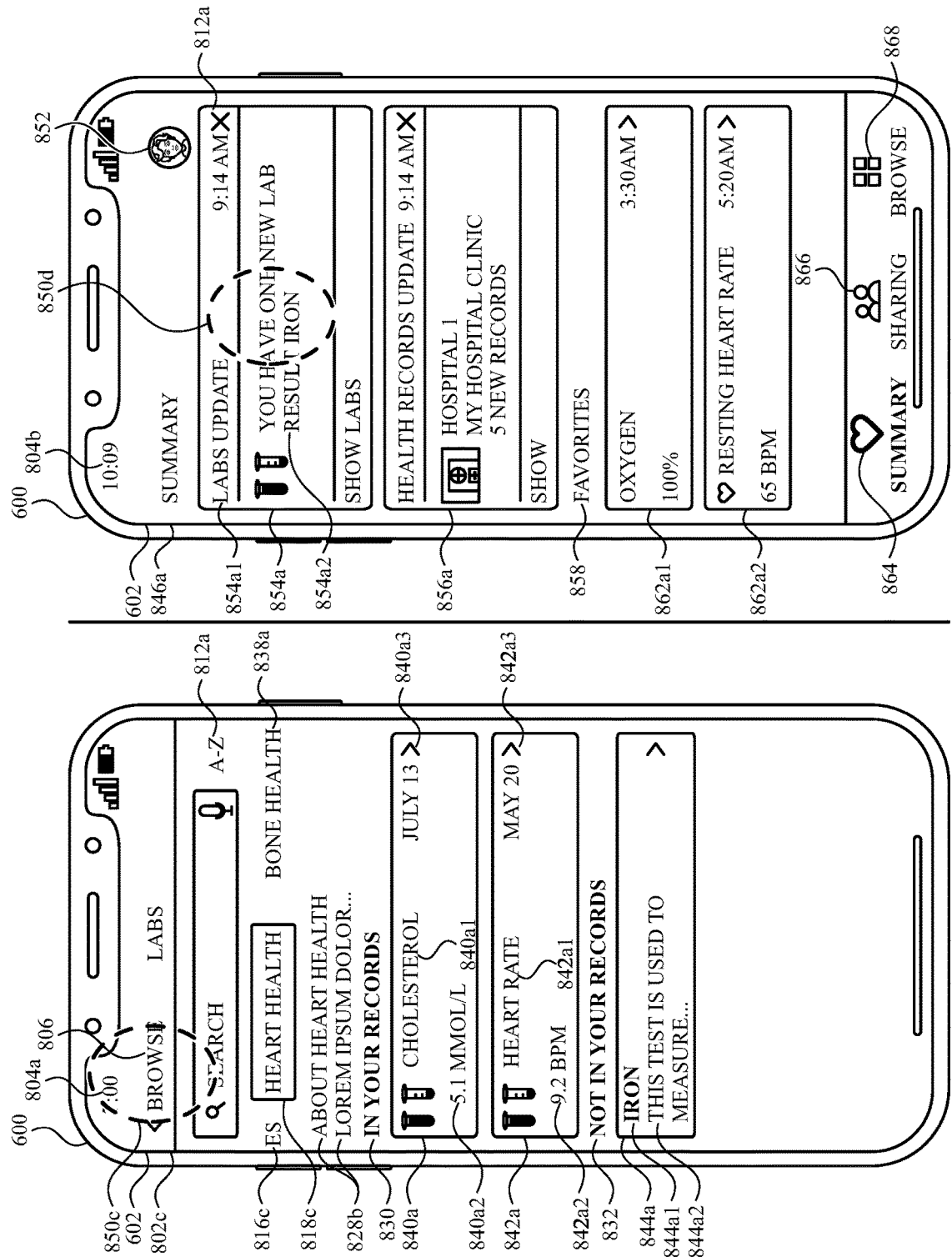

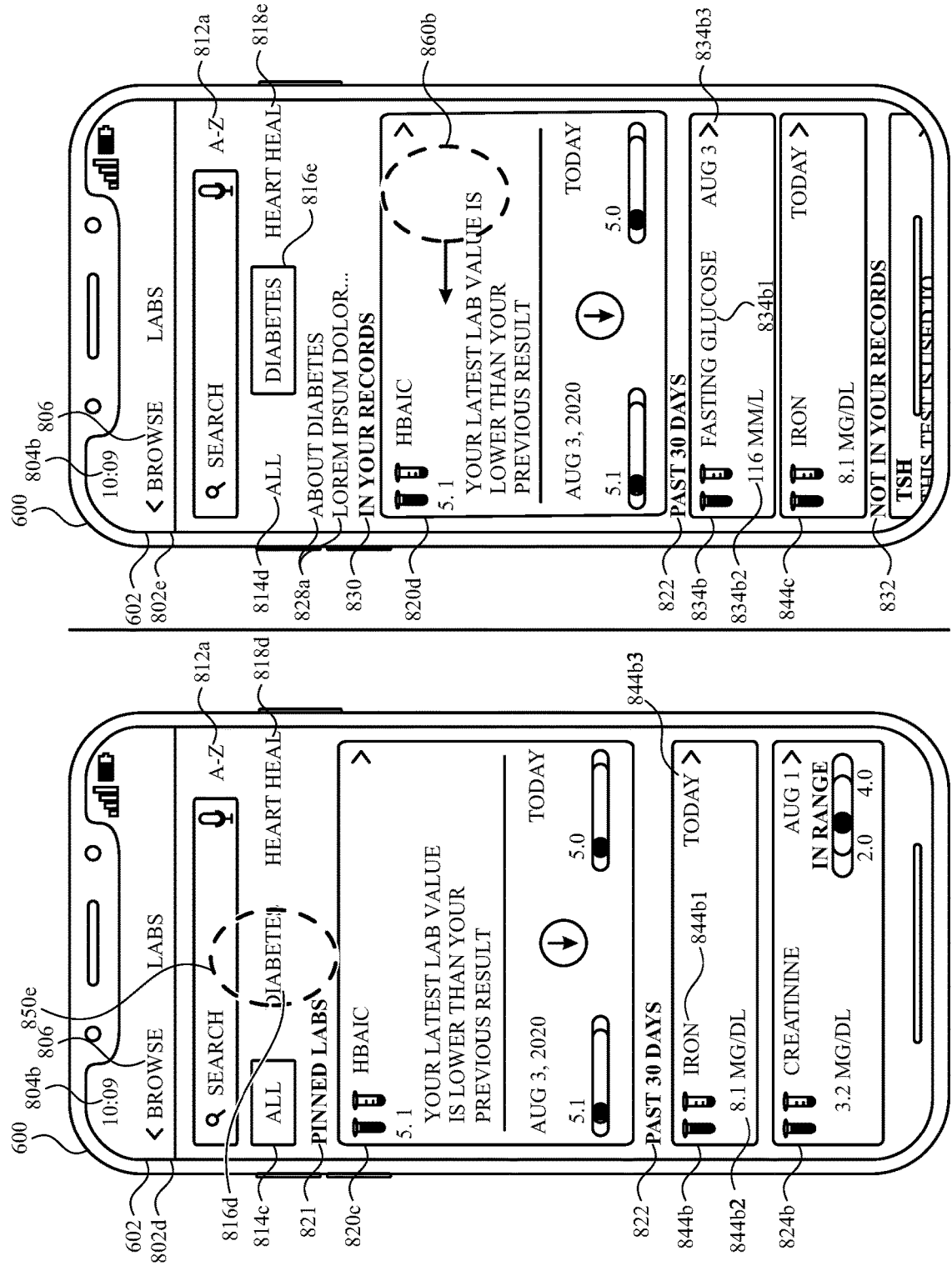

USER INTERFACES RELATED TO CLINICAL DATA

CROSS-REFERENCE TO RELATED APPLICATIONS

This application claims priority to U.S. Provisional patent application Ser. No. 63/197,422, entitled "USER INTERFACES RELATED TO CLINICAL DATA," filed on Jun. 6, 2021, the content of which is hereby incorporated by reference in its entirety.

FIELD

The present disclosure relates generally to computer user interfaces, and more specifically to techniques for displaying and managing user interfaces including information related to physiological measurements.

BACKGROUND

Personal electronic devices allow users to view information related to physiological measurements. Some personal electronic devices include the ability to display user interfaces related to physiological measurements.

BRIEF SUMMARY

Some techniques for displaying and managing user interfaces including information related to physiological measurements using electronic devices, however, are generally cumbersome and inefficient. For example, some existing techniques use a complex and time-consuming user interface, which may include multiple key presses or keystrokes, particularly when displaying information related to multiple physiological measurements. Existing techniques require more time than necessary, wasting user time and device energy. This latter consideration is particularly important in battery-operated devices.

Accordingly, the present technique provides electronic devices with faster, more efficient methods and interfaces for displaying and managing user interfaces including information related to physiological measurements. Such methods and interfaces optionally complement or replace other methods for displaying and managing user interfaces including information related to physiological measurements. Such methods and interfaces reduce the cognitive burden on a user and produce a more efficient human-machine interface. For battery-operated computing devices, such methods and interfaces conserve power and increase the time between battery charges.

In accordance with some embodiments, a method performed at a computer system that is in communication with a display generation component and one or more input devices is described. The method comprises: displaying, via the display generation component, a first user interface that includes a user-interactive graphical user interface object corresponding to a first lab type, wherein: in accordance with a determination that the first lab type has been designated via a user input received via the one or more input devices, the user-interactive graphical user interface object corresponding to the first lab type includes a graphical indication of a difference between a first value corresponding to the first lab type and at least a second value corresponding to the first lab type; and in accordance with a determination that the first lab type has not been designated via a user input, displaying, via the display generation component, the user-interactive graphical user interface object corresponding to the first lab type without a graphical indication of the difference between the first value corresponding to the first lab type and at least the second value corresponding to the first lab type.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, a first user interface that includes a user-interactive graphical user interface object corresponding to a first lab type, wherein: in accordance with a determination that the first lab type has been designated via a user input received via the one or more input devices, the user-interactive graphical user interface object corresponding to the first lab type includes a graphical indication of a difference between a first value corresponding to the first lab type and at least a second value corresponding to the first lab type; and in accordance with a determination that the first lab type has not been designated via a user input, displaying, via the display generation component, the user-interactive graphical user interface object corresponding to the first lab type without a graphical indication of the difference between the first value corresponding to the first lab type and at least the second value corresponding to the first lab type.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, a first user interface that includes a user-interactive graphical user interface object corresponding to a first lab type, wherein: in accordance with a determination that the first lab type has been designated via a user input received via the one or more input devices, the user-interactive graphical user interface object corresponding to the first lab type includes a graphical indication of a difference between a first value corresponding to the first lab type and at least a second value corresponding to the first lab type; and in accordance with a determination that the first lab type has not been designated via a user input, displaying, via the display generation component, the user-interactive graphical user interface object corresponding to the first lab type without a graphical indication of the difference between the first value corresponding to the first lab type and at least the second value corresponding to the first lab type.

In accordance with some embodiments, a computer system that is configured to communicate with a display generation component and one or more input devices is described. The computer system comprises: one or more processors; and memory storing one or more programs configured to be executed by the one or more processors, the one or more programs including instructions for: displaying, via the display generation component, a first user interface that includes a user-interactive graphical user interface object corresponding to a first lab type, wherein: in accordance with a determination that the first lab type has been designated via a user input received via the one or more input devices, the user-interactive graphical user interface object corresponding to the first lab type includes a graphical indication of a difference between a first value corresponding to the first lab type and at least a second value corresponding to the first lab type; and in accordance with a determination that the first lab type has not been designated via a user input, displaying, via the display generation component, the user-interactive graphical user interface object corresponding to the first lab type without a graphical indication of the difference between the first value corresponding to the first lab type and at least the second value corresponding to the first lab type.

In accordance with some embodiments, a computer system that is configured to communicate with a display generation component and one or more input devices is described. The computer system comprises: means for displaying, via the display generation component, a first user interface that includes a user-interactive graphical user interface object corresponding to a first lab type, wherein: in accordance with a determination that the first lab type has been designated via a user input received via the one or more input devices, the user-interactive graphical user interface object corresponding to the first lab type includes a graphical indication of a difference between a first value corresponding to the first lab type and at least a second value corresponding to the first lab type; and in accordance with a determination that the first lab type has not been designated via a user input, displaying, via the display generation component, the user-interactive graphical user interface object corresponding to the first lab type without a graphical indication of the difference between the first value corresponding to the first lab type and at least the second value corresponding to the first lab type.

In accordance with some embodiments, a computer program product is described. The computer program product comprises one or more programs configured to be executed by one or more processors of a computer system that is in communication with a display generation component and one or more input devices. The one or more programs include instructions for: displaying, via the display generation component, a first user interface that includes a user-interactive graphical user interface object corresponding to a first lab type, wherein: in accordance with a determination that the first lab type has been designated via a user input received via the one or more input devices, the user-interactive graphical user interface object corresponding to the first lab type includes a graphical indication of a difference between a first value corresponding to the first lab type and at least a second value corresponding to the first lab type; and in accordance with a determination that the first lab type has not been designated via a user input, displaying, via the display generation component, the user-interactive graphical user interface object corresponding to the first lab type without a graphical indication of the difference between the first value corresponding to the first lab type and at least the second value corresponding to the first lab type.

In accordance with some embodiments, a method performed at a computer system that is in communication with a display generation component and one or more input devices is described. The method comprises: receiving, at the computer system, a set of clinical data that includes: a set of data instances that correspond to a first health topic, and a set of data instances that correspond to a second health topic, different than the first health topic; displaying, via the display generation component, a clinical data user interface that includes: a first user-interactive graphical user interface object that corresponds to the first health topic; a second user-interactive graphical user interface object that corresponds to the second health topic; and a set of data instance graphical user interface objects, wherein: in accordance with a determination that the first user-interactive graphical user interface object is currently selected, the set of data instance graphical user interface objects corresponds to the set of data instances that correspond to the first health topic; and in accordance with a determination that the second user-interactive graphical user interface object is currently selected, the set of data instance graphical user interface objects corresponds to the set of data instances that correspond to the second health topic.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: receiving, at the computer system, a set of clinical data that includes: a set of data instances that correspond to a first health topic, and a set of data instances that correspond to a second health topic, different than the first health topic; displaying, via the display generation component, a clinical data user interface that includes: a first user-interactive graphical user interface object that corresponds to the first health topic; a second user-interactive graphical user interface object that corresponds to the second health topic; and a set of data instance graphical user interface objects, wherein: in accordance with a determination that the first user-interactive graphical user interface object is currently selected, the set of data instance graphical user interface objects corresponds to the set of data instances that correspond to the first health topic; and in accordance with a determination that the second user-interactive graphical user interface object is currently selected, the set of data instance graphical user interface objects corresponds to the set of data instances that correspond to the second health topic.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: receiving, at the computer system, a set of clinical data that includes: a set of data instances that correspond to a first health topic, and a set of data instances that correspond to a second health topic, different than the first health topic; displaying, via the display generation component, a clinical data user interface that includes: a first user-interactive graphical user interface object that corresponds to the first health topic; a second user-interactive graphical user interface object that corresponds to the second health topic; and a set of data instance graphical user interface objects, wherein: in accordance with a determination that the first user-interactive graphical user interface object is currently selected, the set of data instance graphical user interface objects corresponds to the set of data instances that correspond to the first health topic; and in accordance with a determination that the second user-interactive graphical user interface object is currently selected, the set of data instance graphical user interface objects corresponds to the set of data instances that correspond to the second health topic.

In accordance with some embodiments, a computer system that is configured to communicate with a display generation component and one or more input devices is described. The computer system comprises: one or more processors; and memory storing one or more programs configured to be executed by the one or more processors, the one or more programs including instructions for: receiving, at the computer system, a set of clinical data that includes: a set of data instances that correspond to a first health topic, and a set of data instances that correspond to a second health topic, different than the first health topic; displaying, via the display generation component, a clinical data user interface that includes: a first user-interactive graphical user interface object that corresponds to the first health topic; a second user-interactive graphical user interface object that corresponds to the second health topic; and a set of data instance graphical user interface objects, wherein: in accordance with a determination that the first user-interactive graphical user interface object is currently selected, the set of data instance graphical user interface objects corresponds to the set of data instances that correspond to the first health topic; and in accordance with a determination that the second user-interactive graphical user interface object is currently selected, the set of data instance graphical user interface objects corresponds to the set of data instances that correspond to the second health topic.

In accordance with some embodiments, a computer system that is configured to communicate with a display generation component and one or more input devices is described. The computer system comprises: means for receiving, at the computer system, a set of clinical data that includes: a set of data instances that correspond to a first health topic, and a set of data instances that correspond to a second health topic, different than the first health topic; means for displaying, via the display generation component, a clinical data user interface that includes: a first user-interactive graphical user interface object that corresponds to the first health topic; a second user-interactive graphical user interface object that corresponds to the second health topic; and a set of data instance graphical user interface objects, wherein: in accordance with a determination that the first user-interactive graphical user interface object is currently selected, the set of data instance graphical user interface objects corresponds to the set of data instances that correspond to the first health topic; and in accordance with a determination that the second user-interactive graphical user interface object is currently selected, the set of data instance graphical user interface objects corresponds to the set of data instances that correspond to the second health topic.

In accordance with some embodiments, a computer program product is described. The computer program product comprises one or more programs configured to be executed by one or more processors of a computer system that is in communication with a display generation component and one or more input devices. The one or more programs include instructions for: receiving, at the computer system, a set of clinical data that includes: a set of data instances that correspond to a first health topic, and a set of data instances that correspond to a second health topic, different than the first health topic; displaying, via the display generation component, a clinical data user interface that includes: a first user-interactive graphical user interface object that corresponds to the first health topic; a second user-interactive graphical user interface object that corresponds to the second health topic; and a set of data instance graphical user interface objects, wherein: in accordance with a determination that the first user-interactive graphical user interface object is currently selected, the set of data instance graphical user interface objects corresponds to the set of data instances that correspond to the first health topic; and in accordance with a determination that the second user-interactive graphi-cal user interface object is currently selected, the set of data instance graphical user interface objects corresponds to the set of data instances that correspond to the second health topic.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for displaying and managing user interfaces including information related to physiological measurements, thereby increasing the effectiveness, efficiency, and user satisfaction with such devices. Such methods and interfaces may complement or replace other methods for displaying and managing user interfaces including information related to physiological measurements.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIG. 7 is a flow diagram illustrating a method for displaying lab types based on their designation status using a computer system in accordance with some embodiments.

FIGS. 8A-8I illustrate exemplary user interfaces for displaying health topics.

DESCRIPTION OF EMBODIMENTS

Figure 1A:
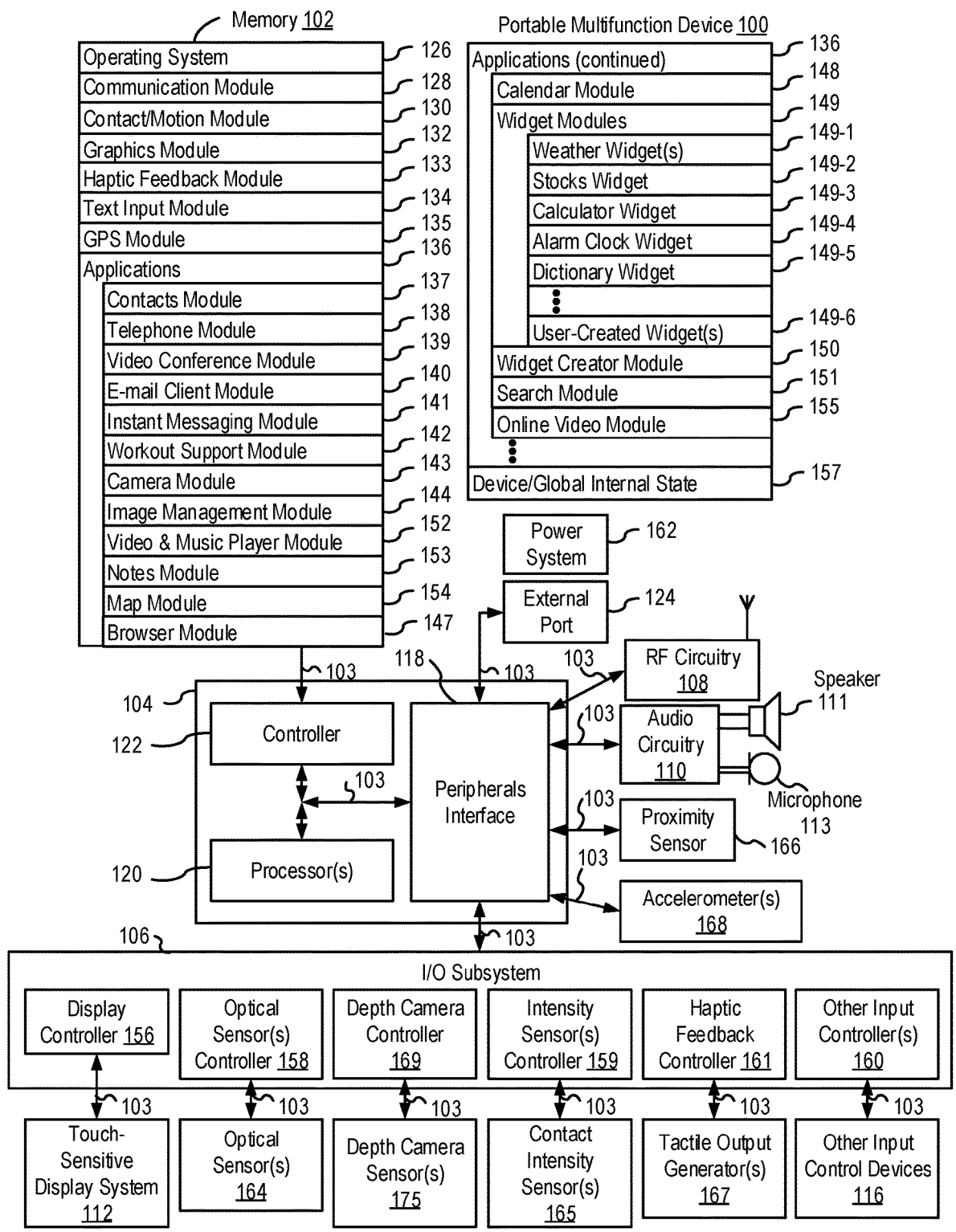
FIG. 1A is a block diagram illustrating a portable multifunction device with a touch-sensitive display in accordance with some embodiments.

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for displaying and managing user interfaces including information related to physiological measurements. For example, there is a need for displaying lab types based on their designation status. For another example, there is a need for devices that enable an intuitive and efficient method for displaying health topics. Such techniques can reduce the cognitive burden on a user who reviews various lab types regularly, thereby enhancing productivity. Further, such techniques can reduce processor and battery power otherwise wasted on redundant user inputs.

Below, FIGS. 1A-1B, 2, 3, 4A-4B, and 5A-5B provide a description of exemplary devices for performing the techniques for managing event notifications. FIGS. 6A-6N illustrate exemplary user interfaces for displaying lab types based on their designation status. FIG. 7 is a flow diagram illustrating methods for displaying lab types based on their designation status in accordance with some embodiments. The user interfaces in FIGS. 6A-6N are used to illustrate the processes described below, including the processes in FIG. 7. FIGS. 8A-8I illustrate exemplary user interfaces for displaying health topics. FIG. 9 is a flow diagram illustrating methods of displaying health topics in accordance with some embodiments. The user interfaces in FIGS. 8A-8I are used to illustrate the processes described below, including the processes in FIG. 9.

The processes described below enhance the operability of the devices and make the user-device interfaces more efficient (e.g., by helping the user to provide proper inputs and reducing user mistakes when operating/interacting with the device) through various techniques, including by providing improved visual feedback to the user, reducing the number of inputs needed to perform an operation, providing additional control options without cluttering the user interface with additional displayed controls, performing an operation when a set of conditions has been met without requiring further user input, and/or additional techniques. These techniques also reduce power usage and improve battery life of the device by enabling the user to use the device more quickly and efficiently.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. In some embodiments, these terms are only used to distinguish one element from another. For example, a first touch could be termed a second touch, and, similarly, a second touch could be termed a first touch, without departing from the scope of the various described embodiments. In some embodiments, the first touch and the second touch are two separate references to the same touch. In some embodiments, the first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures and/or air gestures) as input. In some embodiments, the one or more input devices are integrated with the computer system. In some embodiments, the one or more input devices are separate from the computer system. In some embodiments, an air gesture is a gesture that is detected without the user touching an input element that is part of the device (or independently of an input element that is a part of the device) and is based on detected motion of a portion of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. Patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
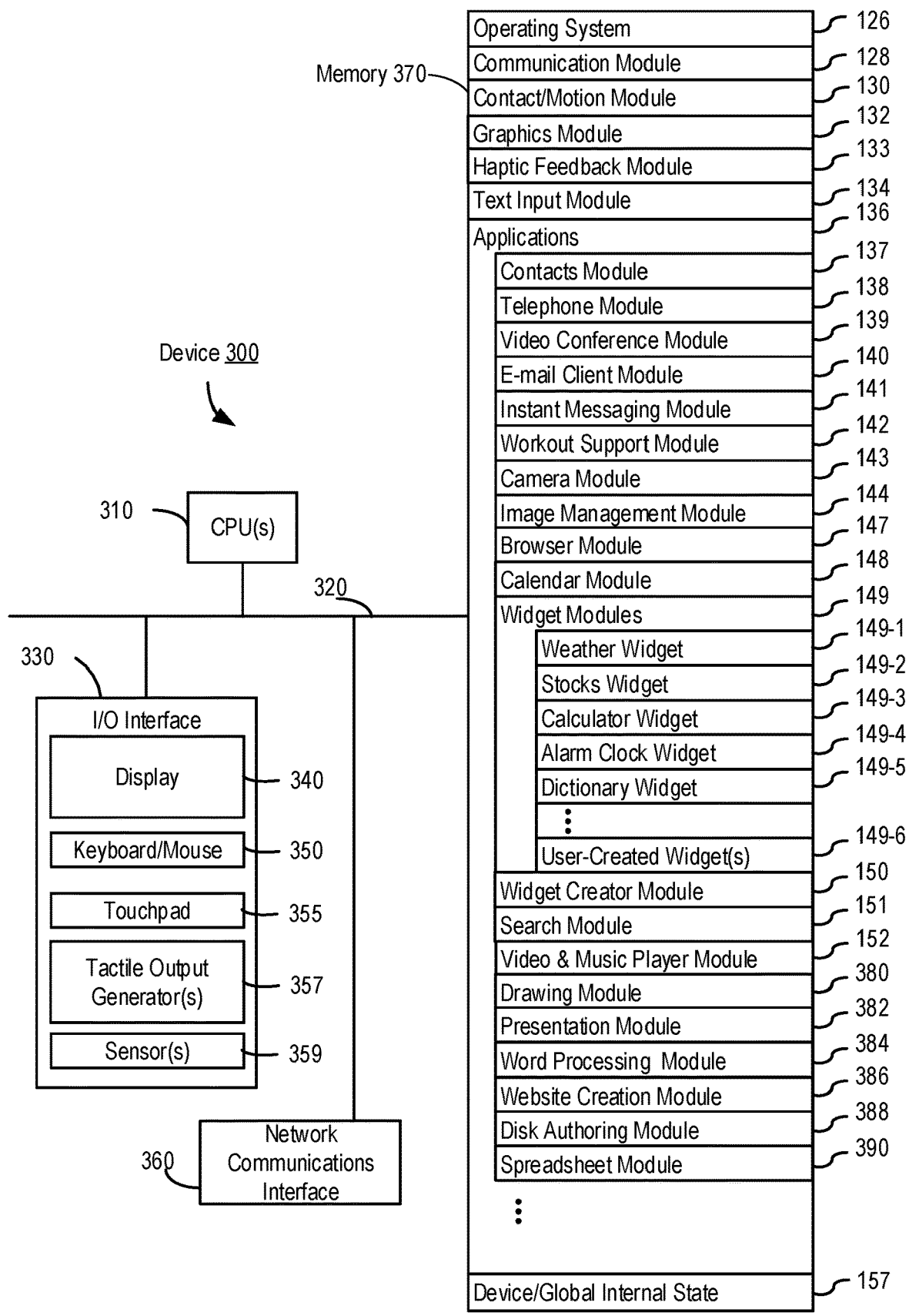
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts module 137, e-mail module 140, IM module 141, browser module 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone module 138, video conference module 139, e-mail module 140, or IM module 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
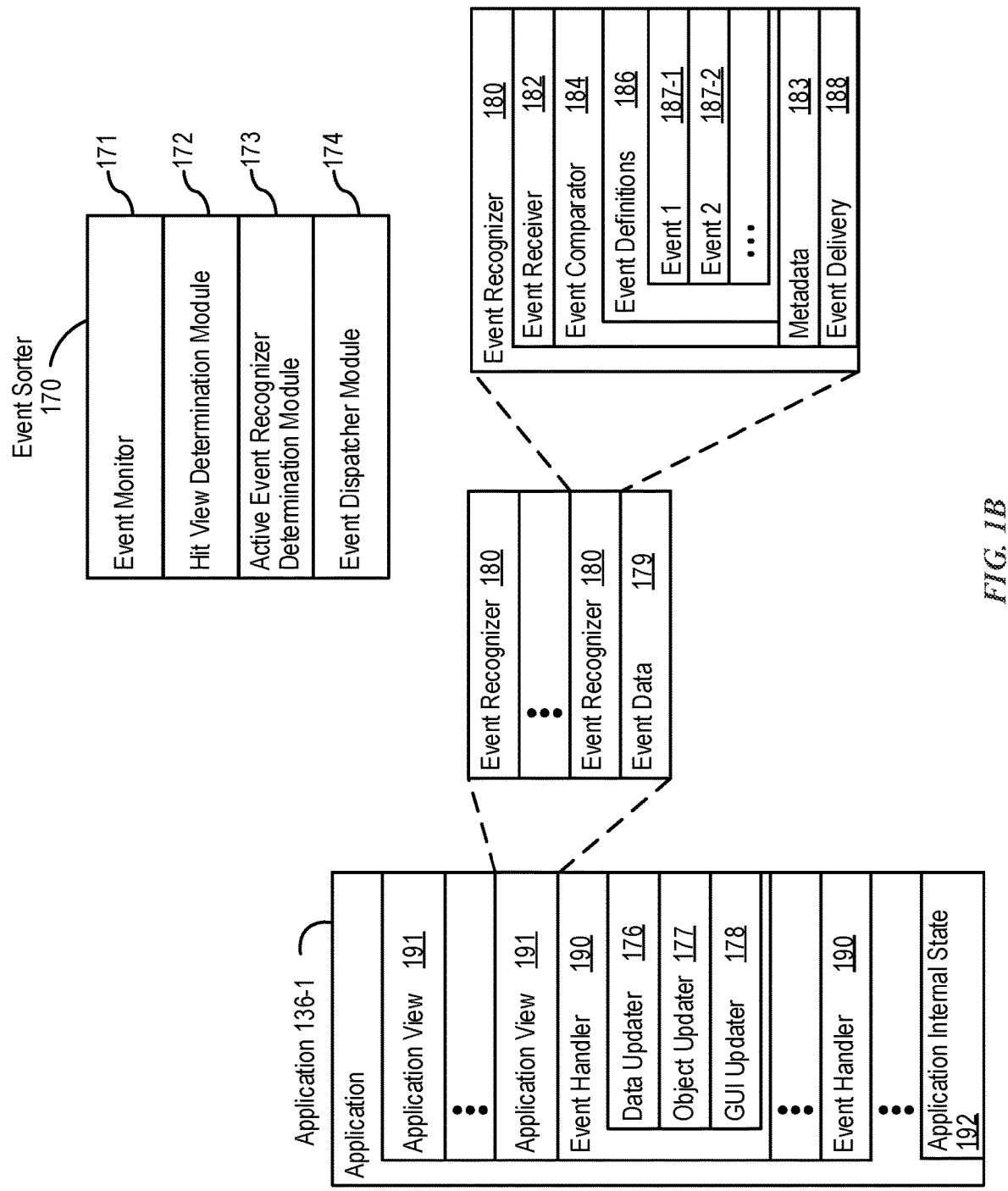
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
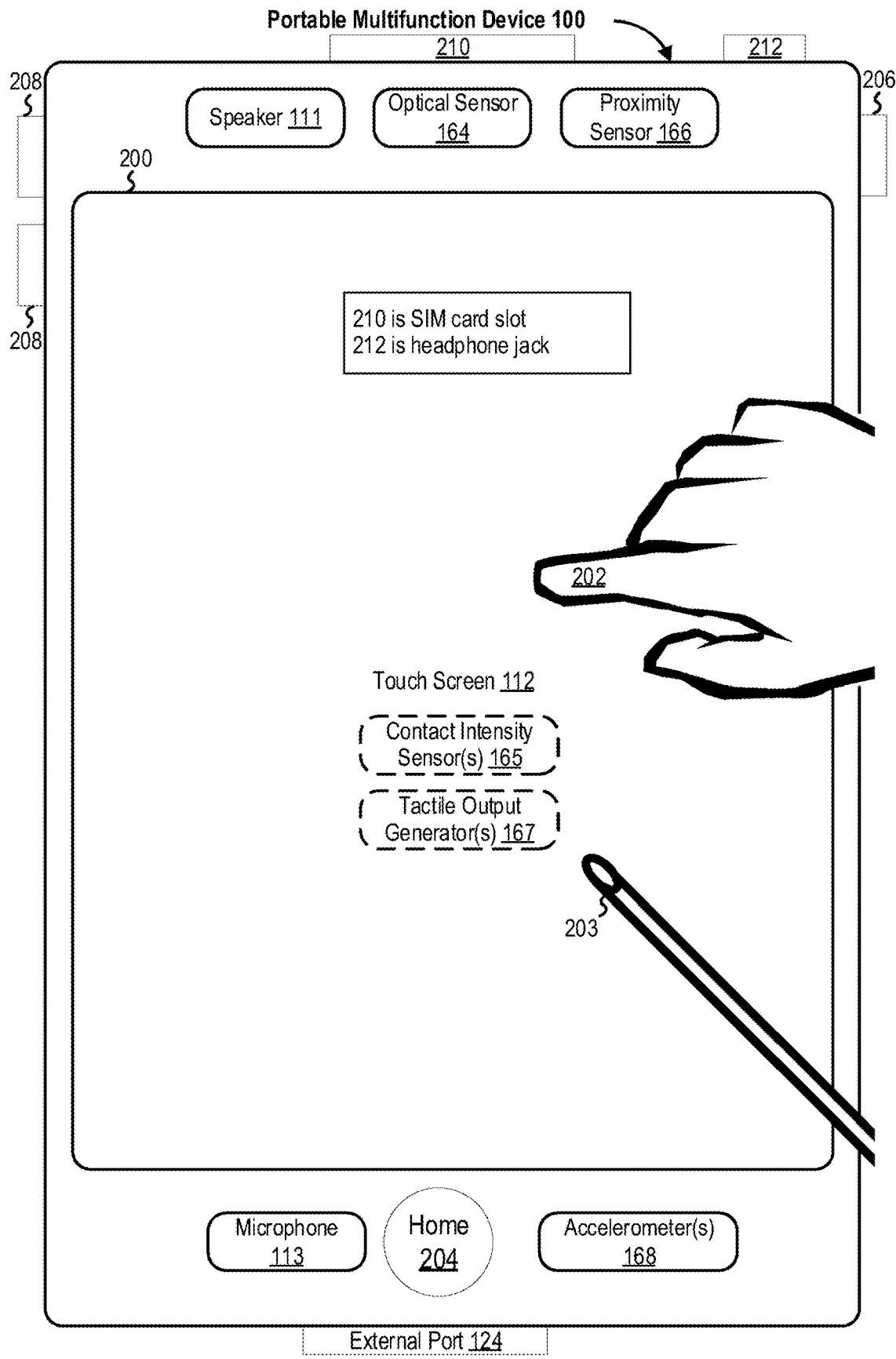
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
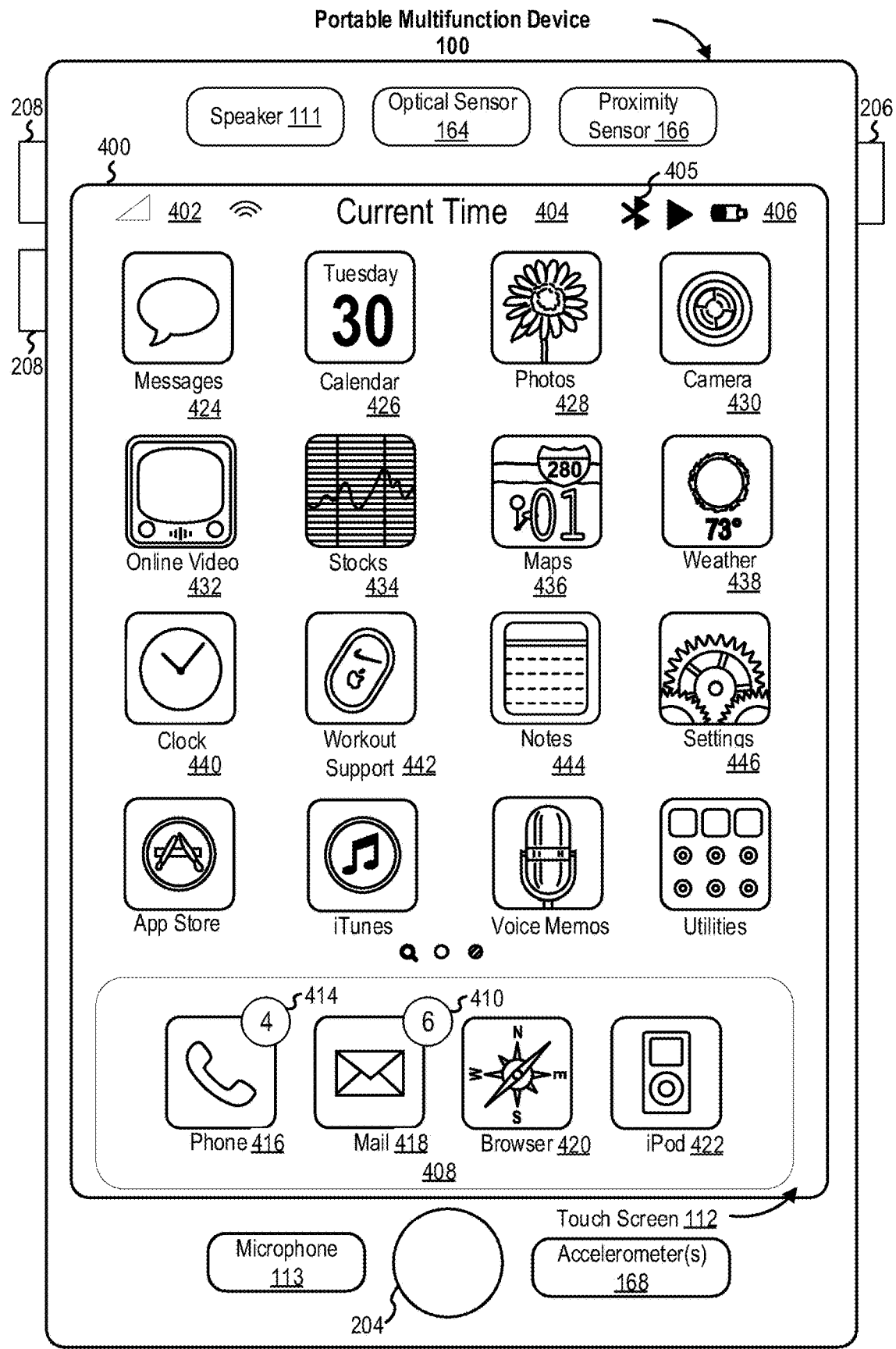
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
   Icon 416 for telephone module 138, labeled "Phone," which optionally includes an indicator 414 of the number of missed calls or voicemail messages;
   Icon 418 for e-mail client module 140, labeled "Mail," which optionally includes an indicator 410 of the number of unread e-mails;
   Icon 420 for browser module 147, labeled "Browser;" and
   Icon 422 for video and music player module 152, also referred to as iPod (trademark of Apple Inc.) module 152, labeled "iPod;" and
Icons for other applications, such as:
   Icon 424 for IM module 141, labeled "Messages;"
   Icon 426 for calendar module 148, labeled "Calendar;"
   Icon 428 for image management module 144, labeled "Photos;"
   Icon 430 for camera module 143, labeled "Camera;"
   Icon 432 for online video module 155, labeled "Online Video;"
   Icon 434 for stocks widget 149-2, labeled "Stocks;"
   Icon 436 for map module 154, labeled "Maps;"
   Icon 438 for weather widget 149-1, labeled "Weather;"
   Icon 440 for alarm clock widget 149-4, labeled "Clock;"
   Icon 442 for workout support module 142, labeled "Workout Support;"
   Icon 444 for notes module 153, labeled "Notes;" and
   Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
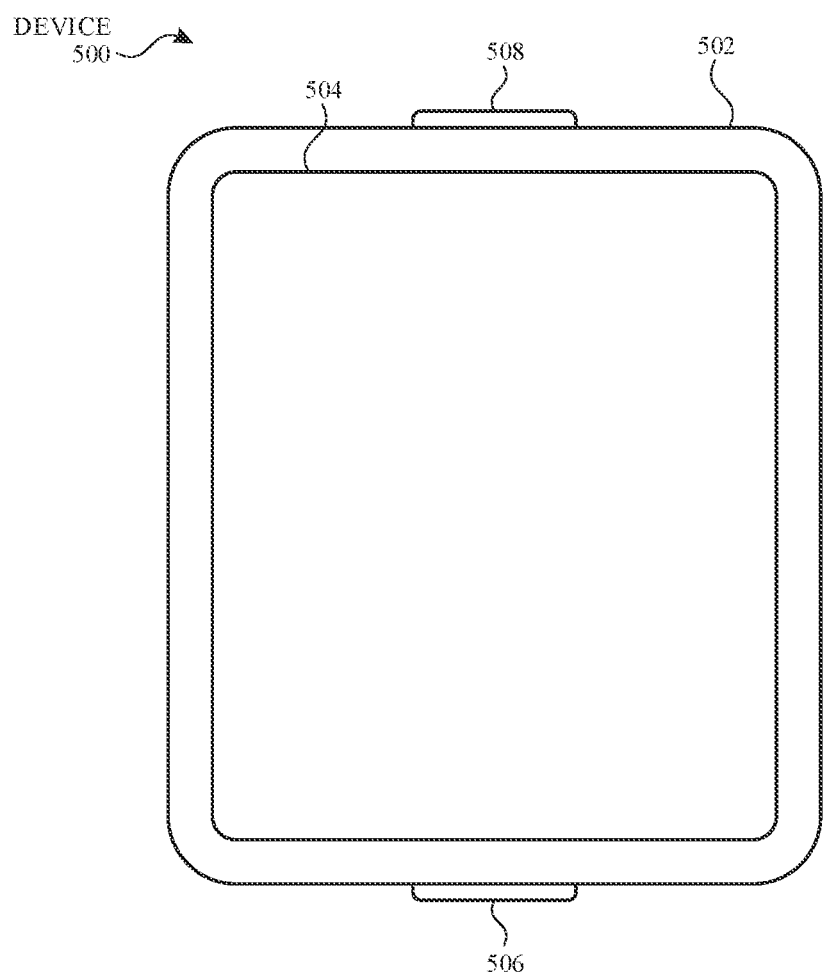
FIG. 5A illustrates a personal electronic device in accordance with some embodiments.
Figures 6A, 6B:
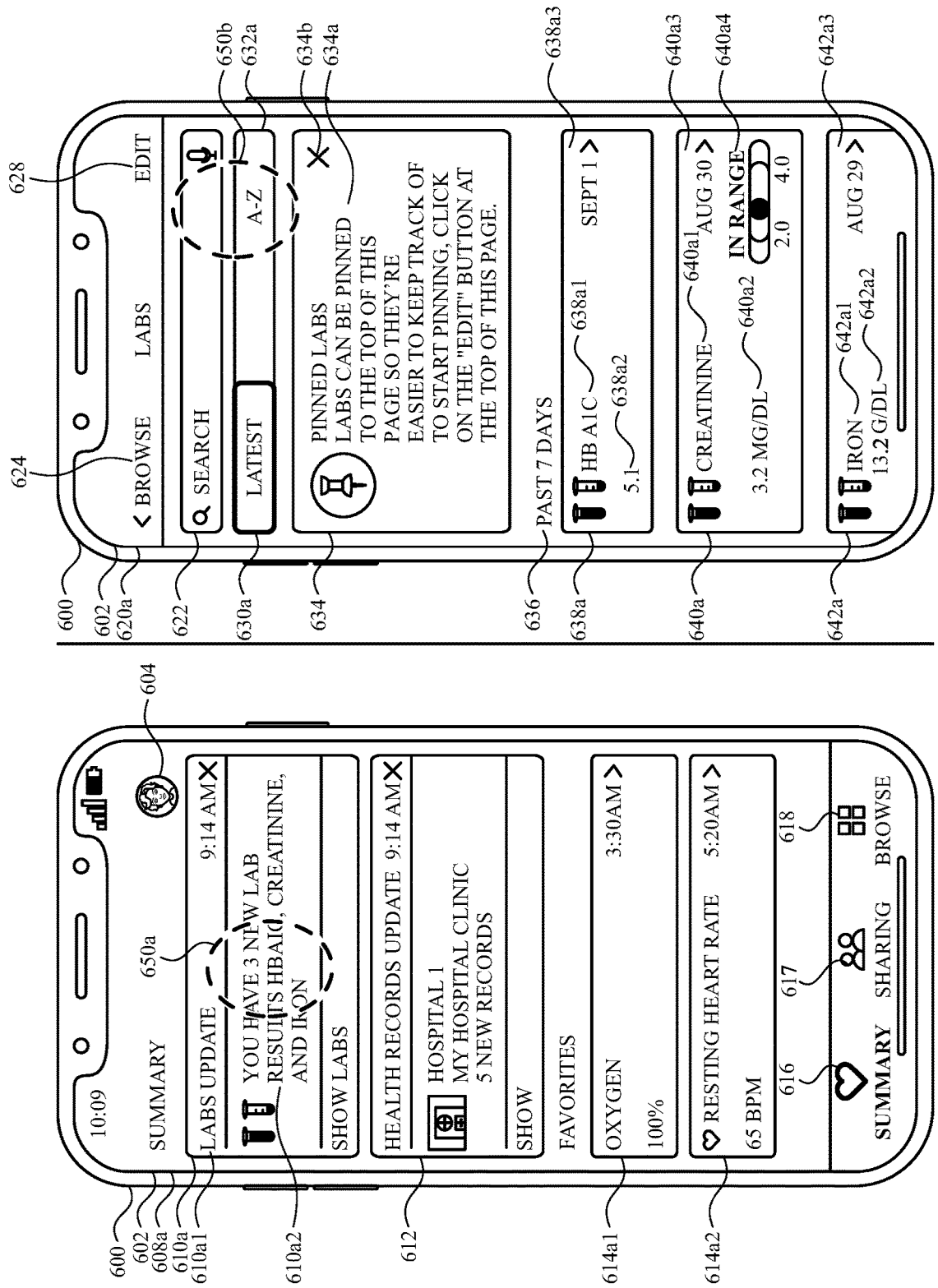
FIGS. 6A-6N illustrate exemplary user interfaces for displaying lab types based on their designation status.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
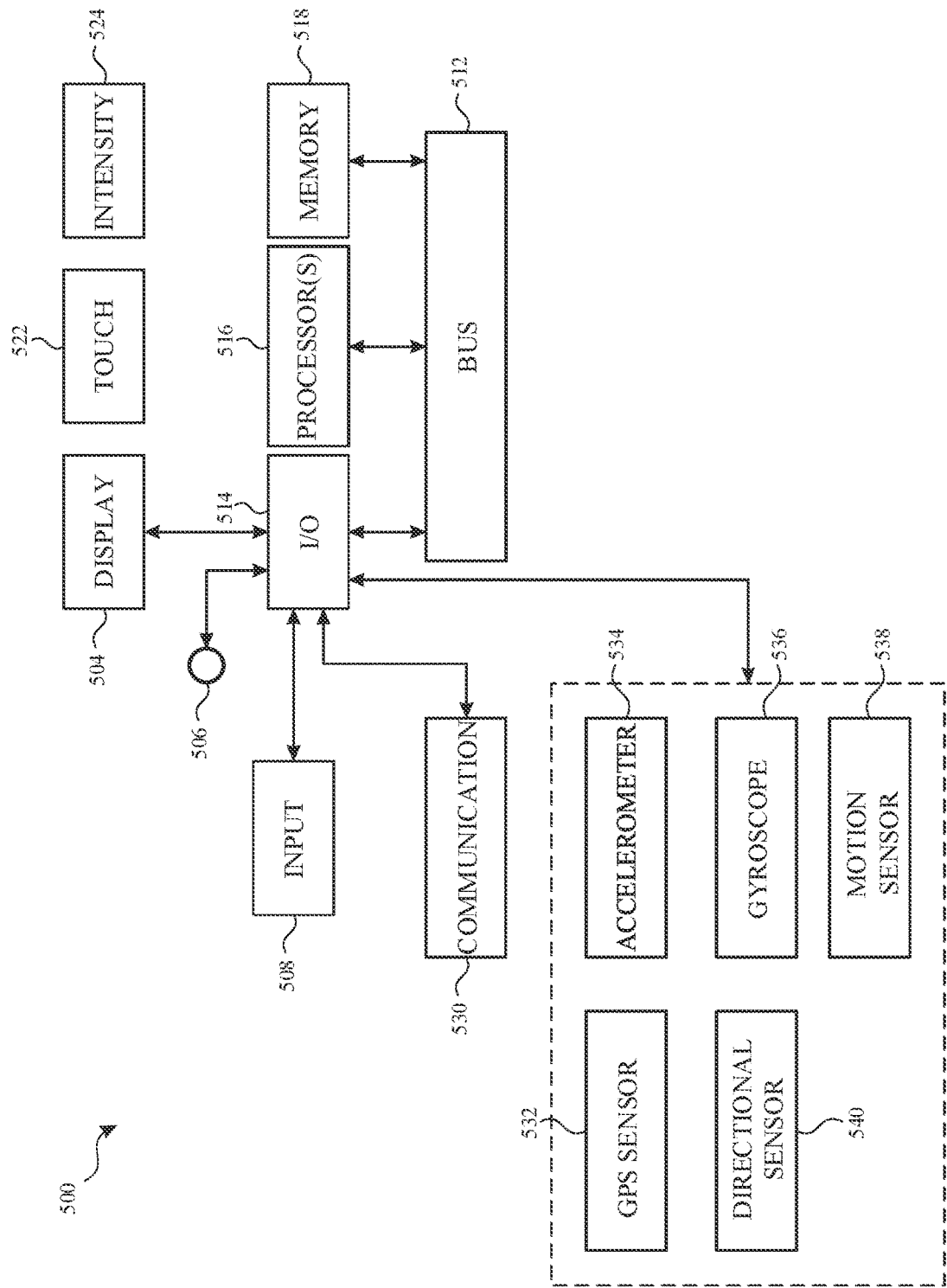
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 and 900 (FIGS. 7 and 9). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Attention is now directed towards embodiments of user interfaces ("UI") and associated processes that are implemented on an electronic device, such as portable multifunction device 100, device 300, or device 500.

FIGS. 6A-6N illustrate exemplary user interfaces for displaying lab types based on their designation status, in accordance with some embodiments. The user interfaces in these figures are used to illustrate the processes described below, including the processes in FIG. 7.

FIG. 6A illustrates computer 600 displaying summary user interface 608a via display 602. In some embodiments, computer system 600 optionally includes one or more features of device 100, device 300, or device 500. In some embodiments, computer system 600 is a tablet, phone, laptop, desktop, camera, etc. In some embodiments, the inputs described below can optionally be substituted for alternate inputs, such as a swipe input and/or a long press input.

Summary user interface 608a includes relevant information about health-related data, wherein the contents of summary user interface 608a depend on the designation status of various lab types. FIG. 6A illustrates a summary user interface that does not include any lab affordances or information related to specific labs and, in particular, does not include a lab affordance that has a graphical indication comparing two values corresponding to a particular lab type. In contrast, in FIG. 6M, described below, computer system 600 displays summary user interface 608b, which includes a graphical indicator of the difference between two labs values corresponding to a pinned lab type. Summary user interface 608a includes labs update user interface object 610a. Lab update user interface object 610a has update user interface object 610a1, which shows updates to labs. This user interface object may contain a visual and/or textual indicator that a data update for labs is available. Labs update user interface object 610a further includes update description 610a2 about the content of the labs data update.

Summary user interface 608a further includes health records update section 612, which provides information that a health records update is available. Summary user interface 608a can further include measurements (e.g., measurement 614a1 and measurement 614a2) that describe different measurements of health-related information. Summary user interface 608a further includes summary affordance 616 which, when selected while the summary user interface is not displayed, causes computer system 600 to display a summary user interface (e.g., 608a). At FIG. 6A, summary affordance 616 is displayed with a visually distinct appearance (e.g., bolded, outlined, and/or highlighted) to indicate that a summary user interface is currently being displayed and/or that summary affordance 616 is currently selected and/or active. Summary user interface 608a further includes sharing affordance 617 which, when selected, causes computer system 600 to display a user interface for sharing and/or transmitting information related to health data to other users. Summary user interface 608a further includes browse affordance 618 which, when selected, causes computer system 600 to display a user interface for browsing health-related information. Summary user interface 608a further includes avatar 604, which includes a graphical indicator corresponding to a user and/or a user account associated with computer system 600.

At FIG. 6A, computer system 600 receives input 650a (e.g., a tap input) on labs update user interface object 610a. In response to receiving input 650a, computer system 600 displays labs user interface 620a, as illustrated in FIG. 6B.

FIG. 6B illustrates computer system 600 displaying labs user interface 620a. Labs user interface 620a includes lab affordances corresponding to various lab types. Labs user interface 620a further includes edit affordance 628 which, when selected, causes computer system 600 to display a user interface for editing aspects of the labs data included in labs user interface 620a (e.g., to select which lab types are pinned to the top of the section (e.g., designated via a user input)), as illustrated below in FIG. 6D. Labs user interface 620a includes back affordance 624 which, when selected, causes computer system 600 to display a previously displayed user interface screen (e.g., summary user interface 608a). Labs user interface 620a further includes search bar 622 which, when selected, causes computer 600 to display options for searching among the labs data that can be displayed in labs user interface 620a (e.g., by inputting letters corresponding to lab data via a touch keyboard, via voice inputs received via a microphone).

Labs user interface 620a further includes latest sort option 630a, which, when selected, causes computer system 600 to display labs data included in labs user interface 620a based at least partially on chronology-based information (e.g., with the most recently updated lab type at the top). At FIG. 6B, latest sort option 630a is displayed with a visually distinct appearance (e.g., bolded, outlined, and/or highlighted) to indicate that latest sort option 630a is currently selected. Labs user interface 620a further includes alphabetical sort option 632a, which, when selected, causes computer system 600 to display labs data included in labs user interface 620a based at least partially on alphabetical order information (e.g., the labs data are sorted into alphabetical order). At FIG. 6B, alphabetical sort option 632a is displayed with an appearance that does not include a visual distinction indicating that alphabetical sort option 632a is selected (e.g., without a bold, outlined, or highlighted visual appearance) to indicate that alphabetical sort option 632a is not currently selected.

Labs user interface 620a further includes pinned labs tip 634, which includes pin description 634a about lab types corresponding to lab affordances included in labs user interface 620a can be pinned (e.g., designated via a user input), and dismiss affordance 634b which, when selected, causes computer system 600 to stop displaying (e.g., forego displaying) pinned labs tip 634.

Labs user interface 620a further includes timeframe indicator 636, which includes a visual and/or textual indicator that the lab data displayed below timeframe indicator 636 corresponds to a particular timeframe (e.g., the last 7 days, the last 30 days). Labs user interface 620a further includes affordances corresponding to lab results, as described below.

Labs user interface 620a includes lab affordance 638a which, when selected, causes computer system 600 to display a corresponding lab room user interface. Lab affordance 638a includes lab type 638a1, which includes a visual and/or textual indicator of the type of the lab type that corresponds to lab affordance 638a (e.g., the physiological feature being measured by the corresponding lab). Lab affordance 638a further includes value 638a2, which corresponds to a lab measurement (e.g., the most recent lab measurement) that corresponds to lab affordance 638a. Lab affordance 638a further includes date 638a3, which includes a visual and/or textual indicator of the date on which the corresponding lab type was updated.

Labs user interface 620a further includes lab affordance 640a which, when selected, causes computer system 600 to display a corresponding lab room user interface. Lab affordance 640a includes lab type 640a1, which includes a visual and/or textual indicator of the type of lab that corresponds to lab affordance 640a (e.g., the physiological feature being measured by the corresponding lab). Lab affordance 640a further includes value 640a2, which corresponds to a lab measurement (e.g., the most recent lab measurement) that corresponds to lab affordance 640a. Lab affordance 640a further includes date 640a3, which includes a visual and/or textual indicator of the date on which the corresponding lab type was updated. Lab affordance 640a further includes range 640a4, which includes a graphical indicator of the most recent lab result corresponding to lab affordance 640a relative to a range of possible values for the corresponding lab type (e.g., the most recent lab result compared to full range of possible results, the most recent lab result compared to a healthy range of values,).

Labs user interface 620a further includes lab affordance 642a which, when selected, causes computer system 600 to display a corresponding lab room user interface. Lab affordance 642a includes lab type 642a1, which includes a visual and/or textual indicator of the type of lab that corresponds to lab affordance 642a (e.g., the physiological feature being measured by the corresponding lab). Lab affordance 642a further includes value 642a2, which corresponds to a lab measurement (e.g., the most recent lab measurement) that corresponds to lab affordance 642a. Lab affordance 642a further includes date 642a3, which includes a visual and/or textual indicator of the date on which the corresponding lab type was updated.

At FIG. 6B, computer system 600 detects input 650b (e.g., a tap input) on alphabetical sort option 632a. In response to receiving input 650b, computer system 600 displays labs user interface 620b, as illustrated in FIG. 6C.

Figures 6C, 6D:
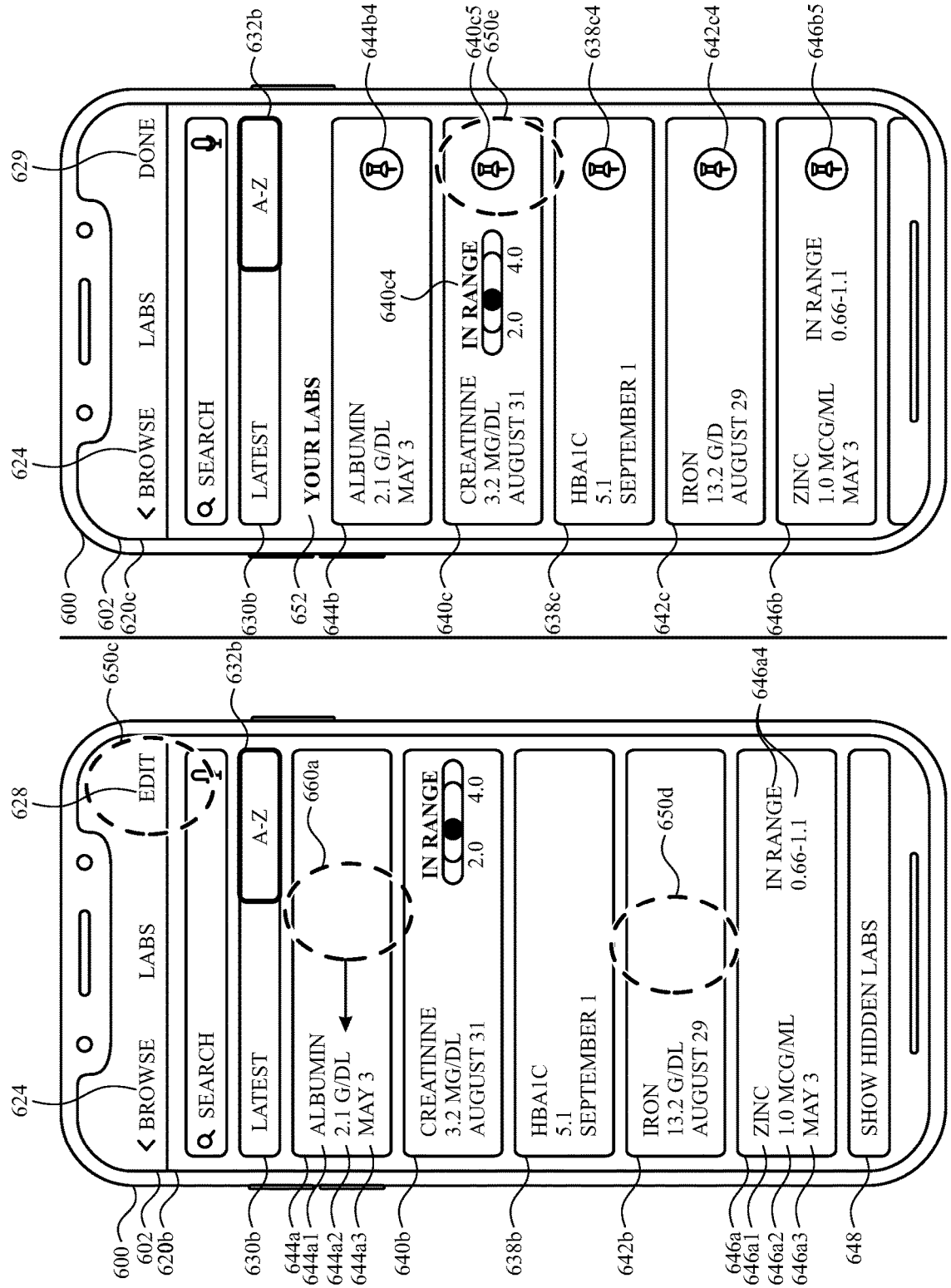

FIG. 6C illustrates computer system 600 displaying labs user interface 620b. Labs user interface 620b illustrates a lab user interface with lab results displayed in alphabetical order (e.g., based on the corresponding lab type). In some embodiments, displaying the lab affordances according to a different sort order causes contents to be displayed at a different location within the lab affordances. For example, FIG. 6C illustrates that the dates included in lab affordances (e.g., 644a, 640b, 638b, 642b, and 646c) are displayed below the corresponding lab values, whereas the dates were displayed in a right-alignment within the lab affordances in FIG. 6B.

Labs user interface 620b includes lab affordance 644a, which includes lab type 644a1 indicating that lab affordance 644a corresponds to "Albumin." Lab affordance 644a further includes value 644a2, which corresponds to a lab measurement (e.g., the most recent lab measurement) that corresponds to lab affordance 644a. Lab affordance 644a further includes date 644a3, which includes a visual and/or textual indicator of the date on which the corresponding lab type was updated.

Labs user interface 620b further includes lab affordance 646a, which includes lab type 646a1, indicating that the corresponding lab type is "Zinc." Lab affordance 646a further includes value 646a2, which corresponds to a lab measurement (e.g., the most recent lab measurement) that corresponds to lab affordance 646a. Lab affordance 646a further includes date 646a3, which includes a visual and/or textual indicator of the date on which the corresponding lab type was updated. Lab affordance 646a further includes range 646a4, which includes a graphical indicator of the most recent lab result corresponding to lab affordance 646a relative to a range of possible values for the corresponding lab type (e.g., the most recent lab result compared to full range of possible results, the most recent lab result compared to a healthy range of values, etc.).

Labs user interface 620b further includes lab affordance 640b, which includes contents similar to lab affordance 640a, lab affordance 638b, which includes contents similar to lab affordance 638a, as described above, and lab affordance 642b, which includes content similar to lab affordance 642a, as described above.

Labs user interface 620b further includes alphabetical sort option 632b, which, when selected, causes computer system 600 to display labs data included in labs user interface 620b based at least partially on alphabetical order information. Labs user interface 620b further includes latest sort option 630b, which, when selected, causes computer system 600 to display labs data included in labs user interface 620b at least partially based on chronology information (e.g., with the most recently updated lab type updated at the top). Labs user interface further includes show hidden labs affordance 648 which, when selected, causes computer system 600 to display additional labs data not currently included (e.g., displayed) in labs user interface 620b.

Labs user interface 620b further includes edit affordance 628 which, when selected, causes computer system 600 to display a user interface for editing aspects of the labs data included in labs user interface 620b, as illustrated in FIG. 6D. In labs user interface 620b, computer system 600 receives various user inputs (650c, 660a, 650d) corresponding to requests to initiate processes for pinning labs (e.g., designating labs via a user input).

At FIG. 6C, computer system 600 receives input 650c (e.g., a tap input) on edit affordance 628. In response to receiving input 650c, computer system 600 displays labs user interface 620c, as illustrated in FIG. 6D. At FIG. 6C, computer system further receives input 660a (e.g., a swipe input) on lab affordance 644a and, in response, displays labs user interface 620d, as illustrated in FIG. 6E. At FIG. 6C, computer system 600 further receives long press input 650d on lab affordance 642b and, in response, displays an option for pinning the "Iron" lab type as illustrated in FIG. 6F, below.

At FIG. 6D, computer system 600 displays labs user interface 620c, which includes options for pinning lab types. Selecting a pin icon causes a corresponding lab result to be pinned (e.g., designated via a user input). For example, at FIG. 6D, computer system 600 receives input 650e (e.g., a tap input) on pin icon 640c5, which is included in lab affordance 640a and, in response to receiving input 650e, computer system 600 designates (e.g., pins) the lab type corresponding to lab affordance 640c (e.g., "Creatinine") as illustrated in FIG. 6G, below.

Labs user interface 620c includes lab affordance 644b that includes content similar to lab affordance 644a, and which further includes pin icon 644b4 for pinning the lab type corresponding to lab affordance 644b. Labs user interface 620c further includes lab affordance 640c that includes contents similar to lab affordance 640a, as described above, and which further includes pin icon 640c4 for pinning the lab type corresponding to lab affordance 640c. Labs user interface 620c further includes lab affordance 638c that includes contents similar to lab affordance 638a, as described above, and which further includes pin icon 638c4 for pinning the lab type corresponding to lab affordance 638c. Labs user interface 620c further includes lab affordance 642c that includes content similar to lab affordance 642a, but which, at FIG. 6D, further includes pin 642c4 for pinning the lab type corresponding to lab affordance 642c. Labs user interface 620c further includes lab affordance 646b that includes content similar to lab affordance 646a, but which, at FIG. 6D, further includes pin 646b5 for pinning the lab type corresponding to lab affordance 646b.

At FIG. 6E, computer system 600 displays labs user interface 620d, which includes an option to pin the "Albumin" lab type, in response to receiving swipe input 660a on lab affordance 644a as illustrated in FIG. 6C, above. Labs user interface 620d includes lab affordance 644c that includes content similar to lab affordance 644a, and which further includes lab affordance 644c with pin option 644c4 which, when selected, designates (e.g., pins) the lab type corresponding to lab affordance 644c (e.g., "Albumin"). In some embodiments, updating lab affordance 644c in response to receiving input 660a includes displaying an animation wherein lab affordance 644c slides over to make room for pin option 644c4. At FIG. 6E, computer system 600 receives input 650f (e.g., a tap input) on pin option 644c4. In response to receiving input 650f, computer system 600 designates (e.g., pins) the lab type corresponding to lab affordance 644c (e.g., "Albumin"), as illustrated in FIG. 6G, below.

Labs user interface 620d further includes lab affordance 640d that includes contents similar to lab affordance 640a, as described above. Labs user interface 620d further includes lab affordance 638d that includes contents similar to lab affordance 638a, as described above. Labs user interface 620d further includes lab affordance 642d that includes content similar to lab affordance 642a, as described above. Labs user interface 620d further includes lab affordance 646c that includes content similar to lab affordance 646a, as described above.

At FIG. 6F, in response to receiving input 650d, as illustrated in FIG. 6C above, computer system 600 displays labs user interface 620e. Labs user interface 620e is an updated version of labs user interface 620c wherein, in response to receiving input 650d, computer system displays labs user interface 620e with lab affordances different from the selected lab affordances as grayed out (e.g., 644d, 640e, 638e, 646d). The selected lab affordance (e.g., 642e), however, is displayed without being grayed out, and a pin lab affordance 654 is displayed next to it to indicate that the corresponding lab type (e.g., "Iron") can be pinned via an input on pin lab affordance 654. In FIG. 6F, computer system 600 detects input 650g on pin lab affordance 654 and, in response, pins the "Iron" lab type.

Labs user interface 620e includes lab affordance 644d, which includes content similar to lab affordance 644a, as described above. Labs user interface 620e further includes lab affordance 640e, which includes contents similar to lab affordance 640a, as described above. Labs user interface 620e further includes lab affordance 638e, which includes contents similar to lab affordance 638a, as described above. Labs user interface 620e further includes lab affordance 642e, which includes content similar to lab affordance 642a, as described above. Labs user interface 620e further includes lab affordance 646d, which includes content similar to lab affordance 646a.

FIG. 6G illustrates computer system 600 displaying labs user interface 620f, wherein both the lab type corresponding to "Albumin" and the lab result corresponding to "Creatinine" have been pinned (e.g., designated via a user input as in FIGS. 6D, 6E, and/or 6F) as illustrated by lab affordance 644e and lab affordance 640f. Lab user interface 620f includes pinned identifier 656, which includes a visual and/or textual indication of a portion of labs user interface 620f in which pinned labs are displayed. Labs user interface 620f further includes your labs indicator 652, which includes a visual and/or textual indication of a portion of labs user interface 620f in which non-pinned labs are displayed.

Labs user interface 620f is a user interface for editing the pin status of the lab types included in labs user interface 620f. Lab affordances corresponding to pinned lab types are displayed with affordances to unpin their corresponding lab types, whereas lab affordances corresponding to unpinned lab types are displayed with affordances to pin their corresponding lab types. Labs user interface 620f includes lab affordance 644e, which includes content similar to lab affordance 644a, and which further includes unpin icon 644e4 which, when selected, causes the lab type corresponding to lab affordance 644e to be unpinned (e.g., to no longer be designated). Labs user interface 620f further includes lab affordance 640f, which includes content similar to lab affordance 640a, and which further includes unpin icon 640f5 which, when selected, causes the lab type corresponding to lab affordance 640f to be unpinned (e.g., to no longer be designated). Labs user interface 620f further includes lab affordance 638f, which includes content similar to lab affordance 638c, as described above. Labs user interface 620f further includes lab affordance 642f, which includes content similar to lab affordance 642c, as described above. Labs user interface 620f further includes lab affordance 646e, which includes content similar to lab affordance 646b, as described above.

Lab user interface 620f further includes done affordance 629 which, when selected, causes computer system 600 to exit the user interface for editing aspects of the labs data. In FIG. 6G, computer system 600 receives input 650h (e.g., a tap input) on done affordance 629. In response to receiving input 650h, computer system 600 displays labs user interface 620g, as illustrated in FIG. 6H.

FIG. 6H illustrates computer system 600 displaying labs user interface 620g. Labs user interface 620g illustrates a user interface including some pinned lab types, and some unpinned lab types. For example, lab affordance 640g corresponds to a pinned "Creatinine" lab type, and lab affordance 644f corresponds to a pinned "Albumin" lab type, whereas lab affordance 638g corresponds to an unpinned "HbA1c" lab type, lab affordance 642g corresponds to an unpinned "Iron" lab type, and lab affordance 646f corresponds to an unpinned "Zinc" lab type.

Labs user interface 620g includes lab affordance 644f, which includes content similar to lab affordance 644a, as described above. Labs user interface 620g further includes lab affordance 640g, which includes content similar to lab affordance 640a, as described above. Labs user interface 620g further includes lab affordance 638g, which includes contents similar to lab affordance 638a, as described above. Labs user interface 620g further includes lab affordance 642g, which includes content similar to lab affordance 642a, as described above. Labs user interface 620g further includes lab affordance 646f, which includes content similar to lab affordance 646a, as described above.

At FIG. 6H, alphabetical sort option 632a is displayed with an appearance that does not include a visual distinction indicating that alphabetical sort option 632a is selected (e.g., without a bold, outlined, or highlight visual appearance) to indicate that alphabetical sort option 632a is not currently selected. Notably, the pinned lab types and the unpinned lab types are sorted separately. For example, although date 638g3 indicates that the "HbA1c" lab type was updated on September 1, which is more recent than the most recent update indicated by date 640g3 for the "Creatinine" lab type, lab affordance 640g, which corresponds to lab type 640g1 ("Creatinine") is still displayed higher closer to the top of labs user interface 620g than lab affordance 638g, which corresponds to lab type 638g1 ("HbA1c"). Thus, the sorting criteria is partially based on chronology information, but also at least partially based on the pin status (e.g., designation status) of lab types.

Figure 6I:
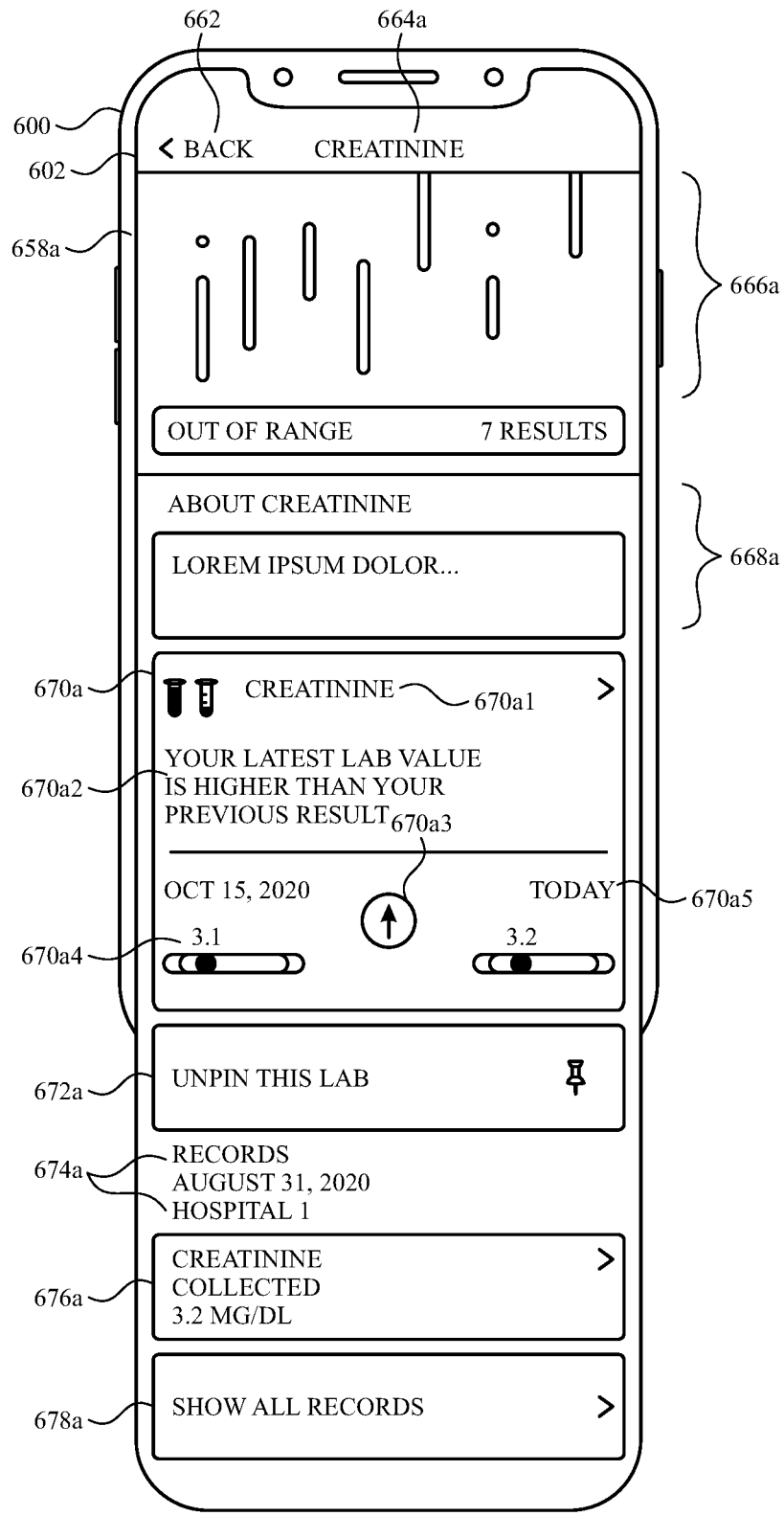
Figure 6J:
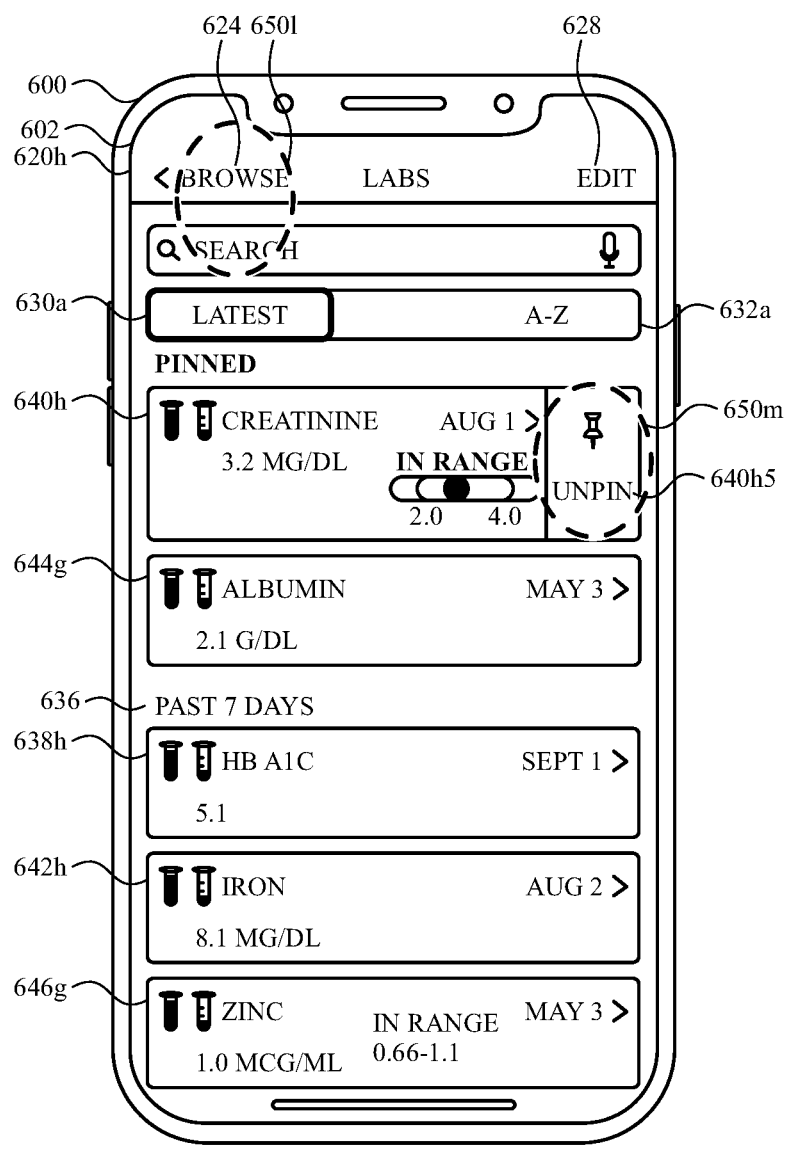
Figure 6K:
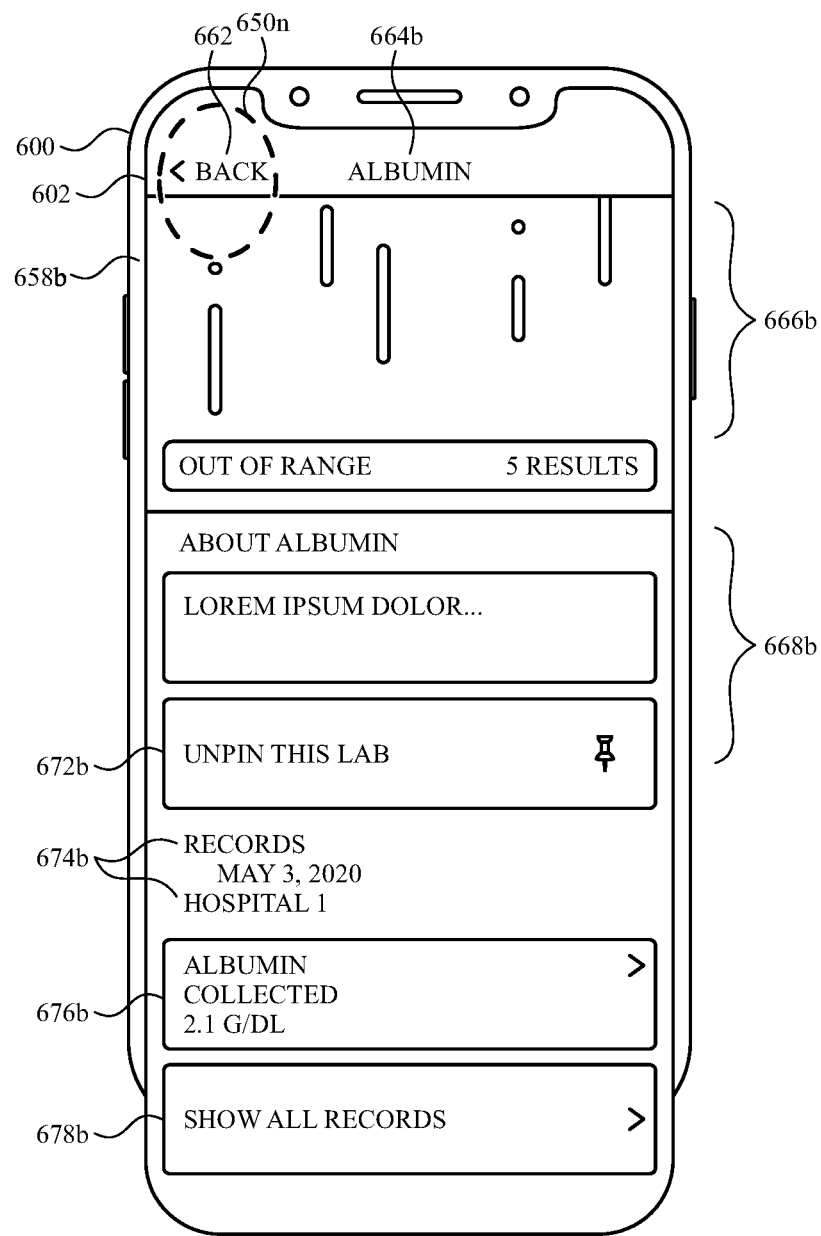
Figure 6L:
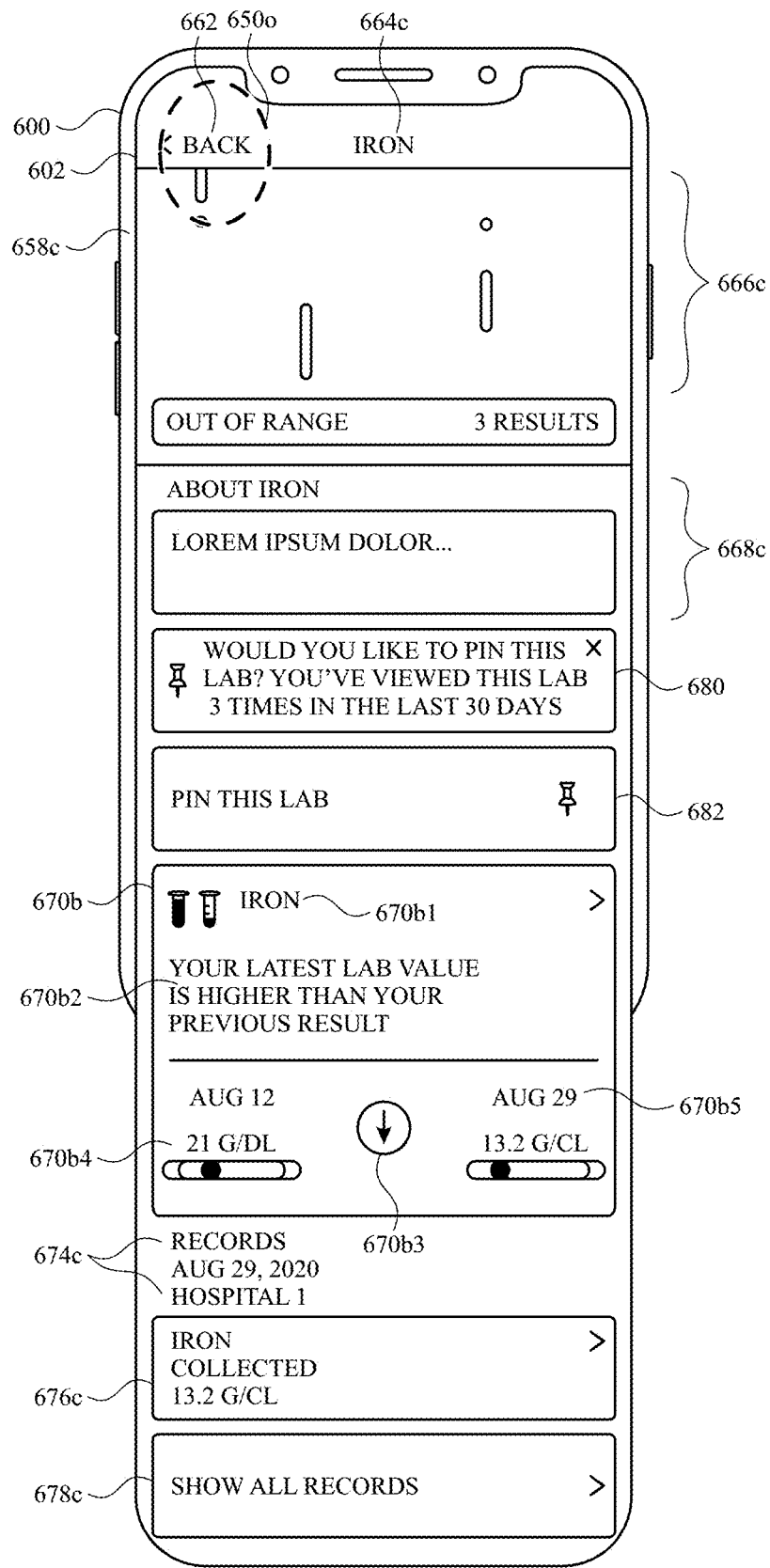
Figure 6N:
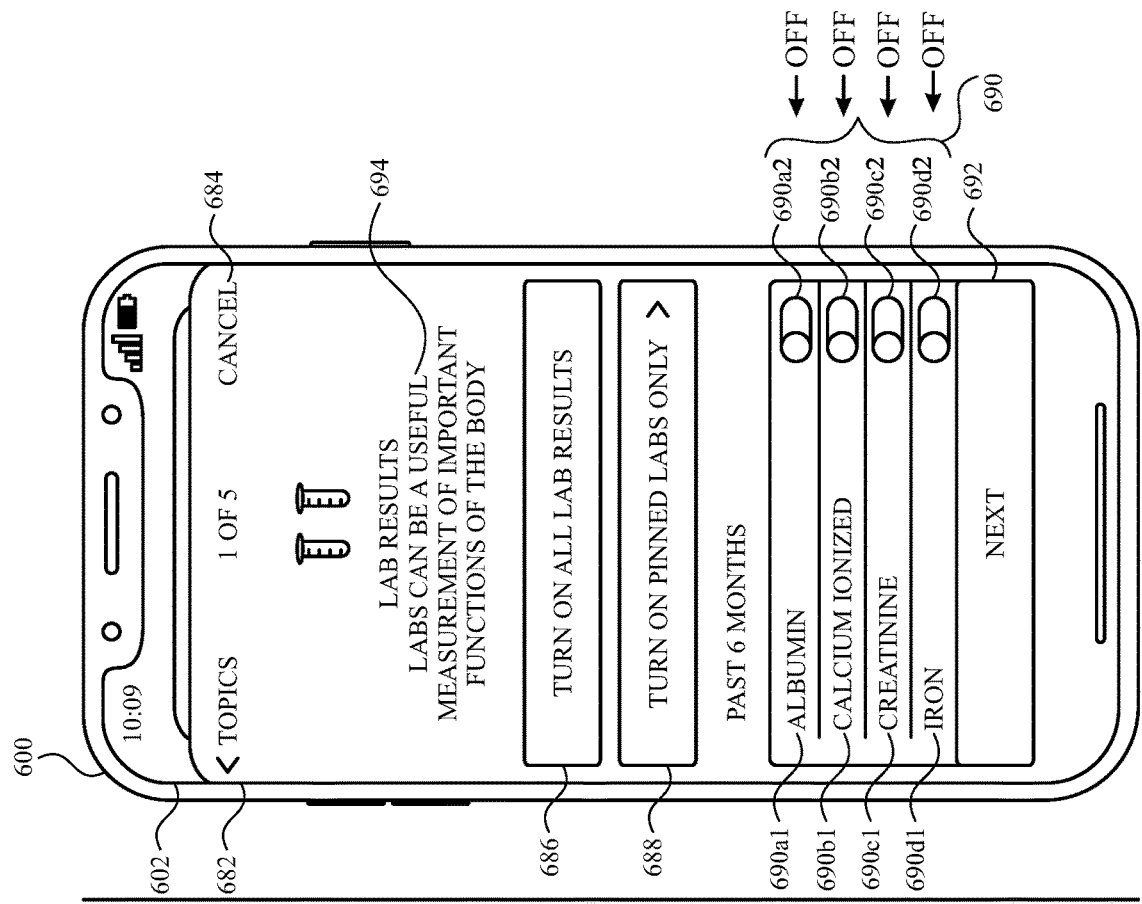

In FIG. 6H, computer system 600 receives input 650i (e.g., a tap input) on lab affordance 644f, input 650j on lab affordance 640g, which causes computer system 600 to display an "Albumin" lab room user interface as illustrated in FIG. 6K below. At FIG. 6H, computer system 600 further receives input 650j on lab affordance 640g, which causes computer system 600 to display a "Creatinine" lab room user interface as illustrated in FIG. 6I below. In FIG. 6H, computer system 600 further receives input 660b (e.g., a swipe input) on lab affordance 640g, which causes computer system 600 to display an unpin option for the "Creatinine" lab type as illustrated in FIG. 6J below. In FIG. 6H, computer system 600 further receives input 650k (e.g., a tap input) on lab affordance 642g, which causes computer system 600 to display an "Iron" lab room user interface 658c, as illustrated in FIG. 6L below.

At FIG. 6I, in response to receiving input 650j, computer system 600 displays lab room user interface 658a. Lab room user interface 658a is a user interface for displaying more detailed information related to the lab type corresponding to the selected lab affordance (e.g., "Creatinine"). FIG. 6I illustrates a user interface that includes labs data and/or results corresponding to a selected lab type (e.g., "Creatinine"). Lab room user interface 658a includes back affordance 662 which, when selected, causes computer system 600 to display a previous user interface that was displayed before lab room user interface 658a was displayed (e.g., labs user interface 620g). Lab room user interface 658a further includes lab type 664a, which indicates the lab type to which lab room user interface 658a corresponds (e.g., "Creatinine"). Lab room user interface 658a further includes chart data 666a, which includes graphs and/or charts corresponding to lab results corresponding to lab type 664a. Lab room user interface 658a further includes education 668a about lab type 664a (e.g., common causes for getting labs related to lab type 664a, physiological functions related to lab type 664a).

Lab room user interface 658a further includes delta highlight 670a, which includes information related to the difference between a more recent lab result with a previous lab result. Delta highlight 670a includes lab type 670a1, which includes a visual and/or textual indication of the lab type being compared, and assessment 670a2, which includes a visual and/or textual indication of the difference between a more recent lab result of the indicated lab type and a less recent lab result of the indicated lab type. Delta highlight 670a further includes graphical indicator 670a3, which includes a graphical representation of the relative relationship between the more recent lab result of the indicated lab type and the previous lab result of the indicated lab type (e.g., an up arrow if the more recent lab result is higher than the less recent lab result, a horizontal line if the more recent lab result and the less recent lab result are the same, and a down arrow if the more recent lab result is lower than the less recent lab result). Delta highlight 670a further includes range 670a4, which provides a graphical indication of the less recent lab result relative to a range of possible lab result values for the corresponding lab type, and range 670a5, which includes a graphical indication of the more recent lab result relative to a range of possible lab result values for the corresponding lab type.

Lab room user interface 658a further includes unpin affordance 672a which, when selected, causes the lab type indicated by lab type 664a to be undesignated by a user input (e.g., unpinned; no longer designated by a user input). Lab room user interface 658a further includes records indicator 674a, which includes a visual and/or textual indication of records data corresponding to one or more lab results corresponding to lab type 664a. Lab room user interface 658a further includes lab affordance 676a, which corresponds to a lab result of the lab type corresponding to lab type 664a. Lab room user interface 658a further includes show all affordance 678a which, when selected, causes computer system 600 to display additional lab results corresponding to lab type 664a in lab room user interface 658a.

At FIG. 6J, computer system 600 displays labs user interface 620h in response to receiving swipe input 660b as illustrated in FIG. 6H. Labs user interface 620h is an updated version of labs user interface 620g wherein, in response to receiving input 660b, computer system displays lab affordance 640h with unpin option 640h5. In FIG. 6J, computer system 600 receives input 650m on unpin option 640h5 and, in response, unpins the corresponding lab type ("Creatinine").

Lab affordance 640h includes content similar to lab affordance 640h but, in FIG. 6H, now further includes unpin option 640h5 which, when selected, un-designates (e.g., unpins) the lab type corresponding to lab affordance 640h (e.g., lab type 640h1, "Creatinine").

Labs user interface 620h includes lab affordance 644g, which includes content similar to lab affordance 644a, as described above. Labs user interface 620h further includes lab affordance 638h, which includes contents similar to lab affordance 638a, as described above.

Labs user interface 620h further includes lab affordance 642h, which includes content similar to lab affordance 642a, as described above. Labs user interface 620h further includes lab affordance 646g, which includes content similar to lab affordance 646g, as described above.

In FIG. 6K computer system 600 displays lab room user interface 658b in response to receiving input 650i in FIG. 6H, as described above. FIG. 6K illustrates a user interface that includes labs data and/or results corresponding to a selected lab type (e.g., "Albumin"). Notably, in contrast to lab room user interface 658a, lab room user interface 658b does not include a graphical indication of the differences between two values corresponding to the lab type. In some embodiments, a lab room user interface forgoes displaying a graphical indication of the difference between two values corresponding to the lab type if the computer system only has access to one record and/or value corresponding to the lab type.

Lab room user interface 658b includes lab type 664b, which indicates the lab type to which lab room user interface 658b corresponds (e.g., "Albumin"). Lab room user interface 658b further includes chart data 666b, which includes graphs and/or charts corresponding to lab results corresponding to lab type 664b. Lab room user interface 658b further includes education 668b about lab type 664b (e.g., common causes for getting labs related to lab type 664b, a physiological function related to lab type 664b).

Lab room user interface 658b further includes unpin affordance 672b which, when selected, causes the lab type indicated by lab type 664b to be undesignated by a user input (e.g., unpinned). Lab room user interface 658b further includes records indicator 674b, which includes a visual and/or textual indication of records data corresponding to one or more lab results corresponding to lab type 664b. Lab room user interface 658b further includes lab affordance 676b, which corresponds to a lab result corresponding to lab type 664b. Lab room user interface 658b further includes show all affordance 678b which, when selected, causes computer system 600 to display additional lab results corresponding to lab type 664b in lab room user interface 658b.

In FIG. 6K, computer system 600 receives input 650n (e.g., a tap input) on back affordance 662. In response to receiving input 650n, computer system 600 returns to displaying labs user interface 620g.

In FIG. 6L, computer system 600 displays lab room user interface 658c in response to receiving input 650k in FIG. 6H, as described above. FIG. 6L illustrates a lab room user interface for a lab type that has not been pinned (e.g., "Iron"). Lab room user interface 658c includes lab type 664c, which indicates the lab type to which lab room user interface 658c corresponds (e.g., "Iron"). Lab room user interface 658c further includes chart data 666c, which includes graphs and/or charts corresponding to lab results corresponding to lab type 664c. Lab room user interface 658c further includes education 668c about lab type 664c (e.g., common causes for getting labs related to lab type 664c, a physiological function related to lab type 664). Lab room user interface 658c further includes visual indication 680 that information indicating that lab type 664c can be pinned.

Figure 6M:
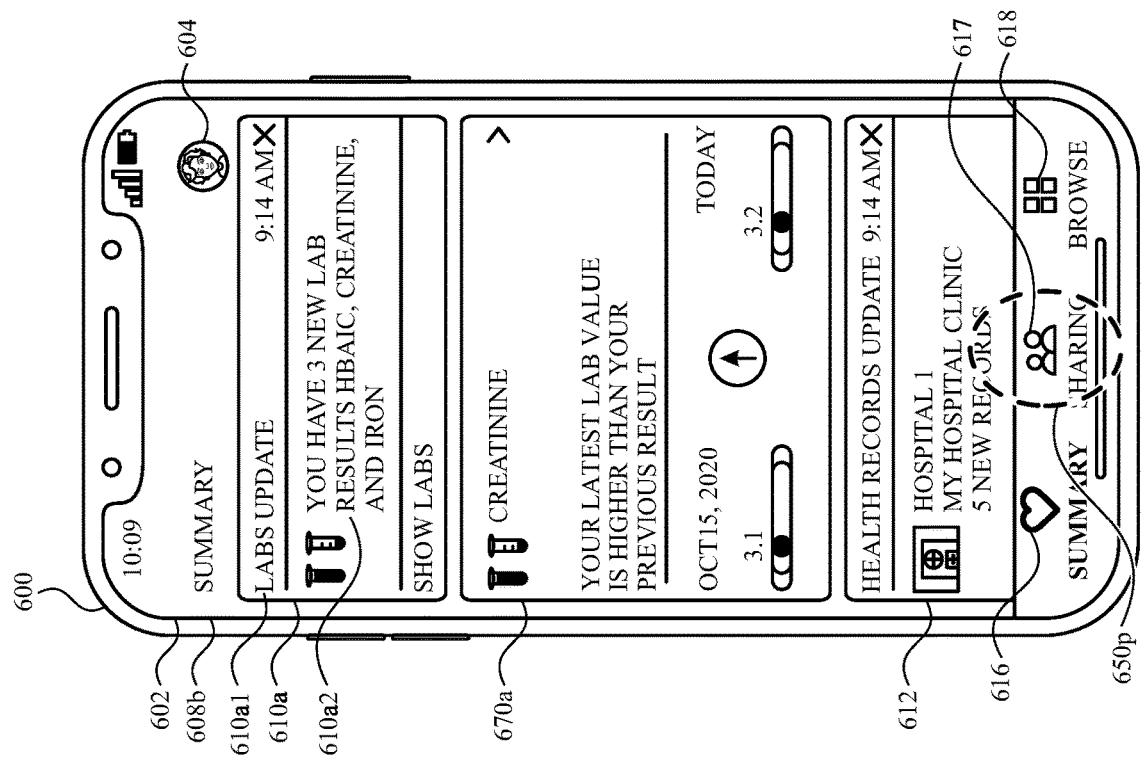

Lab room user interface 658c further includes delta highlight 670b, which includes information related to the difference between a more recent lab result with a previous lab result. Notable, in contrast to delta highlight 670b, delta highlight 670a is not included in summary user interface 608b as illustrated in FIG. 6M below. In some embodiments, delta highlight 670b is not included in summary user interface 608b at least partially because the lab type corresponding to delta highlight 670b (e.g., "Iron") has not been pinned.

Delta highlight 670b includes lab type 670b1, which includes a visual and/or textual indication of the lab type being compared, and assessment 670b2, which includes a visual and/or textual indication of the difference between a more recent lab result of the indicated lab type and a less recent lab result of the indicated lab type. Delta highlight 670b further includes graphical indicator 670b3, which includes a graphical representation of the relative relationship between the more recent lab result of the indicated lab type and the previous lab result of the indicated lab type. Delta highlight 670b further includes range 670b4, which provides a graphical indication of the less recent lab result relative to a range of possible lab results values for the corresponding lab type, and range 670b5, which includes a graphical indication of the more recent lab result relative to a range of possible lab result values for the corresponding lab type.

Lab room user interface 658c further includes pin affordance 681 which, when selected, causes the lab type indicated by lab type 664c to be designated by a user input (e.g., pinned). Lab room user interface 658c further includes records indicator 674c, which includes a visual and/or textual indication of records data corresponding to one or more lab results corresponding to lab type 664c. Lab room user interface 658c further includes lab affordance 676c, which corresponds to a lab result corresponding to lab type 664c. Lab room user interface 658c further includes show all affordance 678c which, when selected, causes computer system 600 to display additional lab results corresponding to lab type 664c in lab room user interface 658c. At FIG. 6L, computer system 600 receives input 6500 (e.g., a tap input) and, in response, returns to displaying labs user interface 620g.

In FIG. 6M, computer system 600 displays summary user interface 608b in response to receiving input 6501 on back affordance 624 as illustrated in FIG. 6J, as discussed above. In summary user interface 608, a lab type corresponding to "Creatinine" and a lab type corresponding to "Albumin" are pinned (e.g., designated via a user input), as illustrated in FIG. 6J. At FIG. 6M, in accordance with a determination that the lab type corresponding to "Creatinine" is pinned, and that computer system 600 has data available to display delta highlight for "Creatinine" lab type, computer system 600 includes delta highlight 670a in summary user interface 608b. Notably, summary user interface 608b does not include a delta highlight for the lab type corresponding to "Albumin" because, as illustrated in FIG. 6K, computer system does not have a delta highlight available for the lab type corresponding to "Albumin" (e.g., no delta highlight is included in the lab room user interface corresponding to the "Albumin" lab type). Further, summary user interface 608b does not include delta highlight 670b, which corresponds to the lab type corresponding to "Iron." Lab room user interface 658c includes a delta highlight for the lab type corresponding to the iron (e.g., delta highlight 670b, as illustrated in FIG. 6L), indicating that computer system 600 has data available to display a delta highlight related to the "Iron" lab type. However, delta highlight 670b is not included in summary user interface 608b at least partially because the lab type corresponding to "Iron" is not pinned (e.g., designated by a user input) at the time that computer system 600 displays summary user interface 608b As illustrated in FIG. 6M, summary user interface 608b includes delta highlight 670a, which includes lab type 670a1. Summary user interface 608b further includes summary affordance 616 which, when selected, causes computer system 600 to display summary user interface 608b. At FIG. 6M, summary affordance 616 is displayed with a visually distinct appearance (e.g., bolded, outlined, and/or highlighted) to indicate that summary information is currently being displayed and/or that summary affordance 616 is currently selected. At FIG. 6M, computer system 600 receives input 650p on sharing affordance 617.

In FIG. 6N, computer system 600 displayed sharing user interface 682 in response to receiving input 650p on sharing affordance 617, as illustrated in FIG. 6M, as discussed above. FIG. 6N illustrates a user interface for sharing lab data and/or transmitting lab data. Sharing user interface 682 includes cancel affordance 684 which, when selected, causes computer system to return to the user interface that was displayed before sharing user interface 682 was displayed (e.g., summary user interface 608b). Sharing user interface further includes sharing labs indicator 694, which provides a visual and/or graphical indication that sharing user interface 682 is a user interface for sharing labs data and/or results. Sharing user interface 682 further includes all labs affordance 686 which, when selected, selects all lab types available to computer 600 at the time that all labs affordance 686 is selected to be shared and/or transmitted. Sharing user interface 682 further includes pinned labs affordance 688 which, when selected, selects lab types that are pinned (e.g., designated via a user input) at the time that pinned labs affordance 688 is selected to be shared and/or transmitted.

Sharing user interface 682 further includes individual toggles for selecting lab types to be shared and/or transmitted. For example, sharing user interface includes lab type 690a1, which indicates a first lab type for sharing ("Albumin") and is displayed next to toggle 690a2 which, when selected, toggles (e.g., switches from selected to non-selected, or from non-selected to selected) a selection status of the first lab type. Sharing user interface further includes lab type 690b1, which indicates a second lab type for sharing ("Calcium Ionized") and is displayed next to toggle 690b2 which, when selected, toggles a selection status of the second lab type. Sharing user interface further includes lab type 690c1, which indicates a third lab type for sharing ("Creatinine") and is displayed next to toggle 690c2 which, when selected, toggles a selection status of the third lab type. Sharing user interface further includes lab type 690d1, which indicates a fourth lab type for sharing ("Iron") and is displayed next to toggle 690d2 which, when selected, toggles a selection status of the fourth lab type. Sharing user interface 682 further includes next affordance 692 which, when selected, causes computer system 600 to proceed to a next step of the process (e.g., display a next user interface) for sharing and/or transmitting labs data related to lab types that are selected at the time that next affordance 692 is selected.

FIG. 7 is a flow diagram illustrating a method for displaying user interfaces for displaying lab types based on their designation status using a computer system in accordance with some embodiments. Method 700 is performed at a computer system (e.g., 100, 300, 500) (e.g., a wearable electronic device (e.g., a smartwatch), a smartphone, a desktop computer, a laptop, a tablet) that is in communication with a display generation component and one or more input devices (e.g., a display controller, a touch-sensitive display system, a rotatable input mechanism, a touch-sensitive surface). Some operations in method 700 are, optionally, combined, the orders of some operations are, optionally, changed, and some operations are, optionally, omitted.

As described below, method 700 provides an intuitive way for displaying lab types based on their designation status. The method reduces the cognitive burden on a user for displaying lab types based on their designation status, thereby creating a more efficient human-machine interface. For battery-operated computing devices, enabling a user to view lab types based on their designation status faster and more efficiently conserves power and increases the time between battery charges.

The computer system (e.g., 600) displays (e.g., 702), via the display generation component, a first user interface (e.g., a health summary user interface) (e.g., 608b) that includes a user-interactive graphical user interface object (e.g., an affordance) corresponding to a first lab type (e.g., a type of physiological measurement, a type of lab result, a category of health and/or clinical data (e.g., blood glucose, creatinine, iron, LDL cholesterol)) (e.g., 670a).

In accordance with a determination (e.g., 704) that the first lab type has been (e.g., was previously) designated (e.g., pinned, selected) via a user input (e.g., via a tap input, a press input, and/or a swipe input) (e.g., 650e) received via the one or more input devices, the user-interactive graphical user interface object corresponding to the first lab type (e.g., 670a) includes a graphical indication (e.g., an up arrow (e.g., in a first color), a down arrow (e.g., in a second color different from the first color), and/or a horizontal line) (e.g., 670a3) of a difference (e.g., an increase, a decrease, an indication of a no change, an indication of a change, a delta) between a first value (e.g., numerical value corresponding to a physiological measurement and/or reading corresponding to a first lab data instance) corresponding to the first lab type and at least a second value (e.g., a physiological measurement and/or a reading corresponding to a second lab data instance different from the first lab data instance) corresponding to the first lab type.

In accordance with a determination (e.g., 706) that the first lab type has not been designated via a user input (e.g., via any previous user input; the first lab type is currently not a designated/selected/pinned lab type) (e.g., 650e), the computer system (e.g., 600) displays, via the display generation component (e.g., 602), the user-interactive graphical user interface object corresponding to the first lab type (e.g., 670*a*) without a graphical indication of the difference between the first value corresponding to the first lab type and at least the second value corresponding to the first lab type (e.g., with any graphical indications that relate to a difference between the first value and any other previous values for the first lab type). In some embodiments, the first value corresponding to the first lab type is the most recent (e.g., most recently performed and/or most recently received by the computer system) value (e.g., the physiological measurement and/or reading) corresponding to the first lab type. In some embodiments, the second value corresponding to the first lab type is less recent (e.g., less recently performed and/or less recently received by the computer system) than the first value corresponding to the first lab type. In some embodiments, the first value corresponding to the first lab type and the second value corresponding to the first lab type are the same. In some embodiments, the first value corresponding to the first lab type and the second value corresponding to the first lab type are different. In some embodiments, the graphical indication includes an up arrow if the first value is greater than the second value. In some embodiments, the graphical indication includes a down arrow if the first value is less than the second value. In some embodiments, the graphical indication includes a horizontal line if the first value and the second value are equal. Including a graphical indication of a difference two values that correspond to a lab type in accordance with a determination about whether the lab type has been designated via a user input enables the graphical indication of difference to be displayed without requiring the user to manually select the lab type to view the graphical indication of the difference. Performing an operation when a set of conditions has been met without requiring further user input enhances the operability of the device and makes the user-device interface more efficient (e.g., by displaying the graphical indication when criteria are met) which, additionally, reduces power usage and improves battery life of the device by enabling the user to use the device more quickly and efficiently. Further, displaying the graphical indication of the difference provides visual feedback about whether the value corresponding to the lab type has gone up or down. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, in accordance with a determination that the first value corresponding to the first lab type is greater than the second value corresponding to the first lab type, the graphical indication (e.g., 670*a*3) has a first appearance. In some embodiments, in accordance with a determination that the first value corresponding to the first lab type is less than the second value corresponding to the first lab type, the graphical indication has a second appearance different than the first appearance. In some embodiments, in accordance with a determination that the first value corresponding to the first lab type is equal to the second value corresponding to the first lab type, the graphical indication has a third appearance different from the first appearance and the second appearance. In some embodiments, the graphical indication indicates whether a lab result has increased, decreased, or stayed the same as compared to a previous lab result of the same time. In some embodiments, the graphical indication includes an up arrow if a more recent lab result is greater than a previous lab result of the same type. In some embodiments, the graphical indication includes a down arrow if the more recent lab result is lower than a previous lab result. In some embodiments, the graphical indication includes a straight line if the more recent lab result is the same as the previous lab result. Displaying the graphical indication with a different appearance in accordance with a determination about whether the value has increased, decreased, or stayed the same provides visual feedback about the overall trend in movement (e.g., trajectory) of the corresponding lab type. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, while performing a process to configure health-related data for sharing with a second user account (e.g., a user account associated with an external computer system), the computer system (e.g., 600) displays a sharing data selection user interface (e.g., 682), wherein displaying the sharing data selection user interface includes: in accordance with a determination that the first lab type has been designated via the user input (e.g., is a pinned lab type), the computer system displays a second user-interactive graphical user interface object (e.g., 690*a*2, 690*b*2, 690*c*2, 690*d*2) that, when selected, causes data of the first lab type to be shared with the second user account upon completion of the process to configure health-related data for sharing with a second user account. In some embodiments, in accordance with a determination that the first lab type has not been designated via the user input (e.g., is a pinned lab type), the computer system forgoes displaying the second user-interactive graphical user interface object that, when selected, causes data of the first lab type to be shared with the second user account upon completion of the process to configure health-related data for sharing with a second user account. In some embodiments, the pinned status of a lab type determines whether the lab type is recommended for sharing during a process for sharing health-related data. In some embodiments, while a lab type that is not designated is not recommended (e.g., surfaced as part of a preferred subset of data that can be shared) for sharing, that lab type can still be designated for sharing via a manual selection process that affords a user the ability to manually select what health-related data is shared. In accordance with a determination about whether a lab type has been designated, selectively displaying or not displaying a user-interactive graphical user interface object that, when selected, causes data of a lab type of be shared with a second user account upon completion of the process to configure health-related data for sharing with a second user account provides visual feedback about lab types that a user is more likely to want to share. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently. In accordance with a determination about whether a lab type has been designated, selectively displaying or not displaying a user-interactive graphical user interface object that, when selected, causes data of a lab type of be shared with a second user account upon completion of the process to configure health-related data for sharing with a second user account enables improved suggestions about which lab types are likely candidates for sharing without requiring the user to manually select which lab types to share from among all of their lab types. Performing an operation when a set of conditions has been met without requiring further user input enhances the operability of the device and makes the user-device interface more efficient (e.g., by providing suggestions about labs) which, additionally, reduces power usage and improves battery life of the device by enabling the user to use the device more quickly and efficiently.

In some embodiments, during the process to configure health-related data for sharing with a second user account, the computer system (e.g., 600) displays a lab type sharing selection user-interactive graphical user interface object (e.g., a lab type sharing selection affordance) (e.g., 617). In some embodiments, the computer system receives an input (e.g., 650*p*) corresponding to the lab type sharing selection user-interactive graphical user interface object. In some embodiments, in response to receiving the input corresponding to the lab type sharing selection user-interactive graphical user interface object, the computer system displays a third user-interactive graphical user interface object (e.g., 690*a*2) that, when selected, modifies whether data of the first lab type will be shared (e.g., toggling the state from not being shared to being shared and/or vice versa) with the second user account upon completion of the process to configure health-related data for sharing with a second user account and a fourth user-interactive graphical user interface object (e.g., 690*b*2) that, when selected, modifies whether data of a third lab type will be shared (e.g., toggling the state from not being shared to being shared and/or vice versa) with the second user account upon completion of the process to configure health-related data for sharing with a second user account. Displaying a third user-interactive graphical user interface object that, when selected, modifies whether data of the first lab type will be shared and a fourth user-interactive graphical user interface object that, when selected, modifies whether data of a third lab type will be shared enables the user to quickly and easily select the lab types that they wish to share, thereby reducing the number of inputs required to select the appropriate lab types to be shared. Reducing the number of inputs needed to perform an operation enhances the operability of the system and makes the computer system more efficient (e.g., by helping the user to quickly and easily select which labs to share) which, additionally, reduces power usage and improves battery life of the device by enabling the user to use the system more quickly and efficiently.

In some embodiments, prior to displaying the first user interface (e.g., 608*b*), the computer system (e.g., 600) displays, via the display generation component (e.g., 602), a second user interface (e.g., a labs user interface) (e.g., 620*a*). In some embodiments, the second user interface and the first user interface are the same user interface. In some embodiments, the second user interface and the second user interfaces are both interfaces of an application (e.g., a health data application) that includes a fifth user-interactive graphical user interface object (e.g., an affordance) (e.g., 640*c*) corresponding to the first lab type (e.g., a type of physiological measurement, a type of lab result, a category of health and/or clinical data) and a sixth user-interactive graphical user interface object corresponding to a second lab type (e.g., 644*a*). In some embodiments, the computer system receives (e.g., while displaying the second user interface) the user input (e.g., a tap input) (e.g., 650*e*) designating the lab type.

In some embodiments, in accordance with a determination that the fifth user-interactive graphical user interface object meets a threshold set of criteria (e.g., the lab has been selected and/or updated at least 3 times within a threshold amount of time (e.g., 3 months)), the computer system displays a visual indication (e.g., a textual indication) (e.g., 680) that the first lab type can be designated via a user input. Displaying a user interface with a fifth user-interactive graphical user interface object and a sixth user-interactive graphical user interface object that can be designated via a user input enables the user to quickly and easily select the lab types that they wish to pin from a single user interface, thereby reducing the number of inputs required to designate lab types. Reducing the number of inputs needed to perform an operation enhances the operability of the system and makes the computer system more efficient (e.g., by helping the user to quickly and easily designate a particular lab type) which, additionally, reduces power usage and improves battery life of the device by enabling the user to use the system more quickly and efficiently.

In some embodiments, the user input designating the lab type (e.g., 650*e*) is selected from the group consisting of: a sustained input of greater than a predetermined time on the fifth user-interactive graphical user interface object (e.g., a long-press on a touch-sensitive surface) (e.g., 650*d*), an input, which includes movement in a first direction (e.g., a swipe input (e.g., a right swipe) (e.g., 660*a*), that corresponds to (e.g., that at least starts on) the fifth user-interactive graphical user interface object (e.g., 644*a*), and a set of one or more inputs that includes a first input (e.g., 650*i*) corresponding to the fifth user-interactive graphical user interface object (e.g., a tap on the object that brings up a menu, followed by a second input selecting an option to designate the lab type (e.g., 682)). In some embodiments, the second user interface is configured to permit designating the lab type using any of the input types of the group. Allowing a user to designate a lab type via multiple methods (e.g., multiple types of input types) enables the user to quickly and easily select the lab types that they wish to pin in various ways, thereby reducing the number of inputs required to designate lab types. Reducing the number of inputs needed to perform an operation enhances the operability of the system and makes the computer system more efficient (e.g., by helping the user to quickly and easily designate a particular lab type) which, additionally, reduces power usage and improves battery life of the device by enabling the user to use the system more quickly and efficiently.

In some embodiments, in accordance with a determination that the first lab type has been (e.g., was previously) designated (e.g., pinned, selected) via a user input (e.g., via a tap input, a press input, and/or a swipe input) (e.g., 650*e*) received via the one or more input devices, the computer system (e.g., 600) includes the fifth user-interactive graphical user interface object (e.g., 640*g*) corresponding to the first lab type in a first set of one or more user-interactive graphical user interface objects (e.g., a set of objects that each have been designated via a user input) (e.g., 640*g*, 644*f*) that are displayed, via the display generation component, in a first portion of the second user interface (e.g., a portion of the second user interface for labs that have been designated (e.g., pinned)). In some embodiments, in accordance with a determination that the first lab type has not been designated via a user input (e.g., via any previous user input; the first lab type is currently not a designated/selected/pinned lab type), the computer system displays, via the display generation component, the fifth user-interactive graphical user interface object corresponding to the first lab type in a second set of one or more user-interactive graphical user interface objects (e.g., 638g, 642g, 646f) (e.g., a set of objects that each have not been designated via a user input) (that are displayed, via the display generation component, in a second portion of the second user interface (e.g., a portion of the interface for labs that have not been designated (e.g., pinned)). In some embodiments, the first portion of the second user interface and the second portion of the second user interface do not overlap. Displaying user-interactive graphical user interface object corresponding to a first lab type in a first portion of a user interface and user-interactive graphical user interface objects corresponding to a second lab type in a second portion of a user interface provides visual feedback about which lab types have been designated at a given point in time. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, the first set of one or more user-interactive graphical user interface objects (e.g., 640g, 644f) are sorted (e.g., arranged, ordered) in the first portion of the second user interface (e.g., 620f) according to a first sorting criteria (e.g., alphabetically, chronologically). In some embodiments, the second set of one or more user-interactive graphical user interface objects (e.g., 638g, 642g, 646f) are sorted (e.g., arranged, ordered) in the second portion of the second user interface according to a second sorting criteria (e.g., alphabetically, chronologically, a sorting criteria that is the same or different than the first sorting criteria, a sorting criteria that is independent from the first sorting criteria). Automatically sorting user-interactive graphical user interface objects within their respective portion of the second user interface enables an organized user interface with sorted user-interactive graphical user interface objects without requiring the user to manually sort or rearrange the user-interactive graphical user interface objects manually. Performing an operation when a set of conditions has been met without requiring further user input enhances the operability of the device and makes the user-device interface more efficient (e.g., by displaying information in a sorted order) which, additionally, reduces power usage and improves battery life of the device by enabling the user to use the device more quickly and efficiently.

In some embodiments, the second user interface (e.g., 620b) includes an edit user-interactive graphical user interface object (e.g., 628) that, when selected, initiates a process for modifying the designation state (e.g., changing the state from having been designated to not having been designated and/or vice versa) of the first lab type. Displaying an edit user-interactive graphical user interface object that, when selected, initiates a process for modifying the designation status of a lab type in the second user interface enables the user to quickly and easily begin modifying the designation status of lab types from the second user interface, thereby reducing the number of inputs required to edit the designation status of lab types. Reducing the number of inputs needed to perform an operation enhances the operability of the system and makes the computer system more efficient (e.g., by helping the user to quickly and easily designate a particular lab type) which, additionally, reduces power usage and improves battery life of the device by enabling the user to use the system more quickly and efficiently.

Note that details of the processes described above with respect to method 700 (e.g., FIG. 7) are also applicable in an analogous manner to the methods described below. For example, method 900 optionally includes one or more of the characteristics of the various methods described above with reference to method 700. For example, the user interfaces described above could include affordances that correspond to health topics, wherein the user-interactive graphical objects corresponding to lab types that are displayed in the user interfaces correspond to a selected health topic. For brevity, these details are not repeated below.

FIGS. 8A-8I illustrate exemplary user interfaces for displaying health topics. The user interfaces in these figures are used to illustrate the processes described below, including the processes in FIG. 9.

FIG. 8A illustrates computer system 600 displaying labs user interface 802a via display 602. In some embodiments, computer system 600 optionally includes one or more features of device 100, device 300, or device 500. In some embodiments, computer system 600 is a tablet, phone, laptop, desktop, camera, etc. In some embodiments, the inputs described below can optionally be substituted for alternate inputs, such as a swipe input and/or a long press input.

In FIG. 8A, computer system 600 displays labs user interface 802a. Labs user interface 802a includes affordances including labs data (e.g., 820a, 824a, 826a) and health condition filters (e.g., 814a, 816a, 818a) that, when selected, cause computer system 600 to display lab affordances that correspond to the selected health condition filter. In FIG. 8A, computer system 600 displays lab user interface 802a with the "All" lab condition filter 814a selected, which allows all available lab affordances to be displayed, regardless of whether the lab types corresponding to the displayed lab affordances correspond to a particular health condition.

Labs user interface 802a includes back affordance 806 which, when selected, causes computer system 600 to display a previously displayed user interface screen. Labs user interface 802a further includes search bar 810 which, when selected, causes computer 600 to display options for searching among the labs data included in labs user interface 802a (e.g., searching by inputting letters corresponding to lab data via a touch keyboard, searching via voice inputs received via a microphone). Labs user interface 802a further includes time indicator 804a, which includes a visual and/or textual representation of a current time (e.g., 7:00 at FIG. 8A). Labs user interface 802a further includes alphabetical sort option 812a, which, when selected, causes computer system 600 to display labs data included in labs user interface 802a based at least partially on alphabetical order information (e.g., the labs data are sorted into alphabetical order).

Labs user interface 802a further includes health condition filters that, when selected, cause computer system 600 to limit the lab affordances displayed to those that correspond to a health condition associated with the selected health condition filter. Labs user interface 802a includes health condition filter 814a, which corresponds to "All" health filters (e.g., allows all lab affordances to be displayed), health condition filter 816a, which corresponds to "Diabetes" and which, when selected, filters the displayed lab affordances to those associated with diabetes, and health condition filter 818a, which corresponds to "Heart Health" and which, when selected, filters the displayed lab affordances to those associated with heart health.

Labs user interface 802a further includes pinned indicator 821, which indicates a portion of labs user interface 802a that corresponds to lab types that have been pinned (e.g., designated via a user input). Labs user interface 802a further includes delta highlight 820a, which includes information related to the difference between a more recent lab result with a previous lab result. Delta highlight 820a includes lab type 820a1, which includes a visual and/or textual indication of the lab type being compared (e.g., "HbA1c" in FIG. 8A), and assessment 820a2, which includes a visual and/or textual indication of the difference between a more recent lab result of the indicated lab type and a less recent lab result of the indicated lab type. Delta highlight 820a further includes graphical indicator 820a3, which includes a graphical representation of the relative relationship between the more recent lab result of the indicated lab type and the previous lab result of the indicated lab type (e.g., an up arrow if the more recent lab result is higher than the less recent lab result, a horizontal line if the more recent lab result and the less recent lab result are the same, and a down arrow if the more recent lab result is lower than the less recent lab result). Delta highlight 820a further includes range 820a4, which provides a graphical indication of the less recent lab result relative to a range of possible lab results values for the corresponding lab type, and range 820a5, which includes a graphical indication of the more recent lab result relative to a range of possible lab result values for the corresponding lab type. Labs user interface 802a further includes timeframe indicator 822, which includes a visual and/or textual indicator that the lab data displayed below timeframe indicator 822 corresponds to a particular timeframe (e.g., the last 7 days, the last 30 days).

Labs user interface 802a further includes lab affordance 824a, which includes lab type 824a1, indicating that the corresponding lab type is "Creatinine." Lab affordance 824a further includes value 824a2, which corresponds to a lab measurement (e.g., the most recent lab measurement) that corresponds to lab affordance 824a. Lab affordance 824a further includes date 824a3, which includes a visual and/or textual indicator of the date on which the corresponding lab type was updated. Lab affordance 824a further includes range 824a4, which includes a graphical indicator of the most recent lab result corresponding to lab affordance 824a relative to a range of possible values for the corresponding lab type (e.g., the most recent lab result compared to a full range of possible results, the most recent lab result compared to a healthy range of values).

Labs user interface 802a further includes lab affordance 826a, which includes lab type 826a1, indicating that the corresponding lab type is "Calcium Ionized." Lab affordance 826a further includes value 826a2, which corresponds to a lab measurement (e.g., the most recent lab measurement) that corresponds to lab affordance 826a. Lab affordance 826a further includes date 826a3, which includes a visual and/or textual indicator of the date on which the corresponding lab type was updated.

In FIG. 8A, computer system 600 receives input 850a (e.g., a tap input) on alphabetical sort option 812a. Further, in FIG. 8A, computer system 600 receives input 860a (e.g., a swipe input) on labs user interface 802a.

In FIG. 8B, in response to receiving input 860a, computer system 600 displays labs user interface 802b. FIG. 8B illustrates computer system 600 displaying a labs user interface with a "Diabetes" health category filter selected, wherein the selected health condition filter has moved from "All" to "Diabetes" in response to input 860a. Labs user interface 802b includes at least a portion of health condition filter 814b, which corresponds to "All" health filters (e.g., allows all lab affordances to be displayed), health condition filter 816b, which corresponds to "Diabetes" and which, when selected, filters the displayed lab affordances to those associated with diabetes, and health condition filter 818b, which corresponds to "Heart Health" and which, when selected, filters the displayed lab affordances to those associated with heart health. In labs user interface 802b, health condition filter 816b includes a visual indication (e.g., an outline) indicating that health condition filter 816b is currently selected. Labs user interface 802b includes lab data that corresponds to the selected "Diabetes" health condition filter and, in particular, filters the displayed lab affordances to those that correspond to the selected "Diabetes" health condition filter. Labs user interface 802b includes education 828a about health condition filter 816b (e.g. "Diabetes").

Labs user interface 802b further includes delta highlight 820b, which includes content similar to delta highlight 820a, as discussed above. Labs user interface 802b further includes lab affordance 834a, which includes lab type 834a1, indicating that the corresponding lab type is "Fasting Glucose." Lab affordance 834a further includes value 834a2, which corresponds to a lab measurement (e.g., the most recent lab measurement) that corresponds to lab affordance 834a. Lab affordance 834a further includes date 834a3, which includes a visual and/or textual indicator of the date on which the corresponding lab type was updated.

Labs user interface 802b further includes absent indicator 832, which indicates a portion of labs user interface 802b containing information related to lab types that are not yet available at computer system 600 (e.g., lab types for which computer system 600 has not yet received lab results). In some embodiments, the portion of labs user interface 802b identified by absent indicator 832 includes one or more lab affordances corresponding to suggested lab types based on a determination that the suggested lab types relate to a currently selected health condition filter (e.g., "Diabetes"), and/or based on available (e.g., existing) lab results displayed by computer system 600. Labs user interface 802b further includes present indicator 830, which indicates a portion of labs user interface 802b containing information related to lab types that are available at computer system 600 (e.g., lab types for which computer system 600 has received lab results).

Labs user interface 802b further includes lab affordance 836a, which includes lab type 836a1, indicating that the corresponding lab type is "TSH." Lab affordance 836a further includes description 836a2 about the corresponding lab type. Notably, lab affordance 836a is displayed underneath absent indicator 832 to indicate that the lab type corresponding to lab affordance 836a (e.g., "TSH") is not in the records available to computer system 600. Thus, computer system 600 does not yet have "TSH" lab data available when labs user interface 802b is displayed. At FIG. 8B, computer system 600 receives input 850b (e.g., a tap input) on health condition filter 818b and, in response, displays labs user interface 802c.

In FIG. 8C, in response to receiving input 850b, computer system 600 displays labs user interface 802c. FIG. 8C illustrates computer system 600 displaying a labs user interface with a "Heart Health" health category filter selected. In some embodiments, updating the labs user interface to show health condition filter 818c being selected includes displaying a scrolling animation showing health condition filter 818c scrolling toward the left side of labs user interface 802c. Labs user interface 802c includes at least a portion of health condition filter 816c, which corresponds to "Diabetes," health condition filter 818c, which corresponds to "Heart Health," and health condition filter 838a, which corresponds to "Bone Health." In labs user interface 802c, health condition filter 816c includes a visual indication indicating that health condition filter 818c is currently selected (e.g., an outline). Labs user interface 802c includes lab data that corresponds to the selected "Heart Health" health condition filter (e.g., 818c). Labs user interface 802c includes education 828b about health condition filter 818c (e.g. "Heart Health").

Labs user interface 802c further includes lab data related to "Heart Health" in accordance with health condition filter 818c being selected. Labs user interface 802c further includes lab affordance 840a, which includes lab type 840a1, indicating that the corresponding lab type is "Cholesterol." Lab affordance 840a further includes value 840a2, which corresponds to a lab measurement (e.g., the most recent lab measurement) that corresponds to lab affordance 840a. Lab affordance 840a further includes date 840a3, which includes a visual and/or textual indicator of the date on which the corresponding lab type was updated.

Labs user interface 802c further includes lab affordance 842a, which includes lab type 842a1, indicating that the corresponding lab type is "Heart Rate." Lab affordance 842a further includes value 842a2, which corresponds to a lab measurement (e.g., the most recent lab measurement) that corresponds to lab affordance 842a. Lab affordance 842a further includes date 842a3, which includes a visual and/or textual indicator of the date on which the corresponding lab type was updated.

Labs user interface 802c further includes absent indicator 832, which indicates a portion of labs user interface 802c containing information related to lab types that are not yet available at computer system 600 (e.g., lab types for which computer system 600 has not yet received lab results). Labs user interface 802c includes lab affordance 844a, which includes lab type 844a1, indicating that the corresponding lab type is "Iron." Lab affordance 844 is displayed at least partially based on the corresponding lab type (e.g., "Iron") corresponding to the selected lab type (e.g., "Hearth Health").

Lab affordance 844a further includes description 844a2 about the corresponding lab type. Notably, lab affordance 844a is displayed underneath absent indicator 832 to indicate that the lab type corresponding to lab affordance 844a (e.g., "Iron") is not in the records available to computer system 600. Thus, computer system 600 does not yet have "Iron" lab data available when labs user interface 802c is displayed. Labs user interface 802c further includes time indicator 804a, which includes a visual and/or textual representation of a current time (e.g., 7:00 at FIG. 8C). Labs user interface 802c further includes back affordance 806 which, when selected, causes computer system 600 to display a previously displayed user interface screen. In FIG. 8C. computer system 600 receives input 850c (e.g., a tap input) on back affordance 806.

In FIG. 8D, in response to detecting input 850c, computer system 600 displays summary user interface 846a. Summary user interface 846a includes time indicator 804b, indicating that time has elapsed between FIG. 8C and FIG. 8D (e.g., from 7:00 to 10:09). Between 7:00 and 10:09, computer system receives lab data corresponding to the missing lab type indicated in FIG. 8C (e.g., "Iron"), and displays an update related to the new lab data as a result. Summary user interface 846a further includes labs update affordance 854a, which includes update indicator 854a1, which includes a visual and/or textual indicator that a labs data update is available. Labs update affordance 854a further includes update description 854a2 about the content of the labs data update.

Summary user interface 846a further includes health records update section 856a, which includes a visual and/or textual indicator that a health records update is available (e.g., the new "Iron" lab result). Summary user interface 846a further includes favorites indicator 858, which indicates a portion of summary user interface 846a where favorites information is displayed. Summary user interface 846a further includes measurement 862a1, which includes a visual representation of a first type of health-related information, and measurement 862a2, which includes a visual representation of a second type of health-related information. Summary user interface 846a further includes summary affordance 864 which, when selected, causes computer system 600 to display a summary user interface (e.g., 846a). At FIG. 8D, summary affordance 864 is displayed with a visually distinct appearance (e.g., bolded, outlined, and/or highlighted) to indicate that a summary user interface is currently being displayed and/or that summary affordance 864 is currently selected. Summary user interface 846a further includes sharing affordance 866 which, when selected, causes computer system 600 to display a user interface for sharing and/or transmitting information related to health data to other users. Summary user interface 846a further includes browse affordance 868 which, when selected, causes computer system 600 to display a user interface for browsing health-related information. Summary user interface 846a further includes avatar 852, which includes a graphical indicator corresponding to a user and/or a user account associated with computer system 600. At FIG. 8D, computer system 600 receives input 850d (e.g., a touch input) on labs update affordance 854a.

In FIG. 8E, in response to receiving input 850d, computer system 600 displays labs user interface 802d. Labs user interface 802d illustrates an updated version of labs user interface 802a after computer system 600 has received a new lab result. Labs user interface 802d includes health condition filter 814c, which corresponds to an "All" health filter, health condition filter 816d, which corresponds to "Diabetes," and health condition filter 818d, which corresponds to "Heart Health."

In FIG. 8E, lab user interface 802d includes a new lab affordance 844b that was not included in lab user interface 802a, indicating that the "Iron" lab result has been received. Labs affordance 844b includes lab type 844b1, indicating that the corresponding lab type is "Iron." Lab affordance 844b further includes value 844b2, which corresponds to a lab measurement (e.g., the most recent lab measurement) that corresponds to lab affordance 844b. Lab affordance 844b further includes date 844b3, which includes a visual and/or textual indicator of the date on which the corresponding lab type was updated. Lab affordance 844b corresponds to new lab data, as indicated by date 844b3, which indicates that the lab type was updated "Today." Further, lab affordance 844b corresponds to an updated view of lab affordance 844a, which indicated that lab data of the lab type "Iron" was unavailable, now that lab data corresponding to the lab type "Iron" is available.

Labs user interface 802a further includes pinned indicator 821, which indicates a portion of labs user interface 802d that corresponds to lab types that have been pinned (e.g., designated via a user input). Labs user interface 802d further includes delta highlight 820c, which includes content similar to delta highlight 820a, as discussed above.

Labs user interface 802d further includes lab affordance 824b, which includes content similar to lab affordance 824a, as discussed above. In FIG. 8E, computer system 600 receives input 850e (e.g., a tap input) on health condition filter 816d.

In FIG. 8F, in response to receiving input 850e, computer system 600 displays labs user interface 802e. FIG. 8F illustrates computer system 600 displaying a labs user interface with a "Diabetes" health category filter selected. Labs user interface 802e is an updated version of labs user interface 802b, wherein computer system 600 has received labs data corresponding to the "Iron" lab type. Lab user interface 802e includes at least a portion of health condition filter 814d, which allows all lab affordances to be displayed, health condition filter 816e, which corresponds to "Diabetes," and health condition filter 818e, which corresponds to "Heart Health." In labs user interface 802e, health condition filter 816e includes a visual indication indicating that health condition filter 816e is currently selected. Labs user interface 802e includes lab data that corresponds to the selected "Diabetes" health condition filter. Labs user interface 802e includes education 828a about health condition filter 816e (e.g. "Diabetes").

Labs user interface 802e further includes lab data related to "Diabetes" in accordance with health condition filter 816e being selected. Labs user interface 802e further includes delta highlight 820d, which includes content similar to delta highlight 820a, as discussed above. Labs user interface 802e further includes lab affordance 834b, which includes lab type 834b1, indicating that the corresponding lab type is "Fasting Glucose." Lab affordance 834b further includes value 834b2, which corresponds to a lab measurement (e.g., the most recent lab measurement) that corresponds to lab affordance 834b. Lab affordance 834b further includes date 834b3, which includes a visual and/or textual indicator of the date on which the corresponding lab type was updated. Labs user interface 802e further includes lab affordance 844c, which includes content similar to lab affordance 844b, as discussed above. At FIG. 8F, computer system 600 receives input 860b (e.g., swipe input) on labs user interface 802e and, in response, displays labs user interface 802f.

Figure 8G:
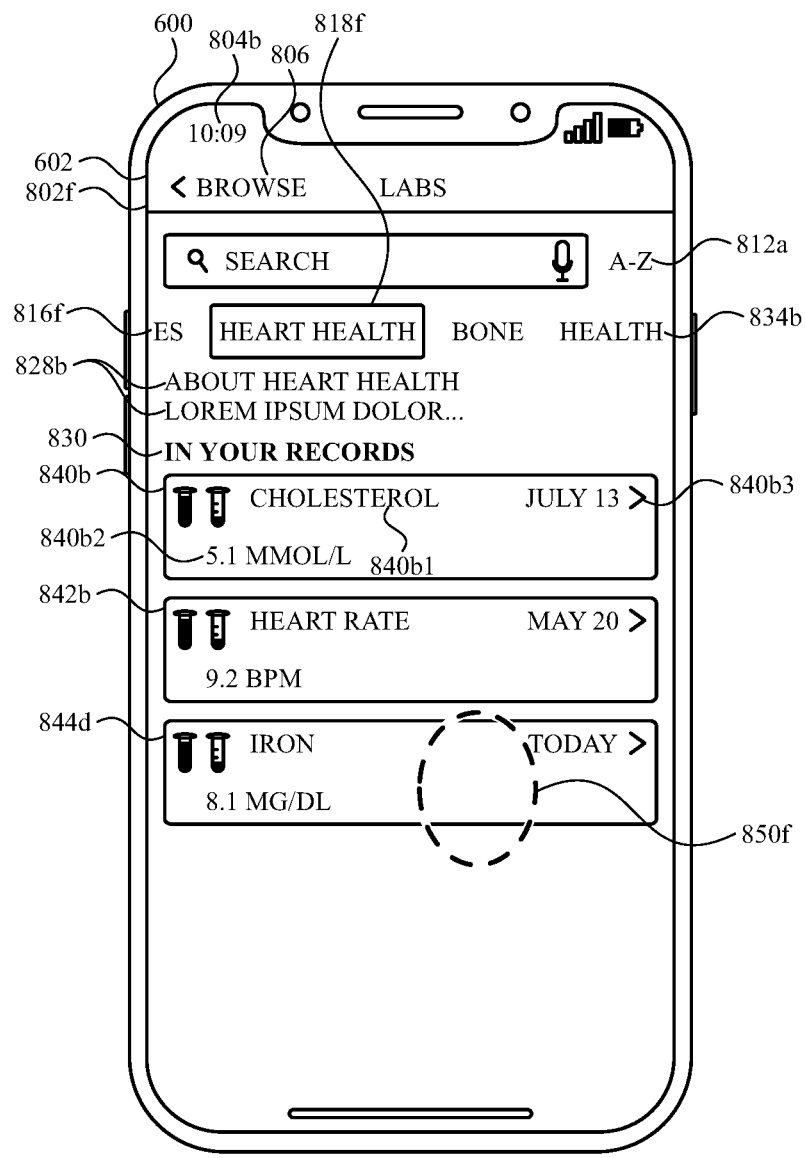
Figure 9:
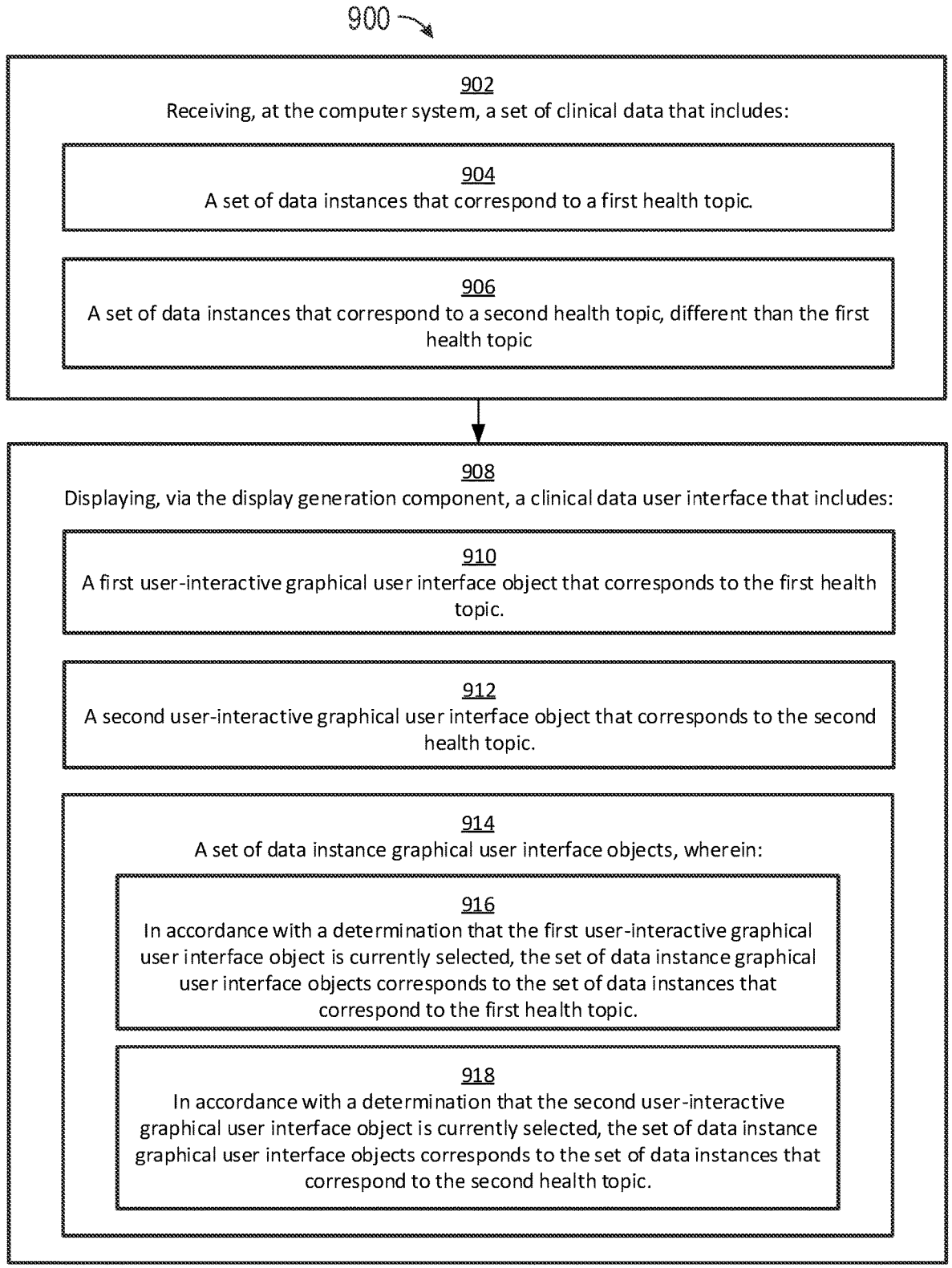
FIG. 9 is a flow diagram illustrating a method for displaying health topics using a computer system in accordance with some embodiments.

At FIG. 8G, in response to receiving input 860b, computer system 600 displays labs user interface 802f. FIG. 8G illustrates computer system 600 displaying a labs user interface with a "Heart Health" health category filter selected. Labs user interface 802f is an updated version of labs user interface 802c, wherein computer system 600 has received labs data corresponding to the "Iron" lab type. Labs user interface 802f includes at least a portion of health condition filter 816f, which corresponds to "Diabetes," health condition filter 818f, which corresponds to "Heart Health," and health condition filter 838b, which corresponds to "Bone Health." In labs user interface 802f, health condition filter 818f includes a visual indication indicating that health condition filter 818f is currently selected. Labs user interface 802f includes lab data that corresponds to the selected "Heart Health" health condition filter. Labs user interface 802f includes education 828b about health condition filter 818f (e.g. "Heart Health").

Labs user interface 802f further includes lab data related to "Heart Health" in accordance with health condition filter 818f being selected. Labs user interface 802f further includes lab affordance 840b, which includes lab type 840b1, indicating that the corresponding lab type is "Cholesterol." Lab affordance 840b further includes value 840b2, which corresponds to a lab measurement (e.g., the most recent lab measurement) that corresponds to lab affordance 840b. Lab affordance 840b further includes date 840b3, which includes a visual and/or textual indicator of the date on which the corresponding lab type was updated.

Labs user interface 802f further includes lab affordance 842b, which includes content to lab affordance 842b, as discussed above. Labs user interface 802f further includes lab affordance 844d, which includes content similar to lab affordance 844b, as discussed above. Notably, labs user interface 802f does not include absent indicator 832. Whereas labs user interface 802c indicated that lab results corresponding to the "Iron" lab type were unavailable and/or missing, lab affordance 844d indicates that lab results corresponding to the "Iron" lab type are now available. In some embodiments, computer system 600 foregoes displaying absent indicator 832 in accordance with a determination that computer system 600 has received and/or gained access to lab results corresponding to a lab type that were previously missing and/or absent. In FIG. 8G, computer system 600 receives input 850f (e.g., a tap input) on lab affordance 844d and, in response, displays lab room user interface 870.

Figure 8H:
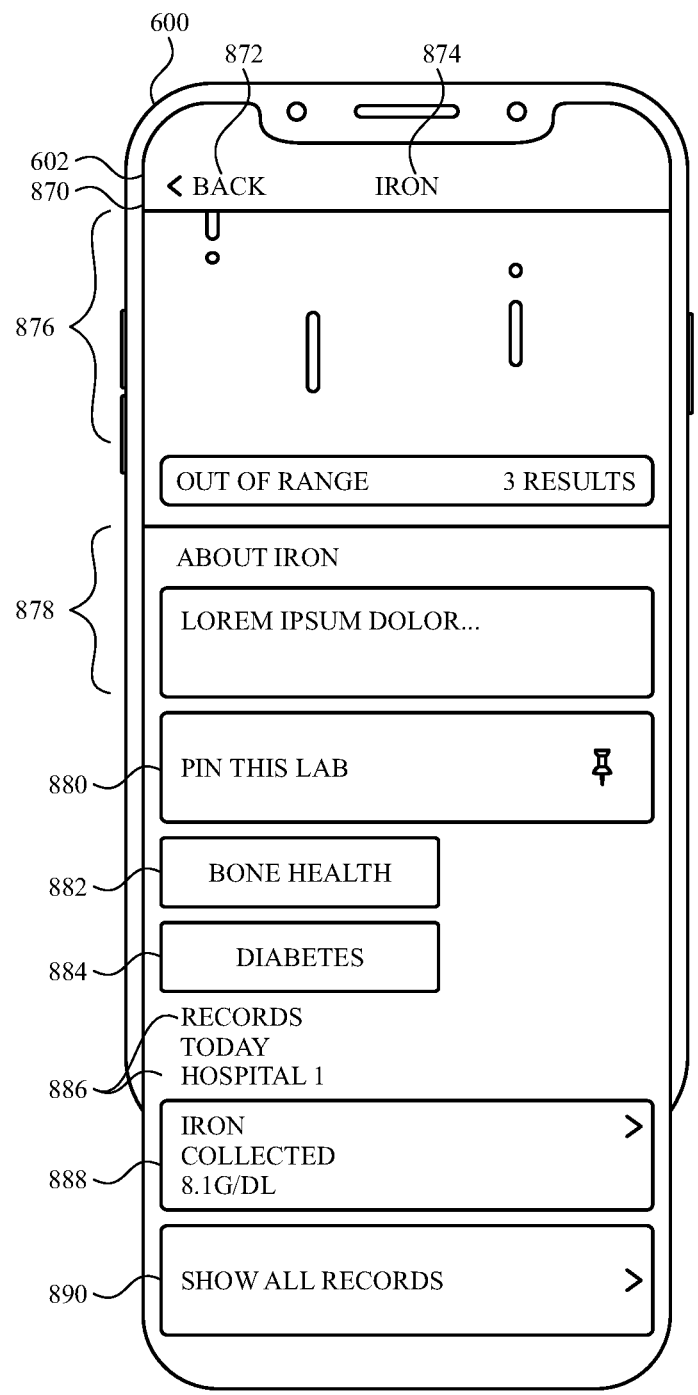

In FIG. 8H, in response to receiving input 850f, computer system 600 displays lab room user interface 870. FIG. 8H illustrates a user interface that includes labs data and/or results corresponding to a selected lab type (e.g., "Iron") that has not been pinned (e.g., has not been designated via a user input). Lab room user interface 870 further includes pin affordance 880 which, when selected, causes the lab type indicated by lab type 874 to be designated by a user input (e.g., pinned).

Lab room user interface 870 includes back affordance 872 which, when selected, causes computer system 600 to display a previous user interface that was displayed before lab room user interface 870 was displayed (e.g., labs user interface 802f). Lab room user interface 870 further includes lab type 874, which indicates the lab type to which lab room user interface 870 corresponds (e.g., "Iron"). Lab room user interface 870 further includes chart data 876, which includes graphs and/or charts corresponding to lab results corresponding to lab type 874. Lab room user interface 870 further includes education 878 about lab type 874 (e.g., common causes for getting labs related to lab type 874, physiological functions related to lab type 874). Lab room user interface 870 further includes records indicator 886, which includes a visual and/or textual indication of records data corresponding to one or more lab results corresponding to lab type 874. Lab room user interface 870 further includes lab affordance 888, which corresponds to a lab result of the lab type corresponding to lab type 874. Lab room user interface 870 further includes show all affordance 890 which, when selected, causes computer system 600 to display additional lab results corresponding to lab type 874 in lab room user interface 870.

Lab room user interface 870 further includes tag affordances related to lab type 874 that, when selected, cause computer system 600 to display information related to a particular health condition. Lab room user interface 870 includes tag affordance 882 which, when selected, causes computer system 600 to display a user interface including lab data related to "Bone Health." Lab room user interface 870 further includes tag affordance 884 which, when selected, causes computer system 600 to display a user interface including lab data related to "Diabetes" (e.g., labs user interface 802e).

Figure 8I:
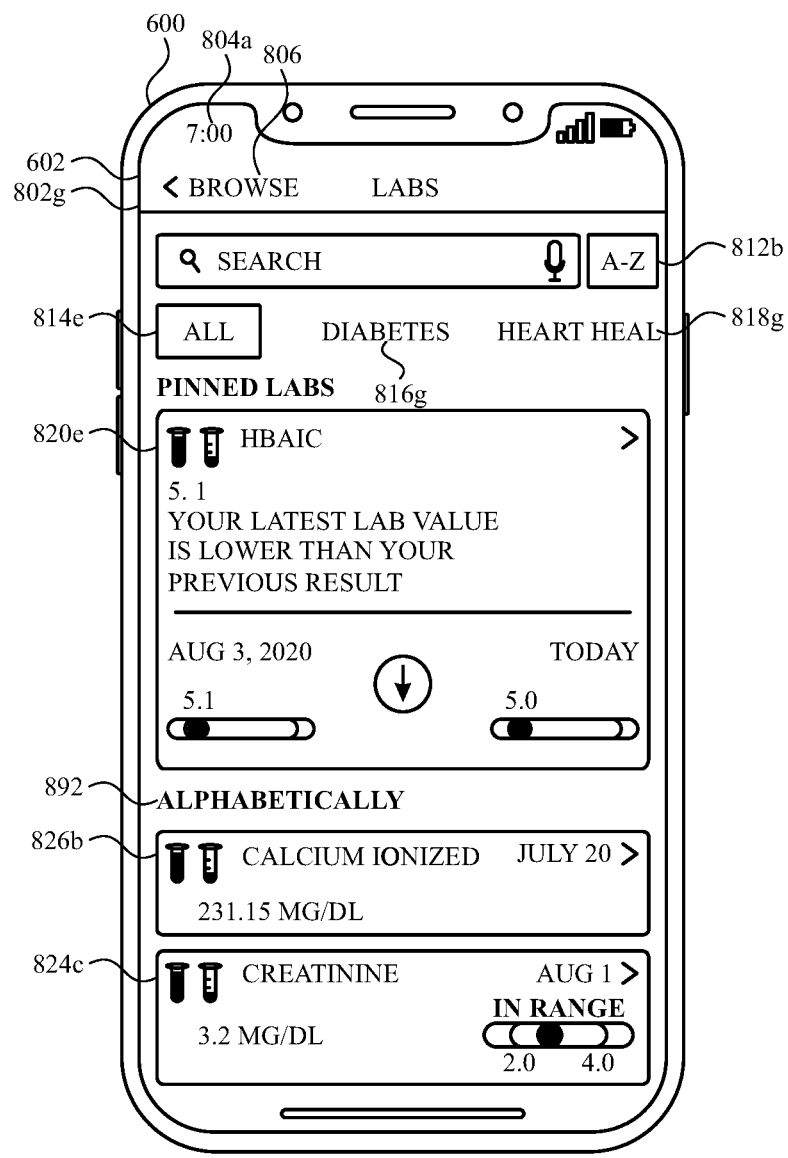

At FIG. 8I, in response to receiving input 850a as discussed in relation to FIG. 8A above, computer system displays labs user interface 802g. Labs user interface 802g is an updated version of labs user interface 802a wherein, in response to alphabetical sort option 812a being selected (e.g., via input 850*a*), lab data is displayed at least partially based on alphabetical order information (e.g., the labs data are sorted into alphabetical order). In FIG. 8I, labs user interface 802*g* includes alphabetical sort option 812*b*, which includes an outline that visually indicates that alphabetical sort option 812*b* is selected.

Labs user interface 802*g* further includes pinned indicator 821, which indicates a portion of labs user interface 802*g* that corresponds to lab types that have been pinned (e.g., designated via a user input). Labs user interface 802*g* further includes delta highlight 820*e*, which includes content similar to delta highlight 820*a*, as discussed above. Labs user interface 802*e* further includes alphabetical order indicator 892, which includes a visual and/or textual indicator that the lab data displayed below alphabetical order indicator 892 is sorted into alphabetical order. Labs user interface 802*g* further includes lab affordance 824*c*, which content similar to lab affordance 824*a*, as discussed above. Labs user interface 802*g* further includes lab affordance 826*b*, which content similar to lab affordance 826*a*, as discussed above.

Notably, lab affordance 826*b* is displayed above lab affordance 824*c* because the lab results are sorted into alphabetical order based on their corresponding lab types (e.g., "Calcium Ionized" and "Creatinine"). However, pinned lab types (e.g., "HbA1c") are displayed in a separate portion of labs user interface 802*g* than unpinned lab types (e.g., "Calcium Ionized" and "Creatinine"), and are sorted (e.g., alphabetically) separately (e.g., within the separate portion of labs user interface 802*g*).

Labs user interface 802*g* includes health condition filter 814*e*, allows all lab affordances to be displayed, health condition filter 816*g*, which corresponds to "Diabetes," and health condition filter 818*g*, which corresponds to "Heart Health."

FIG. 9 is a flow diagram illustrating a method for displaying health topics using a computer system in accordance with some embodiments. Method 900 is performed at a computer system (e.g., 100, 300, 500) (e.g., a wearable electronic device (e.g., a smartwatch), a smartphone, a desktop computer, a laptop, a tablet) that is in communication with a display generation component and one or more input devices (e.g., a display controller, a touch-sensitive display system, a rotatable input mechanism, a touch-sensitive surface). Some operations in method 900 are, optionally, combined, the orders of some operations are, optionally, changed, and some operations are, optionally, omitted.

As described below, method 900 provides an intuitive way for displaying health topics. The method reduces the cognitive burden on a user for reviewing and managing health topics, thereby creating a more efficient human-machine interface. For battery-operated computing devices, enabling a user to view health topics faster and more efficiently conserves power and increases the time between battery charges.

The computer system (e.g., 600) receives (e.g., 902), at the computer system, a set of clinical data (e.g., physiological measurements, lab results, health data, medical data (e.g., blood glucose, creatinine, iron, LDL cholesterol)) that includes: a set of data instances (e.g., one or more datum) (e.g., 904) that correspond to a first health topic (e.g., a medical condition, a health concern, a diagnosis, a symptom, and/or a risk factor), and a set of data instances (e.g., 906) that correspond to a second health topic, different than the first health topic. In some embodiments, the one or more data instances that correspond to the first health topic do not correspond to the second health topic. In some embodiments, the one or more data instances include at least one data instance that corresponds to at least the first and second health topics.

The computer system (e.g., 600) displays (e.g., 908), via the display generation component (e.g., 602), a clinical data user interface (e.g., 802*a*) that includes: a first user-interactive graphical user interface object (e.g., an affordance; a first topic filter) (e.g., 816*a*) (e.g., 910) that corresponds to the first health topic, a second user-interactive graphical user interface object (e.g., an affordance; a second health topic filter) (e.g., 818*a*) (e.g., 912) that corresponds to the second health topic, and a set of data instance graphical user interface objects (e.g., 914) (e.g., 820*a*, 824*a*, 826*a*).

In accordance with a determination (e.g., 916) that the first user-interactive graphical user interface object (e.g., 816*b*) is currently selected (e.g., currently in focus, highlighted, bolded), the set of data instance graphical user interface objects (e.g., 820*b*, 834*a*) corresponds to (e.g., each user interface object in the set of data instance graphical user interface objects represents a single data instance in the set of data instances) the set of data instances that correspond to the first health topic. In some embodiments, while the first user-interactive graphical user interface object is currently selected, data instances that do not correspond to the first health topic are not displayed (e.g., are filtered out). In some embodiments, the first user-interactive graphical user interface object and the second user-interactive graphical user interface object cannot both be selected at the same time (e.g., selecting one (or selecting another filter) de-selects the other).

In accordance with a determination (e.g., 918) that the second user-interactive graphical user interface object (e.g., 818*c*) is currently selected, the set of data instance graphical user interface objects (e.g., 840*a*, 842*a*) corresponds to the set of data instances that correspond to the second health topic. In some embodiments, the set of data instances that correspond to the first health topic and/or the set of data instances that correspond to the second health topic include data instances related to test results, lab results, and/or physiological measurements. Displaying the set of data instance graphical user interface objects that correspond to a health topic when a user-interactive graphical user interface object corresponding to that health topic is selected provides visual feedback about the set of data instance graphical user interface objects that correspond to a given health topic. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently. Further, displaying the set of data instance graphical user interface objects that correspond to a health topic when a user-interactive graphical user interface object corresponding to that health topic is selected enables a user to quickly and easily limit the set of data instance graphical user interface objects displayed to correspond to the given health topic without requiring the user to manually sort through and/or remove data instance graphical user interface objects that do not correspond to the health topic. Performing an operation when a set of conditions has been met without requiring further user input enhances the operability of the device and makes the user-device interface more efficient (e.g., by display information corresponding to a particular health topic) which, additionally, reduces power usage and improves battery life of the device by enabling the user to use the device more quickly and efficiently.

In some embodiments, the computer system (e.g., 600) receives, at the computer system, a second set of clinical data that includes a first data instance. In some embodiments, after receiving the second set of clinical data, the computer system displays the clinical data user interface (e.g., 802*b*), wherein displaying the clinical data user interface includes: in accordance with a determination that the first user-interactive graphical user interface object (e.g., 816*b*) is currently selected and that the first data instance corresponds to the first health topic, the computer system displays a first data instance graphical user interface object (e.g., 820*b*) that corresponds to the first data instance. In some embodiments, in accordance with a determination that the second user-interactive graphical user interface object (e.g., 818*c*) is currently selected and that the first data instance corresponds to the second health topic, the computer system displays the first data instance graphical user interface object that corresponds to the first data instance. In accordance with a determination that the first data instance corresponds to a third health topic different from the first health topic and the second health topic, the computer system displays a third user-interactive graphical user interface object (e.g., an affordance; a third topic filter) (e.g., 838*a*) that corresponds to the third health topic. In some embodiments, displaying the clinical data user interface includes, in accordance with a determination that the third user-interactive graphical user interface object is currently selected and that the first data instance corresponds to the third health topic, displaying the first data instance graphical user interface object that corresponds to the first data instance. Displaying a data instance graphical user interface object that corresponds to a received data instance in accordance with a determination that the data instance corresponds to a currently selected user-interactive graphical user interface object (e.g., a health topic filter) enables newly added data instances to quickly be sorted and displayed with their corresponding health topics without requiring the user to manually sort and/or add received data instances to health topics. Performing an operation when a set of conditions has been met without requiring further user input enhances the operability of the device and makes the user-device interface more efficient (e.g., by displaying information in a sorted order) which, additionally, reduces power usage and improves battery life of the device by enabling the user to use the device more quickly and efficiently.

In some embodiments, the set of data instance graphical user interface objects includes a second data instance graphical user interface object (e.g., 820*b*), wherein the second data instance graphical user interface object includes a graphical indication (e.g., 820*b*3) of a difference between a first value (e.g., a current value) corresponding to the second data instance graphical user interface object and a second value (e.g., a previous value) corresponding to the second data instance graphical user interface object. In some embodiments, the graphical indication includes an up arrow if the first value is greater than the second value. In some embodiments, the graphical indication includes a down arrow if the first value is less than the second value. In some embodiments, the graphical indication includes a horizontal line if the first value and the second value are equal. Displaying a graphical indication of a difference between two values corresponding to a data instance graphical user interface object provides improved visual feedback about the overall trend (e.g., trajectory) of values related to the data instance graphical user interface object. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, the set of data instance graphical user interface objects includes a third data instance graphical user interface object (e.g., 844*c*), wherein the third data instance graphical user interface object corresponds to a first data instance of a first type (e.g., a first lab type, a first lab test provider) and a second data instance of a second type (e.g., a second lab type, a first lab test provider). Displaying a data instance graphical user interface object that corresponds to multiple data instances enables the user to quickly and easily view aggregated data related to a first data instance and a second instance by viewing and/or interacting with (e.g., selecting) the data instance graphical user interface object, thereby reducing the number of inputs required to view data related to a first data instance and a second data instance. Reducing the number of inputs needed to perform an operation enhances the operability of the system and makes the computer system more efficient (e.g., by helping the user to quickly and easily view aggregated labs data) which, additionally, reduces power usage and improves battery life of the device by enabling the user to use the system more quickly and efficiently.

In some embodiments, the set of data instance graphical user interface objects includes a fourth data instance graphical user interface object (e.g., 844*d*). In some embodiments, while displaying the clinical data user interface (e.g., 802*f*), the computer system (e.g., 600) receives a user input (e.g., a tap input) (e.g., 850*f*) corresponding to selection of the fourth data instance graphical user interface object. In some embodiments, in response to receiving the user input corresponding to selection of the fourth data instance graphical user interface object, the computer system displays a lab user interface (e.g., 870) corresponding to the fourth data instance graphical user interface object, wherein the lab user interface includes a fifth user-interactive graphical user interface object (e.g., an affordance; a first topic filter) (e.g., 884) that corresponds to a sixth health topic. In some embodiments, while displaying the lab user interface, the computer system receives a user input corresponding to selection of the fifth user-interactive graphical user interface object. In some embodiments, in response to receiving the user input corresponding to selection of the fifth user-interactive graphical user interface object, the computer system displays the clinical data user interface (e.g., 802*e*) wherein the set of data instance graphical user interface objects corresponds to the set of data instances that correspond to the sixth health topic. Displaying a clinical data user interface including information corresponding to a health topic in response to selecting a user-interactive graphical user interface object enables the user to quickly and easily view clinical data related to a health topic, thereby reducing the number of inputs required to view data related to a health topic. Reducing the number of inputs needed to perform an operation enhances the operability of the system and makes the computer system more efficient (e.g., by helping the user to quickly and easily view clinical data related to a health topic) which, additionally, reduces power usage and improves battery life of the device by enabling the user to use the system more quickly and efficiently.

In some embodiments, the first user-interactive graphical user interface object (e.g., 816*a*) and the second user-interactive graphical user interface object (e.g., 818a) are aligned along a first axis (e.g., arranged in the clinical data user interface in a first direction (e.g., left to right)), and the set of data instance graphical user interface objects (e.g., 820a, 824a, 826a) is aligned along a second axis different from the first axis (e.g., arranged in the clinical data user interface in a second direction (e.g., top to bottom)). Aligning the filter user-interactive graphical user interface objects along a first axis and the set of data instance graphical user interface objects provides visual feedback about the different nature of the different on-screen elements and, in some embodiments, provides visual feedback that the different types of onscreen elements can be scrolled in two different directions corresponding to their alignment. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, while the first user-interactive graphical user interface object (e.g., 816b) is currently selected, and while the set of data instance graphical user interface objects that corresponds to the set of data instances that correspond to the first health topic (e.g., 820b, 834a) is displayed, the computer system (e.g., 600) receives a first user input (e.g., 850b). In some embodiments, in response to receiving the first user input, the computer system selects the second user-interactive graphical user interface object (e.g., 818b). In some embodiments, in response to receiving the first user input, the computer system modifies (e.g., modifying the display of (e.g., appearance of)) the set of data instance graphical user interface objects to correspond to the set of data instances that correspond to the second health topic. Displaying the set of data instance graphical user interface objects that correspond to a selected user-interactive graphical user interface object based on a swipe input enables the user to quickly and easily view data instance graphical user interface objects related to the selected user-interactive graphical user interface object (e.g., the health filter) without requiring the user to manually sort through and/or locate related data instance graphical user interface objects. Performing an operation when a set of conditions has been met without requiring further user input enhances the operability of the device and makes the user-device interface more efficient (e.g., by filtering information according to a health topic) which, additionally, reduces power usage and improves battery life of the device by enabling the user to use the device more quickly and efficiently.

In some embodiments, displaying the clinical data user interface (e.g., 802c) includes concurrently displaying a third user-interactive graphical user interface object (e.g., 842a) that includes a first visual representation (e.g., 842a2) of data collected via a physiological measurement sensor (e.g., a heart rate sensor, a VO2 max sensor). In some embodiments, in response to receiving a user input corresponding to selection of the third user-interactive graphical user interface object, the computer system displays a sensor user interface including additional data from the physiological measurement sensor. Including a visual representation of data collected via a physiological measurement sensor in the clinical data user interface enables the user to quickly and easily view physiological measurement sensor data while viewing other clinical data, thereby reducing the number of inputs required to switch back and forth between clinical data retrieved from elsewhere (e.g., hospital, a laboratory) and physiological measurement sensor data. Reducing the number of inputs needed to perform an operation enhances the operability of the system and makes the computer system more efficient (e.g., by helping the user to quickly and easily view physiological measurement sensor data while viewing other clinical data) which, additionally, reduces power usage and improves battery life of the device by enabling the user to use the system more quickly and efficiently.

In some embodiments, in accordance with a determination that the first user-interactive graphical user interface object (e.g., 816b) is currently selected (e.g., currently in focus, highlighted, bolded), the clinical data user interface (e.g., 802b) includes chart data (e.g., a chart and/or graph that includes data related to the first health topic) that corresponds to the first health topic. In some embodiments, in accordance with a determination that the second user-interactive graphical user interface object is currently selected (e.g., 818c), the clinical data user interface (e.g., 802c) includes chart data (e.g., a chart and/or graph that includes data related to the first health topic) that corresponds to the second health topic. In some embodiments, the first user-interactive graphical user interface object and the second user-interactive graphical user interface object cannot both be selected at the same time (e.g., selecting one (or selecting another filter) de-selects the other. Displaying chart data that corresponds to a first health topic or a second health topic in accordance with a determination about which health topic filter is selected enables the user to quickly and easily view chart data related to a health topic, thereby reducing the number of inputs required to view chart data related to a selected health topic filter. Reducing the number of inputs needed to perform an operation enhances the operability of the system and makes the computer system more efficient (e.g., by helping the user to quickly and easily view chart data related to a health topic) which, additionally, reduces power usage and improves battery life of the device by enabling the user to use the system more quickly and efficiently.

In some embodiments, in accordance with a determination that the first user-interactive graphical user interface object (e.g., 816b) is currently selected, the clinical data user interface (e.g., 802b) includes a set of information (e.g., a textual description of the scope significance of the first health topic) (e.g., 828a) that corresponds to the first health topic. In some embodiments, in accordance with a determination that the second user-interactive graphical user interface object (e.g., 818c) is currently selected, the clinical data user interface (e.g., 802c) includes a set of information (e.g., 828b) that corresponds to the second health topic (e.g., a textual description of the scope significance of the second health topic). In some embodiments, the set of information related to a health topic includes information related to one or more of a set of data instance graphical user interface objects included in the clinical data user interface. Displaying information that corresponds to a first health topic or a second health topic in accordance with a determination about which health topic filter is selected enables the user to quickly and easily view education data related to a health topic, thereby reducing the number of inputs required to view chart data related to a selected health topic filter. Reducing the number of inputs needed to perform an operation enhances the operability of the system and makes the computer system more efficient (e.g., by helping the user to quickly and easily view education data related to a health topic) which, additionally, reduces power usage and improves battery life of the device by enabling the user to use the system more quickly and efficiently.

In some embodiments, in accordance with a determination that the first user-interactive graphical user interface object is currently selected (e.g., 816*b*), and that the computer system (e.g., 600) has not received one or more data instances corresponding to a first lab type that corresponds to (e.g., is clinically associated with (e.g., blood glucose for diabetes)) the first health topic, the computer system displays a first visual indicator (e.g., 836*a*) corresponding to the first lab type (e.g., a textual and/or graphical indication that the computer system has not yet received data corresponding to the first lab type, a suggestion to add a data instance corresponding to the first lab type). In some embodiments, in accordance with a determination that the second user-interactive graphical user interface object (e.g., 818*c*) is currently selected, and that the computer system has not received one or more data instances corresponding to a second lab type that corresponds the second health topic, the computer system displays a second visual indicator (e.g., 844*a*) corresponding to the second lab type. In some embodiments, the first lab type and the second lab type are different. In some embodiments, the first visual indicator and the second visual indicator are different. Displaying a visual indicator corresponding to a lab type in accordance with a determination that a health topic filter corresponding to the lab type is selected, and that the computer system has not received a data instance corresponding to the lab type provides visual feedback about potentially missing lab types that correspond to a health topic that is being viewed. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, while displaying the clinical data user interface (e.g., 802*f*), the computer system receives a second user input (e.g., a tap input) (e.g., 850*f*) corresponding to selection of a data instance graphical user interface object (e.g., 844*d*) of (e.g., included in) the set of graphical user interface objects. In some embodiments, in response to receiving the second user input, the computer system displays a second lab user interface (e.g., 870), wherein the second lab user interface includes: a third visual indicator corresponding to one or more data instances (e.g., one or more datum) (e.g., 888) corresponding to the data instance graphical user interface object of the set of graphical user interface objects and a fourth user-interactive graphical user interface object (e.g., an affordance; a fourth topic filter) that corresponds to a fourth health topic (e.g., 882, 884). Displaying a user-interactive graphical user interface object that corresponds to a fourth health topic in a lab user interface provides visual feedback about a health topic that potentially related to the is being viewed. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, the set of clinical data includes a fourth data instance (e.g., 834*b*) that corresponds to the first health topic and does not correspond to the second health topic. Maintaining a set of clinical data that includes data instances that correspond to different health topics enables features of the set of clinical data to be displayed concurrently, aggregated, and/or sorted by criteria, thereby reducing the number of inputs required to navigate among disparate sets of data sets related to different health topics. Reducing the number of inputs needed to perform an operation enhances the operability of the system and makes the computer system more efficient (e.g., by helping the user to quickly and easily navigate among disparate sets of data sets related to different health topics) which, additionally, reduces power usage and improves battery life of the device by enabling the user to use the system more quickly and efficiently.

In some embodiments, the set of clinical data includes a fifth data instance (e.g., 844*c*, 844*d*) that corresponds to the first health topic and the second health topic. Including a data instance that corresponds to a first health topic and a second health topic in the set of clinical data enables related to the data instance to be displayed in multiple user interfaces corresponding to both corresponding health topics, thereby reducing the number of inputs required to choose a corresponding health topic for a data instance that could correspond to two or more health topics. Reducing the number of inputs needed to perform an operation enhances the operability of the system and makes the computer system more efficient (e.g., by helping the user to quickly and easily choose a corresponding health topic for a data instance that could correspond to two or more health topics) which, additionally, reduces power usage and improves battery life of the device by enabling the user to use the system more quickly and efficiently.

In some embodiments, while displaying the clinical data user interface (e.g., 802*a*), the computer system (e.g., 600) receives a first set of one or more user inputs that includes an input for adding a fifth health topic. In some embodiments, in response to receiving the first set of one or more user inputs, the computer system updates the clinical data user interface to include a user-interactive graphical user interface object that corresponds to the fifth health topic. Updating the clinical user interface to include a user-interactive graphical user interface object that corresponds to a health topic in response to receiving a set of user inputs enables a user to quickly and easily add a health topic while the clinical data user interface is displayed, thereby reducing the number of inputs required to choose a corresponding health topic for a data instance that could correspond to two or more health topics. Reducing the number of inputs needed to perform an operation enhances the operability of the system and makes the computer system more efficient (e.g., by helping the user to quickly and easily add a health topic while the clinical data user interface is displayed) which, additionally, reduces power usage and improves battery life of the device by enabling the user to use the system more quickly and efficiently.

In some embodiments, while displaying the clinical data user interface (e.g., 802*a*), the computer system (e.g., 600) receives a second set of one or more user inputs that includes an input for removing the first health topic. In some embodiments, in response to receiving the second set of one or more user inputs, the computer system updates the clinical data user interface to not include the first user-interactive graphical user interface object that corresponds to the first health topic (e.g., to exclude the first health topic). Updating the clinical user interface to not include (e.g., to exclude) a user-interactive graphical user interface object that corresponds to a health topic in response to receiving a set of user inputs enables a user to quickly and easily remove a health topic while the clinical data user interface is displayed, thereby reducing the number of inputs required to choose a corresponding health topic for a data instance that could correspond to two or more health topics. Reducing the number of inputs needed to perform an operation enhances the operability of the system and makes the computer system more efficient (e.g., by helping the user to quickly and easily remove a health topic while the clinical data user interface is displayed) which, additionally, reduces power usage and improves battery life of the device by enabling the user to use the system more quickly and efficiently.

In some embodiments, displaying the clinical data user interface (e.g., 802a) includes concurrently displaying a sort user-interactive graphical user interface object (e.g. 812a) that, when selected, causes the set of data instance graphical user interface objects to be displayed within the clinical data user interface based on at least a first sorting criteria (e.g., alphabetically, chronically). Displaying a sort user-interactive graphical user interface object that, when selected, causes the set of data instance graphical user interface objects to be sorted enables the user to quickly and easily cause the data instance graphical user objects to be sorted without sorting them manually, thereby reducing the number of inputs required to sort the data instance graphical user interface objects. Reducing the number of inputs needed to perform an operation enhances the operability of the system and makes the computer system more efficient (e.g., by helping the user to quickly and easily cause the data instance graphical user interface objects to be sorted) which, additionally, reduces power usage and improves battery life of the device by enabling the user to use the system more quickly and efficiently.

In some embodiments, in accordance with a determination that a first subset of the set of data instance graphical user interface objects (e.g., 820c) has been (e.g., was previously) designated (e.g., pinned, selected) via a user input (e.g., via a tap input, a press input, and/or a swipe input) received via the one or more input devices, the computer system (e.g., 600) displays, via the display generation component (e.g., 600), the first subset of the set of data instance graphical user interface objects (e.g., 820c) in a first portion of the clinical data user interface (e.g., 802a) (e.g., a portion of the clinical data user interface for data instance graphical user interface objects that have been designated (e.g., pinned)) (e.g., 802g). In some embodiments, in accordance with a determination a second subset of the set of data instance graphical user interface objects (e.g., 826b, 824c) different from the first subset of the set of data instance graphical user interface objects has not been (e.g., was not previously) designated (e.g., pinned, selected) via a user input (e.g., via a tap input, a press input, and/or a swipe input) received via the one or more input devices, the computer system displays, via the display generation component (e.g., 602), the second subset of the set of data instance graphical user interface objects in a second portion of the clinical data user interface (e.g., a portion of the clinical data user interface for data instance graphical user interface objects that have not been designated (e.g., pinned)) (e.g., 802g) different from the first portion of the clinical data user interface. In some embodiments, in accordance with a determination that a data instance graphical user interface object included in the first subset of the set of data instance graphical user interface objects has been (e.g., was previously) designated (e.g., pinned, selected) via a user input (e.g., via a tap input, a press input, and/or a swipe input) received via the one or more input devices, the graphical user interface object included in the first subset of the set of data instance graphical user interface objects includes a graphical indication (e.g., an up arrow (e.g., in a first color), a down arrow (e.g., in a second color different from the first color), and/or a horizontal line) of a difference (e.g., an increase, a decrease, an indication of a no change, an indication of a change, a delta) between a first value (e.g., numerical value corresponding to a physiological measurement and/or reading corresponding to a first lab data instance) corresponding to the graphical user interface object included in the first subset of the set of data instance graphical user interface objects and at least a second value (e.g., a physiological measurement and/or a reading corresponding to a second lab data instance different from the first lab data instance) corresponding to the graphical user interface object included in the first subset of the set of data instance graphical user interface objects; In some embodiments, in accordance with a determination that a data instance graphical user interface object included in the second subset of the set of data instance graphical user interface objects has not been designated via a user input (e.g., via any previous user input; the first lab type is currently not a designated/selected/pinned lab type), displaying, via the display generation component, the data instance graphical user interface object included in the second subset of the set of data instance graphical user interface objects without a graphical indication of the difference between a first value corresponding to the data instance graphical user interface object included in the second subset of the set of data instance graphical user interface objects and at least a second value corresponding to the data instance graphical user interface object included in the second subset of the set of data instance graphical user interface objects. Displaying subsets of the set of data instance graphical user interface objects in either a first portion or a second portion of the clinical data user interface in accordance with a determination about whether they have been previously designated via a user input provides visual feedback about which of the data instance graphical user interface objects have been previously designated via a user input. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

Note that details of the processes described above with respect to method 900 (e.g., FIG. 9) are also applicable in an analogous manner to the methods described below. For example, method 700 optionally includes one or more of the characteristics of the various methods described above with reference to method 900. For example, the data instances described above could be displayed in particular portions of the user interfaces in which they are included in accordance with a determination about whether the data instances (or corresponding health topics or lab types) has been previously designated via a user input. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to allow users to view and manage relevant clinical, health-related, and/or physiological data. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to display user-specific clinical, health-related, or physiological measurements data. Accordingly, use of such personal information data enables users to be able to view and manage themselves, or of users who have shared corresponding data. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of clinical, health-related, or physiological measurements data, the present technology can be configured to allow users to select to "opt in" or "opt out" of participation in the collection of personal information data during registration for services or anytime thereafter. In another example, users can select not to provide clinical, health-related, or physiological measurements data for targeted content delivery services. In yet another example, users can select to limit the length of time clinical, health-related, or physiological measurements data is maintained or entirely prohibit the storing or maintaining of clinical, health-related, or physiological measurements data. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, clinical, health-related, and physiological measurements data can be displayed by inferring preferences based on non-personal information data or a bare minimum amount of personal information, such as the content being requested by the device associated with a user, other non-personal information available to the computer system, or publicly available information.

What is claimed is:

1. A computer system configured to communicate with a display generation component and one or more input devices, comprising:
   one or more processors; and
   memory storing one or more programs configured to be executed by the one or more processors, the one or more programs including instructions for:
   receiving, via the one or more input devices, a request to display a first user interface that includes a first user-interactive graphical user interface object corresponding to a first lab type, wherein the first lab type has not been designated by a user input; and in response to receiving the request to display the first user interface, displaying, via the display generation component, the first user interface that includes the first user-interactive graphical user interface object corresponding to the first lab type, wherein the first user-interactive graphical user interface object does not include a graphical indication of a difference between a first value corresponding to the first lab type and at least a second value corresponding to the first lab type;

after displaying the first user interface, displaying, via the display generation component, a second user interface that includes a second user-interactive graphical interface object corresponding to the first lab type and a third user-interactive graphical user interface object corresponding to a second lab type;

while displaying the second user interface, receiving, via the one or more input devices, a user input designating a lab type;

after receiving the user input designating a lab type, receiving, via the one or more input devices, a second request to display the first user interface that includes the first user-interactive graphical user interface object corresponding to the first lab type; and in response to receiving the second request to display the first user interface, displaying, via the display generation component, the first user interface that includes the first user-interactive graphical user interface object corresponding to the first lab type, wherein:

in accordance with a determination that the first lab type has been designated via a user input, the first user-interactive graphical user interface object includes the graphical indication of the difference between the first value corresponding to the first lab type and at least the second value corresponding to the first lab type; and in accordance with a determination that the first lab type has not been designated via a user input, the first user-interactive graphical user interface object does not include the graphical indication of the difference between the first value corresponding to the first lab type and at least the second value corresponding to the first lab type.

2. The computer system of claim 1, wherein:

in accordance with a determination that the first value corresponding to the first lab type is greater than the second value corresponding to the first lab type, the graphical indication has a first appearance;

in accordance with a determination that the first value corresponding to the first lab type is less than the second value corresponding to the first lab type, the graphical indication has a second appearance different than the first appearance; and in accordance with a determination that the first value corresponding to the first lab type is equal to the second value corresponding to the first lab type, the graphical indication has a third appearance different from the first appearance and the second appearance.

3. The computer system of claim 1, wherein the computer system is associated with a first user account, the one or more programs further including instructions for:

while performing a process to configure health-related data for sharing with a second user account, displaying a sharing data selection user interface, wherein displaying the sharing data selection user interface includes:

in accordance with a determination that the first lab type has been designated via the user input, displaying a second user-interactive graphical user interface object that, when selected, causes data of the first lab type to be shared with the second user account upon completion of the process to configure health-related data for sharing with a second user account; and in accordance with a determination that the first lab type has not been designated via the user input, forgoing displaying the second user-interactive graphical user interface object that, when selected, causes data of the first lab type to be shared with the second user account upon completion of the process to configure health-related data for sharing with a second user account.

4. The computer system of claim 3, the one or more programs further including instructions for:

during the process to configure health-related data for sharing with a second user account, displaying a lab type sharing selection user-interactive graphical user interface object;

receiving an input corresponding to the lab type sharing selection user-interactive graphical user interface object;

in response to receiving the input corresponding to the lab type sharing selection user-interactive graphical user interface object, displaying:

a third user-interactive graphical user interface object that, when selected, modifies whether data of the first lab type will be shared with the second user account upon completion of the process to configure health-related data for sharing with a second user account; and a fourth user-interactive graphical user interface object that, when selected, modifies whether data of a third lab type will be shared with the second user account upon completion of the process to configure health-related data for sharing with a second user account.

5. The computer system of claim 1, wherein the user input designating the lab type is selected from the group consisting of:

a sustained input of greater than a predetermined time on the second user-interactive graphical user interface object, an input, which includes movement in a first direction, that corresponds to the second user-interactive graphical user interface object, and a set of one or more inputs that includes a first input corresponding to the second user-interactive graphical user interface object.

6. The computer system of claim 1, the one or more programs further including instructions for:

in accordance with a determination that the first lab type has been designated via a user input received via the one or more input devices, including the second user-interactive graphical user interface object corresponding to the first lab type in a first set of one or more user-interactive graphical user interface objects that are displayed, via the display generation component, in a first portion of the second user interface; and in accordance with a determination that the first lab type has not been designated via a user input, displaying, via the display generation component, the second user-interactive graphical user interface object corresponding to the first lab type in a second set of one or more user-interactive graphical user interface objects that are displayed, via the display generation component, in a second portion of the second user interface.

7. The computer system of claim 6, wherein:
the first set of one or more user-interactive graphical user interface objects are sorted in the first portion of the second user interface according to a first sorting criteria, and
the second set of one or more user-interactive graphical user interface objects are sorted in the second portion of the second user interface according to a second sorting criteria.

8. The computer system of claim 1, wherein the second user interface includes an edit user-interactive graphical user interface object that, when selected, initiates a process for modifying a designation state of the first lab type.

9. A non-transitory computer-readable storage medium storing one or more programs configured to be executed by one or more processors of a computer system that is in communication with a display generation component and one or more input devices, the one or more programs including instructions for:
receiving, via the one or more input devices, a request to display a first user interface that includes a first user-interactive graphical user interface object corresponding to a first lab type, wherein the first lab type has not been designated by a user input; and
in response to receiving the request to display the first user interface, displaying, via the display generation component, the first user interface that includes the first user-interactive graphical user interface object corresponding to the first lab type, wherein the first user-interactive graphical user interface object does not include a graphical indication of a difference between a first value corresponding to the first lab type and at least a second value corresponding to the first lab type;
after displaying the first user interface, displaying, via the display generation component, a second user interface that includes a second user-interactive graphical user interface object corresponding to the first lab type and a third user-interactive graphical user interface object corresponding to a second lab type;
while displaying the second user interface, receiving, via the one or more input devices, a user input designating a lab type;
after receiving the user input designating a lab type, receiving, via the one or more input devices, a second request to display the first user interface that includes the first user-interactive graphical user interface object corresponding to the first lab type; and
in response to receiving the second request to display the first user interface, displaying, via the display generation component, the first user interface that includes the first user-interactive graphical user interface object corresponding to the first lab type, wherein:
in accordance with a determination that the first lab type has been designated via a user input, the first user-interactive graphical user interface object includes the graphical indication of the difference between a first value corresponding to the first lab type and at least a second value corresponding to the first lab type; and
in accordance with a determination that the first lab type has not been designated via a user input, the first user-interactive graphical user interface object does not include the graphical indication of the difference between the first value corresponding to the first lab type and at least the second value corresponding to the first lab type.

10. A method, comprising:
at a computer system that is in communication with a display generation component and one or more input devices:
receiving, via the one or more input devices, a first request to display a first user interface that includes a first user-interactive graphical user interface object corresponding to a first lab type, wherein the first lab type has not been designated by a user input; and
in response to receiving the first request to display the first user interface, displaying, via the display generation component, the first user interface that includes the user-interactive graphical user interface object, wherein the first user-interactive graphical user interface object does not include a graphical indication of a difference between a first value corresponding to the first lab type and at least a second value corresponding to the first lab type;
after displaying the first user interface, displaying, via the display generation component, a second user interface that includes a second user-interactive graphical user interface object corresponding to the first lab type and a third user-interactive graphical user interface object corresponding to a second lab type;
while displaying the second user interface, receiving, via the one or more input devices, a first user input designating the first lab type;
after receiving the first user input, receiving, via the one or more input devices, a second request to display the first user interface that includes the user-interactive graphical user interface object corresponding to the first lab type;
in response to receiving the second request to display the first user interface and based on a determination that the first lab type has been designated via the first user input, displaying, via the display generation component, a first instance of the first user interface that includes the first user-interactive graphical user interface object corresponding to the first lab type, wherein the first user-interactive graphical user interface object includes the graphical indication of the difference between the first value corresponding to the first lab type and at least the second value corresponding to the first lab type;
after displaying the first instance of the first user interface, displaying, via the display generation component, the second user interface that includes the second user-interactive graphical user interface object corresponding to the first lab type and the third user-interactive graphical user interface object corresponding to the second lab type;
while displaying the second user interface after displaying the first instance of the first user interface, receiving, via the one or more input devices, a second user input removing designation of the first lab type;
after receiving the second user input, receiving, via the one or more input devices, a third request to display the first user interface that includes the first user-interactive graphical user interface object corresponding to the first lab type;

in response to receiving the third request to display the first user interface and based on a determination that the first lab type is no longer designated based on the second user input, displaying, via the display generation component, a second instance of the first user interface that includes the first user-interactive graphical user interface object corresponding to the first lab type, wherein the first user-interactive graphical user interface object does not include the graphical indication of the difference between the first value corresponding to the first lab type and at least the second value corresponding to the first lab type.

11. The non-transitory computer-readable storage medium of claim 9, wherein:
   in accordance with a determination that the first value corresponding to the first lab type is greater than the second value corresponding to the first lab type, the graphical indication has a first appearance;
   in accordance with a determination that the first value corresponding to the first lab type is less than the second value corresponding to the first lab type, the graphical indication has a second appearance different than the first appearance; and
   in accordance with a determination that the first value corresponding to the first lab type is equal to the second value corresponding to the first lab type, the graphical indication has a third appearance different from the first appearance and the second appearance.

12. The non-transitory computer-readable storage medium of claim 9, wherein the computer system is associated with a first user account, the one or more programs further including instructions for:
   while performing a process to configure health-related data for sharing with a second user account, displaying a sharing data selection user interface, wherein displaying the sharing data selection user interface includes:
      in accordance with a determination that the first lab type has been designated via the user input, displaying a second user-interactive graphical user interface object that, when selected, causes data of the first lab type to be shared with the second user account upon completion of the process to configure health-related data for sharing with a second user account; and
      in accordance with a determination that the first lab type has not been designated via the user input, forgoing displaying the second user-interactive graphical user interface object that, when selected, causes data of the first lab type to be shared with the second user account upon completion of the process to configure health-related data for sharing with a second user account.

13. The non-transitory computer-readable storage medium of claim 12, the one or more programs further including instructions for:
   during the process to configure health-related data for sharing with a second user account, displaying a lab type sharing selection user-interactive graphical user interface object;
   receiving an input corresponding to the lab type sharing selection user-interactive graphical user interface object;
   in response to receiving the input corresponding to the lab type sharing selection user-interactive graphical user interface object, displaying:
      a third user-interactive graphical user interface object that, when selected, modifies whether data of the first lab type will be shared with the second user account upon completion of the process to configure health-related data for sharing with a second user account; and
      a fourth user-interactive graphical user interface object that, when selected, modifies whether data of a third lab type will be shared with the second user account upon completion of the process to configure health-related data for sharing with a second user account.

14. The non-transitory computer-readable storage medium of claim 9, wherein the user input designating the lab type is selected from the group consisting of:
   a sustained input of greater than a predetermined time on the second user-interactive graphical user interface object,
   an input, which includes movement in a first direction, that corresponds to the second user-interactive graphical user interface object, and
   a set of one or more inputs that includes a first input corresponding to the second user-interactive graphical user interface object.

15. The non-transitory computer-readable storage medium of claim 9, the one or more programs further including instructions for:
   in accordance with a determination that the first lab type has been designated via a user input received via the one or more input devices, including the second user-interactive graphical user interface object corresponding to the first lab type in a first set of one or more user-interactive graphical user interface objects that are displayed, via the display generation component, in a first portion of the second user interface; and
   in accordance with a determination that the first lab type has not been designated via a user input, displaying, via the display generation component, the second user-interactive graphical user interface object corresponding to the first lab type in a second set of one or more user-interactive graphical user interface objects that are displayed, via the display generation component, in a second portion of the second user interface.

16. The non-transitory computer-readable storage medium of claim 15, wherein:
   the first set of one or more user-interactive graphical user interface objects are sorted in the first portion of the second user interface according to a first sorting criteria, and
   the second set of one or more user-interactive graphical user interface objects are sorted in the second portion of the second user interface according to a second sorting criteria.

17. The non-transitory computer-readable storage medium of claim 9, wherein the second user interface includes an edit user-interactive graphical user interface object that, when selected, initiates a process for modifying a designation state of the first lab type.

18. The method of claim 11, wherein:
   in accordance with a determination that the first value corresponding to the first lab type is greater than the second value corresponding to the first lab type, the graphical indication has a first appearance;
   in accordance with a determination that the first value corresponding to the first lab type is less than the second value corresponding to the first lab type, the graphical indication has a second appearance different than the first appearance; and
   in accordance with a determination that the first value corresponding to the first lab type is equal to the second value corresponding to the first lab type, the graphical indication has a third appearance different from the first appearance and the second appearance.

19. The method of claim 11, wherein the computer system is associated with a first user account, further comprising:
while performing a process to configure health-related data for sharing with a second user account, displaying a sharing data selection user interface, wherein displaying the sharing data selection user interface includes:
in accordance with a determination that the first lab type has been designated via the user input, displaying a second user-interactive graphical user interface object that, when selected, causes data of the first lab type to be shared with the second user account upon completion of the process to configure health-related data for sharing with a second user account; and
in accordance with a determination that the first lab type has not been designated via the user input, forgoing displaying the second user-interactive graphical user interface object that, when selected, causes data of the first lab type to be shared with the second user account upon completion of the process to configure health-related data for sharing with a second user account.

20. The method of claim 19, further comprising:
during the process to configure health-related data for sharing with a second user account, displaying a lab type sharing selection user-interactive graphical user interface object;
receiving an input corresponding to the lab type sharing selection user-interactive graphical user interface object;
in response to receiving the input corresponding to the lab type sharing selection user-interactive graphical user interface object, displaying:
a third user-interactive graphical user interface object that, when selected, modifies whether data of the first lab type will be shared with the second user account upon completion of the process to configure health-related data for sharing with a second user account; and
a fourth user-interactive graphical user interface object that, when selected, modifies whether data of a third lab type will be shared with the second user account upon completion of the process to configure health-related data for sharing with a second user account.

21. The method of claim 10, wherein the user input designating the lab type is selected from the group consisting of:
a sustained input of greater than a predetermined time on the second user-interactive graphical user interface object,
an input, which includes movement in a first direction, that corresponds to the second user-interactive graphical user interface object, and
a set of one or more inputs that includes a first input corresponding to the second user-interactive graphical user interface object.

22. The method of claim 10, further comprising:
in accordance with a determination that the first lab type has been designated via a user input received via the one or more input devices, including the second user-interactive graphical user interface object corresponding to the first lab type in a first set of one or more user-interactive graphical user interface objects that are displayed, via the display generation component, in a first portion of the second user interface; and
in accordance with a determination that the first lab type has not been designated via a user input, displaying, via the display generation component, the second user-interactive graphical user interface object corresponding to the first lab type in a second set of one or more user-interactive graphical user interface objects that are displayed, via the display generation component, in a second portion of the second user interface.

23. The method of claim 22, wherein:
the first set of one or more user-interactive graphical user interface objects are sorted in the first portion of the second user interface according to a first sorting criteria, and
the second set of one or more user-interactive graphical user interface objects are sorted in the second portion of the second user interface according to a second sorting criteria.

24. The method of claim 10, wherein the second user interface includes an edit user-interactive graphical user interface object that, when selected, initiates a process for modifying a designation state of the first lab type.

* * * * *

UNITED STATES PATENT AND TRADEMARK OFFICE
CERTIFICATE OF CORRECTION

PATENT NO. : 12,354,718 B2
APPLICATION NO. : 17/540991
DATED : July 8, 2025
INVENTOR(S) : Christopher David Lauritzen et al.

It is certified that error appears in the above-identified patent and that said Letters Patent is hereby corrected as shown below:

In the Claims

In Column 72, Line 56, Claim 18, delete "claim 11," and insert -- claim 10, --, therefor.

In Column 73, Line 4, Claim 19, delete "claim 11," and insert -- claim 10, --, therefor.

Signed and Sealed this
Nineteenth Day of August, 2025

Coke Morgan Stewart
*Acting Director of the United States Patent and Trademark Office*